United States Patent
Rodríguez Vicente et al.

(10) Patent No.: US 9,187,445 B2
(45) Date of Patent: *Nov. 17, 2015

(54) ANTITUMORAL COMPOUNDS

(75) Inventors: Alberto Rodríguez Vicente, Madrid (ES); María Garranzo García-Ibarrola, Madrid (ES); Carmen Murcia Pérez, Madrid (ES); Francisco Sánchez Sancho, Madrid (ES); María del Carmen Cuevas Marchante, Madrid (ES); Cristina Mateo Urbano, Madrid (ES); Isabel Digón Juárez, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 556 days.

This patent is subject to a terminal disclaimer.

(21) Appl. No.: 12/746,974

(22) PCT Filed: Dec. 19, 2008

(86) PCT No.: PCT/EP2008/068049
§ 371 (c)(1),
(2), (4) Date: Jun. 9, 2010

(87) PCT Pub. No.: WO2009/080761
PCT Pub. Date: Jul. 2, 2009

(65) Prior Publication Data
US 2011/0034549 A1  Feb. 10, 2011

(30) Foreign Application Priority Data
Dec. 20, 2007 (EP) .................................... 07123882

(51) Int. Cl.
*C07D 309/10* (2006.01)
*C07D 309/30* (2006.01)
*C07D 309/32* (2006.01)

(52) U.S. Cl.
CPC ............ *C07D 309/10* (2013.01); *C07D 309/30* (2013.01); *C07D 309/32* (2013.01)

(58) Field of Classification Search
CPC ... C07D 309/10; C07D 309/30; C07D 309/32
USPC ........................................ 514/460; 549/417
See application file for complete search history.

(56) References Cited

U.S. PATENT DOCUMENTS

| | | | |
|---|---|---|---|
| 4,855,086 A | 8/1989 | Black et al. | |
| 5,681,847 A * | 10/1997 | Longley et al. | 514/459 |
| 7,446,196 B2 | 11/2008 | Dong | |
| 7,655,808 B2 | 2/2010 | Dong | |
| 8,324,406 B2 | 12/2012 | Lopez et al. | |
| 2005/0272727 A1 * | 12/2005 | Dong et al. | 514/231.5 |
| 2011/0034549 A1 | 2/2011 | Rodriguez Vicente et al. | |

FOREIGN PATENT DOCUMENTS

| | | |
|---|---|---|
| CL | 01390-1993 | 5/1994 |
| CL | 02347-1997 | 5/1998 |
| CL | 02072-1999 | 3/2000 |
| CL | 02073-1999 | 3/2000 |
| EP | 0 111 105 A2 | 6/1984 |
| JP | S61-109717 | 5/1986 |
| JP | H05-039283 | 2/1993 |
| WO | 9610011 A1 | 4/1996 |
| WO | 2005/014574 A1 | 2/2005 |
| WO | WO 2005/117894 | 12/2005 |
| WO | 2007/144423 A1 | 12/2007 |

OTHER PUBLICATIONS

Wolff, Manfred E., Burger's Medicinal Chemistry and Drug Discovery, Fifth Ed., vol. 1: Principles and Practice, John Wiley & Sons, 1995, 975-977.*
Banker, Gilbert S. et al., Modem Pharmaceutics, Marcel Dekker, New York, 1996.*
Kalesse et al. (Synthesis, 2002, p. 981-1003).*
Jayasuriya (Frontiers of Chemistry, 2005, 1-21).*
Dorwald, "Side Reactions in Organic Synthesis," Wiley-VCH, Weinheim, p. IX of preface. pp. 1-15, 2005.
Kuhnt, M et al. "Microbial Conversion Products of Leptomycin B" Applied and Environmental Microbiology, Feb. 1998, 714-720.
Wolff, "Burger's Medicinal Chemistry and Drug Discovery," vol. 1, Principles and Practice, John Wiley & Sons, New York, pp. 975-977, 1997.
Boyd. M. et al. "Some Practical Considerations and Applications of the National Cancer Institute in Vitro Anticancer Drug Discovery Screen" *Drug Dev. Res.* 1995, 34, 91-109.
Faircloth, G. T. et al. "A simple screening procedure for the quantitative measurement of cytotoxicity to resting primary lymphocyte cultures" *J. Tiss. Cult. Meth.* 1988, 11, 201-205.
Gudasheva O. A. et al. "Synthesis, conformation análisis, and anxiolytic activity of retropeptide analogs of 4-cholecystokinin" *Pharm. Chem. J.* 2006, 40, 367-372.
Gudasheva, T. A. et al. "Design and Synthesis of Cholecystokinin-4 Dipeptide Analogues with Anxiolytic and Anxiogenic Activities" *Russ. J. Bioorg. Chem.* 2007, 33, 383-389.
Gunasekera, S. P. et al. "Discodermolide: A new Bioactive Polyhydroxylated Lactone from the Marine Sponge *Discodermia dissoluta*" *J. Org. Chem.* 1990, 55, 4912-4915; *J. Org. Chem.* 1991, 56, 1346.
Haar, E. et al. "Discodermolide, A Cytotoxic Marine Agent that Stabilizes Microtubules more Potently than Taxol" 1996, 35, 243-250.

(Continued)

*Primary Examiner* — Uma Ramachandran
(74) *Attorney, Agent, or Firm* — Lando & Anastasi LLP

(57) ABSTRACT

A compound of general formula (I)

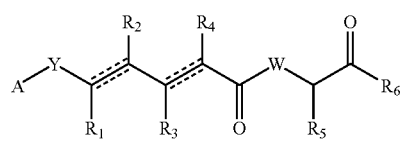

wherein A, Y, W, $R_1$, $R_2$, $R_3$, $R_4$, $R_5$, and $R_6$ take various meanings for use in the treatment of cancer.

31 Claims, No Drawings

(56) References Cited

OTHER PUBLICATIONS

Hung, D. T. et al. "(+)-Discodermolide binds to microtubules in stechiometric ratio to tubulin dimmers, blocks taxol binding and results in mitotic arrest" *Chem. Biol.* 1996, 3, 287-293.

Jansen, R. et al. "Antibiotics from Gliding Bacteria, LXXXIII. The Crocains, Novel Antifungal and Cytotoxic Antibiotics from *Chrondomyces crocatus* and *Chondromyces pediculatus* (Myxobacteria): Isolation and Structure Elucidation" 1999, 1085-1089.

Kunze. B. et al. "Crocacin, a New Electron Transport inhibitor from *Chondromyces Crocatus* (Myxobacteria). Production, Isolation, Physico-chemical and biological properties" *J. Antibiot.* 1994, 47, 881-886.

Mosmann, T. et al. "Rapid Colorimetric Assay for Cellular Growth and Survival: Application to Proliferation and Citotoxicity Assays" *J. Inmunol. Meth.* 1983, 65, 55-63.

Phukan, P. et al. "Flexible Routes to the 5-Hydroxy Acid Fragment of the Cryptophycins" 2003, 1733-1740.

Pla, D. et al. "Modular Total Synthesis of Lamellarin D" *J. Org. Chem.* 2005, 70, 8231-8234.

Pozdnev, V. F. et al. "Activation of carboxilic acids by pyrocarbonates. Application of Di-tert-butyl pyrocarbonate as condensing reagent in the synthesis of amides of protected amino acids and peptides" *Tetrahedron Lett.* 1995, 36, 7115-7118.

Schiff P. B. et al. "Promotion of microtubule assembly in vitro by taxol" *Nature* 1979, 227, 665-667.

Skehan, P. et al. "New Colorimetric Cytotoxicity Assay for Anticancer-Drug Screening" *J. Natl. Cancer Inst..* 1990, 82, 1107-1112.

Stork, G. et al. "A stereoselctive synthesis of (Z)-1-iodo-1-alkenes" *Tetrahedron Lett.* 1989, 30, 2173-2174.

Takeuchi, R. et al. "Stereodivergent Synthesis of (E)- and (Z)-2-Alken-4-yn-1-ols from 2-Propynoic Acid: A Practical Route via 2-Alken-4-ynoates" *J. Org. Chem.* 2000, 65, 1558-1561.

U.S. Appl. No. 12/304,123, filed Jan. 26, 2009, Ma Jesus Martin Lopez.

U.S. Appl. No. 12/746,966, filed Jun. 9, 2010, Alberto Rodriguez Vicente.

Greyer et al., "The National Cancer Institute: Cancer Drug Discovery and Development Program," Seminars in Oncology, vol. 19, No. 6, pp. 622-638, Dec. 1992. cited by other.

Gulledge Brian M et al: "Microcystin Analogues Comprised Only of ADDA and a Single Additional Amino Acid Retain Moderate Activity as PP1 /PP2A Inhibitors" Bioorganic&; Medicinal Chemistry Letters, Pergamon, Elsevier Science, GB, vol. 13, No. 17, Sep. 1, 2003, pp. 2907-2911, XP009094989 ISSN: 0960-894X.

Hermann C et al: "Total Synthesis of 1-27 Hapalosin and Two Ring Expanded Analogs" Tetrahedron, Elsevier Science Publishers, Amsterdam, NL, vol. 56, No. 43, Oct. 20, 2000, pp. 8461-8471, XP004238495 ISSN: 0040-4020 compound 23.

International Preliminary Report on Patentability & Written Opinion for PCT/EP07/055959, dated Dec. 16, 2008.

International Preliminary Report on Patentability & Written Opinion for PCT/EP08/68049, dated Jun. 22, 2010.

International Preliminary Report on Patentability & Written Opinion for PCT/EP08/68065, dated Jun. 22, 2010.

International Search Report for PCT/EP07/055959, dated Feb. 10, 2007.

International Search Report for PCT/EP08/68065, dated Jul. 2, 2009.

International Search Report nofor PCT/EP08/68049, dated Jun. 22, 2010.

Jones et al: "Microbial modification of mycophenolic acid" Journal of the Chemical Society, Section C: Organic Chemistry, Chemical Society. Letchworth, GB, val. 12, Jan. 1, 1970, pp. 1725-1737, XP002165092 ISSN: 0022-4952.

Lipomi et al., "Total Synthesis of Basiliskamides A and B," Organic Letters, 6(20), pp. 3533-3536, 2004. cited by other.

M. Rouchi, Chemical and Engineering News, 81(41), 104-107, 2003).

Nicolaou et al., "Total Synthesis of Rapamycin," J. Am. Chem. Soc., 115, pp. 4419-4420, 1993. cited by other.

Nicolaou et al., "Total Synthesis of the Novel Immunosuppressant Sanglifehrin A," J. Am. Chem. Soc., 122, pp. 3830-3838, 2000. cited by other.

Paquette et al., "A Convergent Three-Component Total Synthesis of the Powerful Immunosuppressant (−)-Sanglifehrin A," J. Am. Chem. Soc., 124, pp. 4257-4270, 2002. cited by other.

Parker et al., "The Total Synthesis of (−)-SNF4435 C and (+)-SNF 4435 D," J. Am. Chem. Soc., 126, pp. 15968-15969, 2004. cited by other.

Paterson et al., "Total Synthesis and Configurational Assignment of (−)- Dictyostatin, a Microtubule-Stabilizing Macrolide of Marine Sponge Origin," Angewandte Chemie Int. Ed., 43, pp. 4629-4633, 2004. cited by other.

Schmid et al., "Total Synthesis of Monensin, 1, Stereocontrolled Synthesis of the Lef Half of Monensin," Journal of the American Chemical Society, p. 259-260, 1979. cited by other.

Silverman, The Organic Chemistry of Drug Design and Drug Action, Academic Press, Inc., 1992.

Smith et al., "(+)-Phorboxazole A Synthetic Studies. A Highly Convergent, Second Generation Total Synthesis of (+)- Phorboxazole A," Organic Letters, 7(20), pp. 4399-4402, 2005. cited by other.

Smith et al., "Total Synthesis of Rapamycin and Demethoxyrapamycin," J. Am. Chem. Soc., 117, pp. 5407-5408, 1995. cited by other.

Suggitt et al., "50 Years of Preclinical Anticancer Drug Screening: Empirical to Target-Driven Approaches," Clinical Cancer Research, vol. 11, Feb. 1, 2005, pp. 971-981. cited by other.

Williams et al., "Total Synthesis of (+)-Amphidinolide J," J. Am. Chem. Soc., 120, pp. 11198-11199, 1998. cited by other.

\* cited by examiner

ANTITUMORAL COMPOUNDS

FIELD OF THE INVENTION

The present invention relates to new antitumoral compounds, pharmaceutical compositions containing them and their use as antitumoral agents.

BACKGROUND OF THE INVENTION

In 1990, Gunasekera S P et al. reported the isolation of a new polyhydroxylated lactone, (+)-discodermolide, from the deep-water Caribbean sponge *Discodermia dissoluta* (Gunasekera S P et al. J. Org. Chem. 1990, 55, 4912-4915 and J. Org. Chem. 1991, 56, 1346).

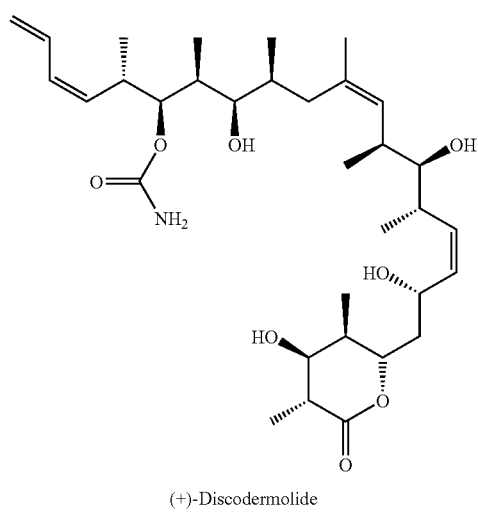

(+)-Discodermolide

This compound has been revealed to be a potent antimitotic agent (Hung D T et al. Chem. Biol. 1996, 3, 287-293 and ter Haar E et al. Biochemistry 1996, 35, 243-250), possessing a mode of action similar to that of the clinically proven anticancer agent paclitaxel (Schiff P B et al. Nature 1979, 277, 665-667). Both natural products arrest the cell cycle at the M phase, promote microtubule formation, and have similar inhibitory effects against breast cancer carcinoma ($IC_{50}$ of 2.4 nM and 2.1 nM, respectively).

On the other hand, some unusual linear dipeptides containing a N-acyl enamide functionality have been isolated from a myxobacteria belonging to the *Chondromyces* genus (Kunze B et al. J. Antibiot. 1994, 47, 881-886 and Jansen R et al. J. Org. Chem. 1999, 1085-1089). Specifically, these compounds are crocacins A, B, C and D and are a group of electron transport inhibitors.

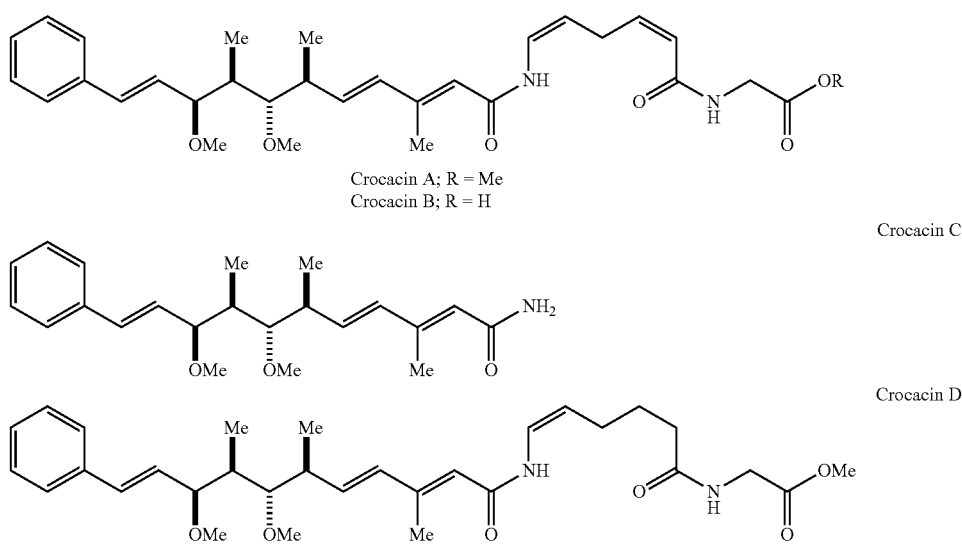

Crocacins A-D moderately inhibit the growth of a few Gram-positive bacteria and are potent inhibitors of animal cell cultures and several yeasts and fungi. The most active is crocacin D which showed a MIC of 1.4 ng/mL against the fungus *Saccharomyces cerevisiae* and strong toxicity ($IC_{50}$ of 0.06 mg/L) toward L929 mouse fibroblast cell culture.

Gudasheva et al. (Russian Journal of Bioorganic Chemistry, 2007, 44(4), 413-420, and Pharmaceutical Chemistry Journal, 2006, 40(7), 367-372) reported the design of dipeptide compounds based on the structure of the endogenous tetrapeptide cholescystokinin-4 (CCK-4). In this regard, it is disclosed that L-thryptophan derivatives exhibited anxiolytic properties and the D-thryptophan derivatives, anxiogenic properties. Two of the dipeptide compounds disclosed by Gudasheva et al. are the following:

Compound R

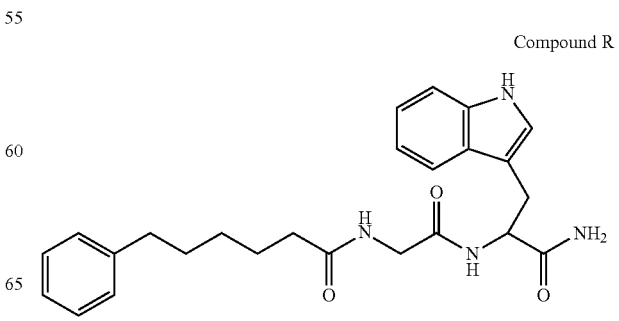

Compound U

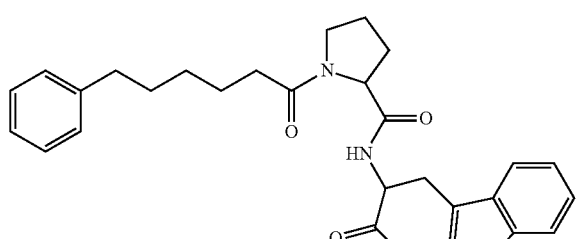

and the following compounds were disclosed as intermediates in the synthesis of compounds R and U:

Compound S

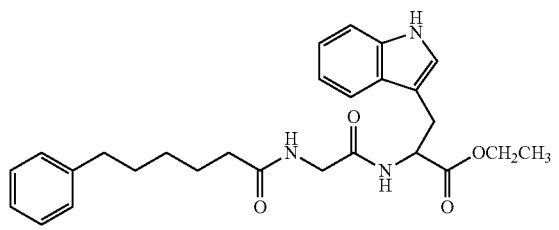

Compound T

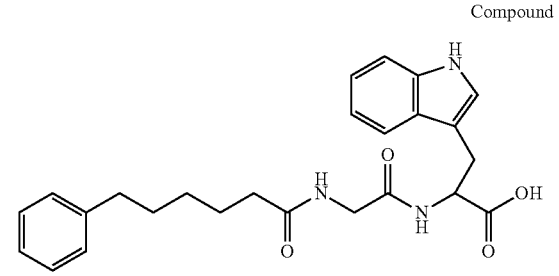

Compound V

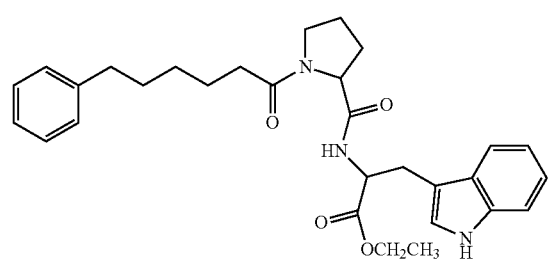

Compound W

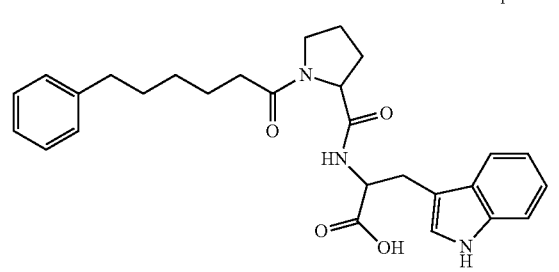

Compound Y

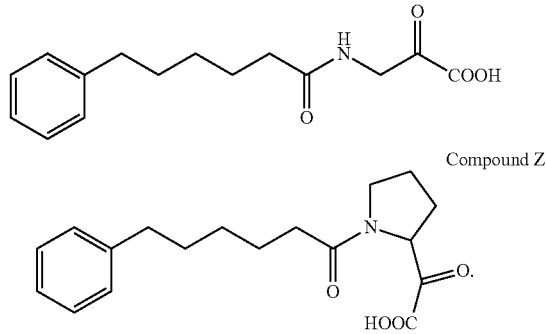

Compound Z

Cancer is a leading cause of death in animals and humans. Huge efforts have been and are still being undertaken in order to obtain an antitumor agent active and safe to be administered to patients suffering from a cancer. The problem to be solved by the present invention is to provide compounds that are useful in the treatment of cancer.

SUMMARY OF THE INVENTION

In one aspect, the present invention is directed to compounds of general formula I or pharmaceutically acceptable salts, tautomers, prodrugs or stereoisomers thereof

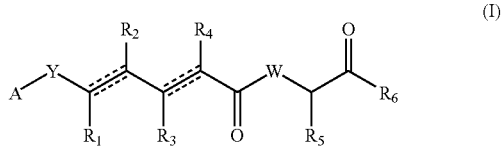

(I)

wherein Y is selected from —$CHR_{ay}$—, —$CHR_{ay}$—$CHR_{by}$—, —$CR_{ay}$=$CR_{by}$—, —C≡C—, —$CHR_{ay}$—$CHR_{by}$—$CHR_{cy}$—, —$CHR_{ay}$—$CR_{by}$=$CR_{cy}$—, and —$CHR_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_1$, $R_2$, $R_3$, $R_4$, and $R_5$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

A is selected from

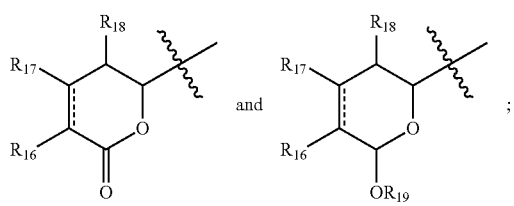

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

$R_8$ is selected from hydrogen, $COR_a$, $COOR_a$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

$R_{10}$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each dotted line represents an optional additional bond, but when a triple bond exists between the C atoms to which $R_1$ and $R_2$ are attached, $R_1$ and $R_2$ are absent, and when a triple bond exists between the C atoms to which $R_3$ and $R_4$ are attached, $R_3$ and $R_4$ are absent;

and
when A is

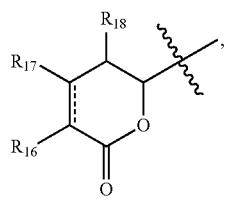

then
$R_9$ is selected from hydrogen, $COR_a$, $COOR_a$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl, with the proviso that when Y is —$CHR_{ay}$—$CHR_{by}$—$CHR_{cy}$— or —$CHR_{ay}$—$CR_{by}$=$CR_{cy}$— and a single or a double bond exists between the C atoms to which $R_3$ and $R_4$ are attached then $R_9$ is substituted or unsubstituted $C_4$-$C_{12}$ alkenynyl; and
when A is

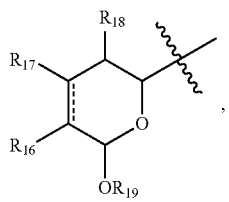

then
$R_9$ is selected from hydrogen, $COR_a$, $COOR_a$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

each $R_{16}$, $R_{17}$ and $R_{18}$ are independently selected from hydrogen, $OR_a$, $OCOR_a$, $OCOOR_a$, $NR_aR_b$, $NR_aCOR_b$, and $NR_aC$(=$NR_a$)$NR_aR_b$, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_{19}$ is selected from hydrogen, $COR_a$, $COOR_a$, $CONR_aR_b$, $S(O)R_a$, $SO_2R_a$, $P(O)(R_a)OR_b$, $SiR_aR_bR_c$, substituted or unsubstituted $C_1$-$C_{12}$ alkyl, substituted or unsubstituted $C_2$-$C_{12}$ alkenyl and substituted or unsubstituted $C_2$-$C_{12}$ alkynyl; and each $R_a$, $R_b$, and $R_c$ are independently selected from hydrogen, substituted or unsubstituted $C_1$-$C_{12}$ alkyl or unsubstituted $C_2$-$C_{12}$ alkenyl, substituted or unsubstituted $C_2$-$C_{12}$ alkynyl, substituted or unsubstituted aryl and substituted or unsubstituted heterocyclic group.

In another aspect, the present invention is also directed to a compound of formula I, or a pharmaceutically acceptable salt, tautomer, prodrug or stereoisomer thereof, for use as medicament In another aspect, the present invention is also directed to a compound of formula I, or a pharmaceutically acceptable salt, tautomer, prodrug or stereoisomer thereof, for use as medicament for treating cancer.

In a further aspect, the present invention is also directed to the use of compounds of formula I, or pharmaceutically acceptable salts, tautomers, prodrugs or stereoisomers thereof, in the treatment of cancer, or in the preparation of a medicament for the treatment of cancer. Other aspects of the invention are methods of treatment, and compounds for use in these methods. Therefore, the present invention further provides a method of treating any mammal, notably a human, affected by cancer which comprises administering to the affected individual a therapeutically effective amount of a compound of formula I, or a pharmaceutically acceptable salt, tautomer, prodrug or stereoisomer thereof.

In a yet further aspect, the present invention is also directed to a compound of formula I, or a pharmaceutically acceptable salt, tautomer, prodrug or stereoisomer thereof, for use as anticancer agent.

In another aspect, the present invention is directed to pharmaceutical compositions comprising a compound of formula I, or a pharmaceutically acceptable salt, tautomer, prodrug or stereoisomer thereof, together with a pharmaceutically acceptable carrier or diluent.

DETAILED DESCRIPTION OF PREFERRED EMBODIMENTS

The present invention relates to compounds of general formula I as defined above.

In these compounds the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, propyl, isopropyl and butyl, including tert-butyl, sec-butyl and isobutyl are particularly preferred alkyl groups in the compounds of the present invention. Another preferred class of alkyl groups has from 6 to about 10 carbon atoms; and even more preferably 7, 8 or 9 carbon atoms. Heptyl, octyl and nonyl are the most preferred alkyl groups of this class.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. Another preferred class of alkenyl and alkynyl groups has from 4 to about 10 carbon atoms, still more preferably 6 to about 10 carbon atoms; and even more preferably 7, 8 or 9 carbon atoms.

We define alkenynyl group as an alkyl group containing one or more double bonds and one or more triple bonds, and preferred alkenynyl groups are those having from 4 to about 12 carbon atoms. One more preferred class of alkenynyl groups has from 6 to about 10 carbon atoms.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms, most preferably 5, 6 or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, CO$_2$H, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list.

Suitable halogen substituents in the compounds of the present invention include F, Cl, Br and I.

Suitable protecting groups for OH are well known for the skilled person in the art. A general review of protecting groups in organic chemistry is provided by Wuts, P G M and Greene T W in Protecting Groups in Organic Synthesis, 4$^{th}$ Ed. Wiley-Interscience, and by Kocienski P J in Protecting Groups, 3$^{rd}$ Ed. Georg Thieme Verlag. These references provide sections on protecting groups for OH. All these references are incorporated by reference in their entirety. Examples of such protected OH include ethers, silyl ethers, esters, sulfonates, sulfenates and sulfinates, carbonates and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,t]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxido. In the case of silyl ethers the protecting group for the OH can be selected from trimethylsilyl, triethylsilyl, triisopropylsilyl, dimethylisopropylsilyl, diethylisopropylsilyl, dimethylhexylsilil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2-{{[(4-methoxytrityl)thio]methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothiolyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate. The mention of these groups should be not interpreted as a limitation of the scope of the invention, since they have been mentioned as a mere illustration of protecting groups for OH, but further groups having said function may be known by the skilled person in the art, and they are to be understood to be also encompassed by the present invention.

The term "pharmaceutically acceptable salts, prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts and prodrugs can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" as used in this application is defined here as meaning a chemical compound having undergone a chemical derivation such as substitution or addition of a further chemical group to change (for pharmaceutical use) any of its physicochemical properties, such as solubility or bioavailability, e.g. ester and ether derivatives of an active compound that yield the active compound per se after administration to a subject. Examples of well known methods of producing a prodrug of a given acting compound are known to those skilled in the art and can be found e.g. in Krogsgaard-Larsen et al., Textbook of Drugdesign and Discovery, Taylor & Francis (April 2002).

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the compounds of the present invention represented by the above described formula I may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropisomers. Specifically, the term tautomer refers to one of two or more structural isomers of a compound, that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In compounds of general formula I, particularly preferred Y is —$CHR_{ay}$—, —$CR_{ay}$=$CR_{by}$—, and —$CHR_{ay}$—$CR_{by}$=$CR_{cy}$—, wherein $R_{ay}$, $R_{by}$, and $R_{cy}$ are as defined before.

Particularly preferred $R_{ay}$, $R_{by}$, and $R_{cy}$ are hydrogen and substituted or unsubstituted $C_1$-$C_{12}$ alkyl. More preferred $R_{ay}$, $R_{by}$, and $R_{cy}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl, and substituted or unsubstituted butyl, including substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen and methyl are the most preferred $R_{ay}$, $R_{by}$, and $R_{cy}$ groups. Specifically, when Y is —$CHR_{ay}$— then particularly preferred $R_{ay}$ is methyl, when Y is —$CR_{ay}$=$CR_{by}$— then particularly preferred $R_{ay}$ is hydrogen and particularly preferred $R_{by}$ is methyl, and when Y is —$CHR_{ay}$—$CR_{by}$=$CR_{cy}$— then particularly preferred $R_{ay}$ is hydrogen or methyl, particular preferred $R_{by}$ is hydrogen, and particularly preferred $R_{cy}$ is methyl.

Particularly preferred $R_1$, $R_2$, $R_3$, $R_4$, and $R_5$ are hydrogen and substituted or unsubstituted $C_1$-$C_{12}$ alkyl. More preferred $R_1$, $R_2$, $R_3$, $R_4$, and $R_5$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl, and benzyl are the most preferred $R_1$, $R_2$, $R_3$, $R_4$, and $R_5$ groups. Specifically, particularly preferred $R_1$, $R_2$, $R_3$, and $R_4$ are hydrogen. And particularly preferred $R_5$ are methyl, isopropyl, and tert-butyl.

Particularly preferred W is $NR_7$ wherein $R_7$ is as defined before.

Particularly preferred $R_6$ is $NR_8R_9$ and $OR_{10}$ wherein $R_8$, $R_9$, and $R_{10}$ are as defined before, and even more preferred $R_6$ is $NR_8R_9$.

Particularly preferred $R_7$ and $R_8$ are hydrogen and substituted or unsubstituted $C_1$-$C_{12}$ alkyl. More preferred $R_7$ and $R_8$ are hydrogen and substituted or unsubstituted $C_1$-$C_6$ alkyl; and even more preferred is hydrogen, methyl, ethyl, propyl, isopropyl and butyl, including tert-butyl. Hydrogen is the most preferred.

In another embodiment, it is particularly preferred that $R_7$ and $R_5$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

Particularly preferred is the presence of one or more additional bonds in the places indicated with a dotted line. More preferred is the presence of one additional bond between the C atoms to which $R_1$ and $R_2$ are attached, and the presence of one or two additional bonds between the C atoms to which $R_3$ and $R_4$ are attached. In addition, the stereochemistry of each double bond may exist as (E) or (Z). The single isomers and mixtures of the isomers fall within the scope of the present invention.

In compounds wherein A is

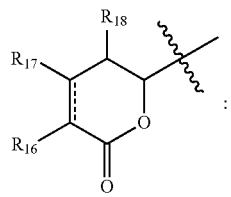

:

When Y is a) —$CHR_{ay}$—, —$CHR_{ay}$—$CHR_{by}$—, —$CR_{ay}$=$CR_{by}$—, —C≡C—, or —$CHR_{ay}$—C≡C—; or b) —$CHR_{ay}$—$CHR_{by}$—$CHR_{cy}$— or —$CHR_{ay}$—$CR_{by}$=$CR_{cy}$—, and a triple bond exists between the C atoms to which $R_3$ and $R_4$ are attached, then particularly preferred $R_9$ is hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. More preferably is hydrogen, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. The preferred substituted alkyl, substituted alkenyl, substituted alkynyl, and substituted alkenynyl may present not only one but two or more substituents. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, and hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkyl, alkenyl, alkynyl and alkenynyl groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR', OCONHR', OCONR'R', CONHR', CONR'R', and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkyl, alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl, Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl, alkenyl, alkynyl and alkenynyl groups.

When Y is —$CHR_{ay}$—$CHR_{by}$—$CHR_{cy}$— or —$CHR_{ay}$—$CR_{by}$=$CR_{cy}$— and a single or a double bond exists between the C atoms to which $R_3$ and $R_4$ are attached, then $R_9$ is substituted or unsubstituted $C_4$-$C_{12}$ alkenynyl. The preferred substituted alkenynyl may present not only one but two or more substituents. More preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkenynyl groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenynyl groups are halogen, OR', =O, OCOR', OCONHR', OCONR'R', CONHR', CONR'R', and protected OH, wherein each of the R' groups is preferably selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted aryl. Even more preferred substituents for these alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted C$_1$-C$_6$ alkyl, and substituted or unsubstituted aryl. Cl, OH, =O, OCONH$_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3[2-(triphenylmethoxy)ethoxy]disiloxane-1-yl, and fluorous silyl, are the most preferred substituents for these alkenynyl groups.

Particularly preferred R$_{16}$ is hydrogen, OR$_a$ and OCOR$_a$, wherein R$_a$ is selected from hydrogen and substituted or unsubstituted C$_1$-C$_{12}$ alkyl. Particularly preferred R$_a$ is hydrogen and substituted or unsubstituted C$_1$-C$_6$ alkyl; and even more preferred is hydrogen, methyl, ethyl, propyl, isopropyl and butyl, including tert-butyl. Hydrogen, OH and methoxy are the most preferred R$_{16}$ groups.

Particularly preferred R$_{17}$ and R$_{18}$ are hydrogen and substituted or unsubstituted C$_1$-C$_{12}$ alkyl. More preferred R$_{17}$ and R$_{18}$ are hydrogen and substituted or unsubstituted C$_1$-C$_6$ alkyl, and even more preferred are hydrogen.

On the other hand, in compounds wherein A is

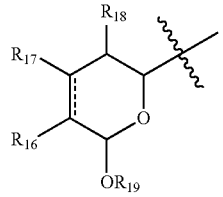

Particularly preferred R$_9$ is hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl, and more preferably is hydrogen, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl. The preferred substituted alkyl, substituted alkenyl, substituted alkynyl and substituted alkenynyl may present not only one but two or more substituents. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, and hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkyl, alkenyl, alkynyl and alkenynyl groups are OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR", OCONHR', OCONR'R', CONHR', CONR'R', and protected OH, wherein each of the R' groups is preferably selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted aryl. Even more preferred substituents for these alkyl, alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl, Cl, OH, =O, OCONH$_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl) silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl, alkenyl, alkynyl and alkenynyl groups.

Particular preferred $R_{16}$ is hydrogen, $OR_a$ and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, propyl, isopropyl and butyl, including tert-butyl. Hydrogen, OH and methoxy are the most preferred $R_{16}$ groups.

Particularly preferred $R_{17}$ and $R_{19}$ are hydrogen and substituted or unsubstituted $C_1$-$C_{12}$ alkyl and particularly preferred $R_{19}$ is hydrogen, substituted or unsubstituted $C_1$-$C_{12}$ alkyl and $COR_a$, wherein $R_a$ is a substituted or unsubstituted $C_1$-$C_{12}$ alkyl. More preferred $R_{17}$ and $R_{18}$ are hydrogen and substituted or unsubstituted $C_1$-$C_6$ alkyl and more preferred $R_{19}$ are hydrogen, substituted or unsubstituted $C_{1-6}$ alkyl and $COR_a$, wherein $R_a$ is a substituted or unsubstituted $C_1$-$C_6$ alkyl. Particularly preferred $R_a$ is methyl, ethyl, propyl, isopropyl and butyl, including tert-butyl. Even more preferred $R_{17}$, $R_{18}$ and $R_{19}$ are hydrogen.

Particularly preferred is the presence of one or more additional bonds in the places indicated with a dotted line. More preferred is the presence of one additional bond between the C atoms to which $R_1$ and $R_2$ are attached, and the presence of one or two additional bonds between the C atoms to which $R_3$ and $R_4$ are attached. In addition, the stereochemistry of each double bond may exist as (E) or (Z). The single isomers and mixtures of the isomers fall within the scope of the present invention.

More particularly, preferred compounds of general formula I are those also having general formula IA or pharmaceutically acceptable salts, tautomers, prodrugs or stereoisomers thereof

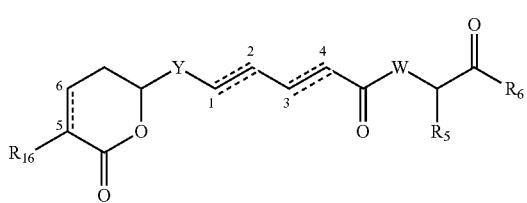

(IA)

wherein Y is selected from —$CHR_{ay}$—, —$CHR_{ay}$—$CHR_{by}$—, —$CR_{ay}$=$CR_{by}$—, —C≡C—, —$CHR_{ay}$—$CHR_{by}$—$CHR_{cy}$—, —$CHR_{ay}$—$CR_{by}$=$CR_{cy}$—, and —$CHR_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_5$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

each $R_8$ and $R_9$ are independently selected from hydrogen, $COR_a$, $COOR_a$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl, with the proviso that when Y is —$CHR_{ay}$—$CHR_{by}$—$CHR_{cy}$— or —$CHR_{ay}$—$CR_{by}$=$CR_{cy}$— and a single or a double bond exists between $C_3$ and $C_4$, then $R_9$ is substituted or unsubstituted $C_4$-$C_{12}$ alkenynyl;

$R_{10}$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_{16}$ is selected from hydrogen, $OR_a$, $OCOR_a$, $OCOOR_a$, $NR_aR_b$, $NR_aCOR_b$, and $NR_aC(=NR_a)NR_aR_b$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and each $R_a$ and $R_b$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group; and each dotted line represents an optional additional bond.

In compounds of general formula IA, particularly preferred Y is —$CHR_{ay}$—, —$CR_{ay}$=$CR_{by}$—, and —$CHR_{ay}$—$CR_{by}$=$CR_{cy}$—, wherein $R_{ay}$, $R_{by}$, and $R_{cy}$ are as defined before.

Particularly preferred $R_{ay}$, $R_{by}$, and $R_{cy}$ are hydrogen and substituted or unsubstituted $C_1$-$C_{12}$ alkyl. More preferred $R_{ay}$, $R_{by}$, and $R_{cy}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl, and substituted or unsubstituted butyl, including substituted or unsubstituted tert-butyl, substituted or unsubstituted isobutyl, and substituted or unsubstituted sec-butyl. Preferred substituents of said groups are OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$; SH, $NH_2$, $NHC(=NH)NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen and methyl are the most preferred $R_{ay}$, $R_{by}$, and $R_{cy}$ groups. Specifically, when Y is —$CHR_{ay}$— then particularly preferred $R_{ay}$ is methyl, when Y is —$CR_{ay}=CR_{by}$— then particularly preferred $R_{ay}$ is hydrogen and particularly preferred $R_{by}$ is methyl, and when Y is —$CHR_{ay}$—$CR_{by}=CR_{cy}$— then particularly preferred $R_{ay}$ is hydrogen or methyl, particular preferred $R_{by}$ is hydrogen, and particularly preferred $R_{cy}$ is methyl.

Particularly preferred $R_5$ is hydrogen and substituted or unsubstituted $C_1$-$C_{12}$ alkyl. More preferred $R_5$ is hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, $NHC(=NH)NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl and benzyl are the most preferred $R_5$ groups, and even most preferred methyl, isopropyl, and tert-butyl.

Particularly preferred W is $NR_7$ wherein $R_7$ is as defined before.

Particularly preferred $R_6$ is $NR_8R_9$, wherein $R_8$ and $R_9$ are as defined before.

Particularly preferred $R_7$ and $R_8$ are hydrogen and substituted or unsubstituted $C_1$-$C_{12}$ alkyl. More preferred $R_7$ and $R_8$ are hydrogen and substituted or unsubstituted $C_1$-$C_6$ alkyl; and even more preferred are hydrogen, methyl, ethyl, propyl, isopropyl and butyl, including tert-butyl. Hydrogen is the most preferred.

In another embodiment, it is particularly preferred that $R_7$ and $R_5$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

When Y is a) —$CHR_{ay}$—, —$CHR_{ay}$—$CHR_{by}$—, —$CR_{ay}=CR_{by}$—, —C≡C—, or —$CHR_{ay}$—C≡C—; or b) —$CHR_{ay}$—$CHR_{by}$—$CHR_{cy}$— or —$CHR_{ay}$—$CR_{by}=CR_{cy}$— and a triple bond exists between $C_3$ and $C_4$, then particularly preferred $R_9$ is hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. More preferably is hydrogen, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. The preferred substituted alkyl, substituted alkenyl, substituted alkynyl and substituted alkenynyl may present not only one but two or more substituents. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkyl, alkenyl, alkynyl and alkenynyl groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR", OCONHR', OCONR'R', CONHR', CONR'R', and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkyl, alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-

1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl, Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl, alkenyl, alkynyl and alkenynyl groups.

When Y is —$CHR_{ay}$—$CHR_{by}$—$CHR_{cy}$— or —$CHR_{ay}$—$CR_{by}$=$CR_{cy}$— and a single or a double bond exists between $C_3$ and $C_4$, then $R_9$ is substituted or unsubstituted $C_4$-$C_{12}$ alkenynyl. The preferred substituted alkenynyl may present not only one but two or more substituents. More preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkenynyl groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenynyl groups are halogen, OR', =O, OCOR", OCONHR', OCONR'R', CONHR', CONR'R', and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl) silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl, Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkenynyl groups.

Particular preferred $R_{16}$ is hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, propyl, isopropyl and butyl, including tert-butyl. Hydrogen, OH and methoxy are the most preferred $R_{16}$ groups.

Particularly preferred is the presence of one or more additional bonds in the places indicated with a dotted line. More preferred is the presence of one additional bond between $C_1$ and $C_2$, and/or the presence of one or two additional bonds between $C_3$ and $C_4$, and/or the presence of one additional bond between $C_5$ and $C_6$. In addition, the stereochemistry of each double bond may exist as (E) or (Z). The single isomers and mixtures of the isomers fall within the scope of the present invention.

Another particular preferred compounds of general formula I are those having general formula IB or pharmaceutically acceptable salts, tautomers, prodrugs or stereoisomers thereof

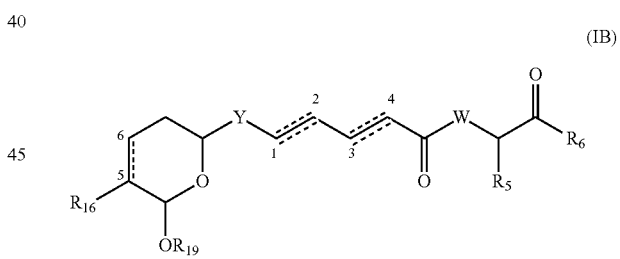

(IB)

wherein Y is selected from —$CHR_{ay}$—, —$CHR_{ay}$—$CHR_{by}$—, —$CR_{ay}$=$CR_{by}$—, —C≡C—, —$CHR_{ay}$—$CHR_{by}$—$CHR_{cy}$—, —$CHR_{ay}$—$CR_{by}$=$CR_{cy}$—, and —$CHR_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_5$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

each $R_8$ and $R_9$ are independently selected from hydrogen, $COR_a$, $COOR_a$, substituted or unsubstituted $C_1$-$C_{12}$ alkyl, substituted or unsubstituted $C_2$-$C_{12}$ alkenyl, substituted or unsubstituted. $C_2$-$C_{12}$ alkynyl, and substituted or unsubstituted $C_4$-$C_{12}$ alkenynyl;

$R_{10}$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_{16}$ is selected from hydrogen, $OR_a$, $OCOR_a$, $OCOOR_a$, $NR_aR_b$, $NR_aCOR_b$, and $NR_aC(=NR_a)NR_aR_b$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_{19}$ is selected from hydrogen, $COR_a$, $COOR_a$, $CONR_aR_b$, $S(O)R_a$, $SO_2R_a$, $P(O)(R_a)OR_b$, $SiR_aR_bR_c$, substituted or unsubstituted $C_1$-$C_{12}$ alkyl, substituted or unsubstituted $C_2$-$C_{12}$ alkenyl and substituted or unsubstituted $C_2$-$C_{12}$ alkynyl; and each $R_a$, $R_b$ and $R_c$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group; and each dotted line represents an optional additional bond.

In compounds of general formula IB, particularly preferred Y is —$CHR_{ay}$—, —$CR_{ay}$=$CR_{by}$—, and —$CHR_{ay}$—$CR_{by}$=$CR_{cy}$—, wherein $R_{ay}$, $R_{by}$, and $R_{cy}$ are as defined before.

Particularly preferred $R_{ay}$, $R_{by}$, and $R_{cy}$ are hydrogen and substituted or unsubstituted $C_1$-$C_{12}$ alkyl. More preferred $R_{ay}$, $R_{by}$, and $R_{cy}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl, and substituted or unsubstituted butyl, including substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen and methyl are the most preferred $R_{ay}$, $R_{by}$, and $R_{cy}$ groups. Specifically, when Y is —$CHR_{ay}$— then particularly preferred $R_{ay}$ is methyl, when Y is —$CR_{ay}$=$CR_{by}$— then particularly preferred $R_{ay}$ is hydrogen and particularly preferred $R_{by}$ is methyl, and when Y is —$CHR_{ay}$—$CR_{by}$=$CR_{cy}$— then particularly preferred $R_{ay}$ is hydrogen or methyl, particular preferred $R_{by}$ is hydrogen, and particularly preferred $R_{cy}$ is methyl.

Particularly preferred $R_5$ is hydrogen and substituted or unsubstituted $C_1$-$C_{12}$ alkyl. More preferred $R_5$ is hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl and benzyl are the most preferred $R_5$ groups, and even most preferred methyl, isopropyl, and tert-butyl.

Particularly preferred W is $NR_7$ wherein $R_7$ is as defined before.

Particularly preferred $R_6$ is $NR_8R_9$, wherein $R_8$ and $R_9$ are as defined before.

Particularly preferred $R_7$ and $R_8$ are hydrogen and substituted or unsubstituted $C_1$-$C_{12}$ alkyl. More preferred $R_7$ and $R_8$ are hydrogen and substituted or unsubstituted $C_1$-$C_6$ alkyl; and even more preferred are hydrogen, methyl, ethyl, propyl, isopropyl and butyl, including tert-butyl. Hydrogen is the most preferred.

In another embodiment, it is particularly preferred that $R_7$ and $R_5$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

Particularly preferred $R_9$ is hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl, and more preferably is hydrogen, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. The preferred substituted alkyl, substituted alkenyl, substituted alkynyl and substituted alkenynyl may present not only one but two or more substituents. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, and hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkyl, alkenyl, alkynyl and alkenynyl groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR', OCONHR', OCONR'R', CONHR', CONR'R', and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkyl, alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl, Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl, alkenyl, alkynyl and alkenynyl groups.

Particular preferred $R_{16}$ is hydrogen, $OR_a$ and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, propyl, isopropyl and butyl, including tert-butyl. Hydrogen, OH and methoxy are the most preferred $R_{16}$ groups.

Particularly preferred $R_{19}$ is hydrogen, substituted or unsubstituted $C_1$-$C_{12}$ alkyl and $COR_a$, wherein $R_a$ is a substituted or unsubstituted $C_1$-$C_{12}$ alkyl. More preferred $R_{19}$ is hydrogen, substituted or unsubstituted $C_1$-$C_6$ alkyl and $COR_a$, wherein $R_a$ is a substituted or unsubstituted $C_1$-$C_6$ alkyl. Particularly preferred $R_a$ is methyl, ethyl, propyl, isopropyl and butyl, including tert-butyl. Even more preferred $R_{19}$ is hydrogen.

Particularly preferred is the presence of one or more additional bonds in the places indicated with a dotted line. More preferred is the presence of one additional bond between $C_1$ and $C_2$, and/or the presence of one or two additional bonds between $C_3$ and $C_4$, and/or the presence of one additional bond between $C_5$ and $C_6$. In addition, the stereochemistry of each double bond may exist as (E) or (Z). The single isomers and mixtures of the isomers fall within the scope of the present invention.

The compounds of the invention can be obtained synthetically by joining different fragments as indicated in the Scheme A.

Scheme A

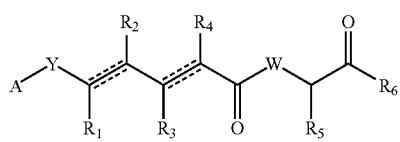 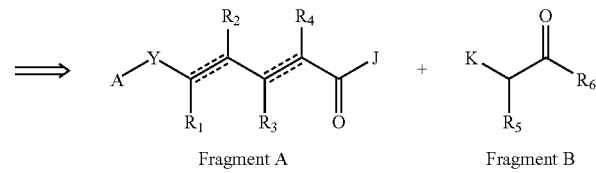

Fragment A  Fragment B

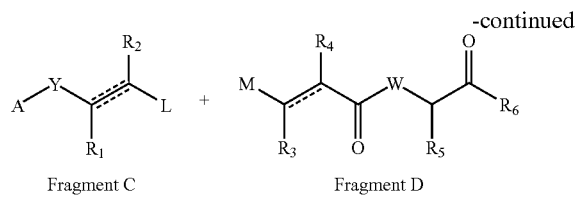

Fragment C + Fragment D where $R_1$, $R_2$, $R_3$, $R_4$, $R_5$, $R_6$, A, Y and W are the desired groups or an appropriate protecting group as needed, and J, K, L, and M are appropriate reacting or leaving groups.

The compounds of the invention can be obtained by either of the following strategies:

1) Fragments A and B can be coupled following standard procedures in organic chemistry (i.e. Bodanszky M and Bodanszky A, The Practice of Peptide Synthesis, Springer-Verlag, 1993).

2) Fragments C and D can be coupled following standard procedures of organometallic chemistry (i.e. R. B. Crabtree, "The Organometallic Chemistry of the Transition Metals", 2nd Ed., Wiley, Nueva York, 1994).

Fragments A, B, C and D can be independently prepared following standard procedures in organic synthesis.

Deprotection of the protecting groups can be achieved according to known procedures in organic synthesis (Greene and Wuts, Protective Groups in Organic Synthesis, 3$^{rd}$ ed., Wiley-Interscience; Burke and Danheiser, Handbook of Reagents for Organic Synthesis: Oxidizing and Reducing Agents, Wiley; Pla D et al. J. Org. Chem. 2005, 70, 8231).

When necessary, appropriate protecting groups can be used on the substituents to ensure that reactive groups are not affected. The synthesis can be designed to employ precursor substituents which can be converted at the appropriate stage to a desired substituent. Saturation or unsaturation in the ring-structure can be introduced or removed as part of the synthesis. Starting materials and reagents can be modified as desired to ensure synthesis of the intended compound. In addition, analogues can also be synthesized from the obtained compounds by usual procedures in synthetic organic chemistry which are known by a person skilled in the art.

The synthetic routes above mentioned can be modified as desired to give stereospecific compounds as well as mixtures of stereoisomers. It is possible to synthesize specific stereoisomers or specific mixtures by various methods including the use of stereospecific reagents or by introducing chiral centers into the compounds during the synthesis. It is possible to introduce one or more stereocenters during synthesis and also invert existing stereocenters. In addition, it is possible to separate stereoisomers once the compound has been synthesized by standard resolution techniques known to the skilled reader.

An important feature of the above described compounds of formula I is their bioactivity and in particular their cytotoxic activity.

With this invention we provide novel pharmaceutical compositions of compounds of general formula I that possess cytotoxic activity and their use as antitumor agents. Thus the present invention further provides pharmaceutical compositions comprising a compound of this invention, a pharmaceutically acceptable salt, tautomer, prodrug or stereoisomer thereof with a pharmaceutically acceptable carrier.

The term "carrier" refers to a diluent, adjuvant, excipient or vehicle with which the active ingredient is administered. Suitable pharmaceutical carriers are described in "Remington's Pharmaceutical Sciences" by E. W. Martin, 1995.

Examples of pharmaceutical compositions include any solid (tablets, pills, capsules, granules, etc.) or liquid (solutions, suspensions or emulsions) compositions for oral, topical or parenteral administration.

Administration of the compounds or compositions of the present invention may be by any suitable method, such as intravenous infusion, oral preparations, and intraperitoneal and intravenous administration. We prefer that infusion times of up to 24 hours are used, more preferably 1-12 hours, with 1-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or at different time.

Antitumoral activities of these compounds include, but are not limited to lung cancer, colon cancer, and breast cancer.

EXAMPLES

Example 1

Synthesis of Fragment 9

Scheme 1 provides an example of the synthesis of fragment 9.

Scheme 1

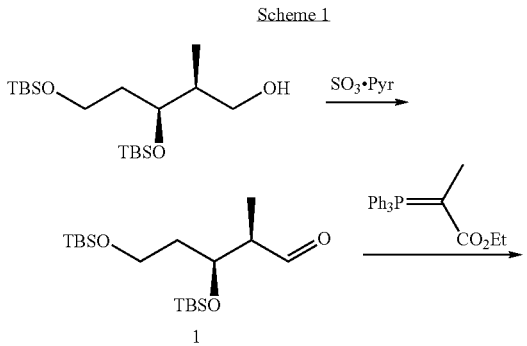

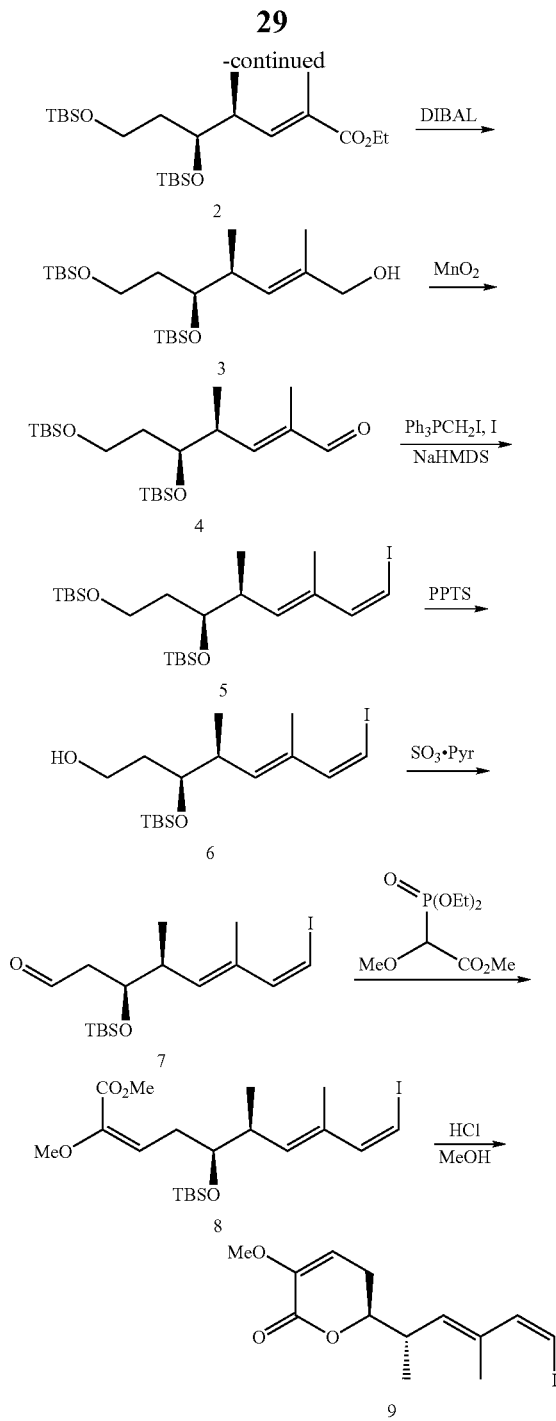

Synthesis of Intermediate 1

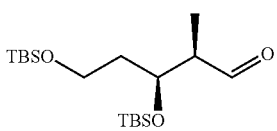 [SMILES: C[C@@H](C=O)[C@H](CCO[Si](C)(C)C(C)(C)C)O[Si](C)(C)C(C)(C)C]

To a 0° C. solution of (2S,3S)-3,5-Bis{[(tert-butyl)dimethylsilyl]oxy}-2-methylpentan-1-ol (P. Phukan, S. Sasmal and M. E. Maier Eur. J. Org. Chem. 2003, 1733-1740) (50 g, 0.14 mol) in a mixture of Dichloromethane/DMSO (331 mL/149 mL), Et₃N (96.1 mL, 0.69 mol) was added via addition funnel. After 10 min, SO₃.Pyr (54.8 g, 0.34 mol) was added portionwise and the solution was stirred for another 2 h at 0° C. Then, it was diluted with dichloromethane (800 ml) and quenched with HCl (0.5N, 800 mL). The organic layer was decanted, dried over MgSO₄ and concentrated in vacuo. Purification by column chromatography (hexane/EtOAc 100:0 to 10:1) afforded 45 g (yield: 90%) of aldehyde 1.

¹H NMR (CDCl₃, 300 MHz) δ: 9.79 (s, 1H), 4.30 (m, 1H), 3.65 (m, 2H), 2.51 (m, 1H), 1.69 (m, 2H), 1.04 (d, 3H, J=6.9 Hz), 0.85-0.88 (m, 18H), 0.03-0.07 (m, 12H).

¹³C NMR (CDCl₃, 75 MHz) δ: 205.4, 69.4, 59.6, 51.7, 37.5, 26.1, 26.0, 18.4, 18.2, 8.0, −4.3, −4.5, −5.2.

Synthesis of Intermediate 2

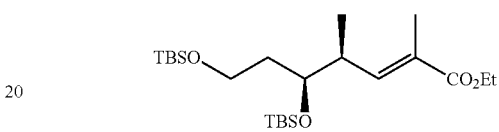

Over a solution of aldehyde 1 (45 g, 0.12 mol) in toluene (625 mL) Carboethoxyethylidene-triphenylphosphorane (113 g, 0.31 mol) was added and the mixture was heated at 60° C. over 17 h. Then, the solvent was removed under reduced pressure and the resulting oil was purified by column chromatography (hexane/EtOAc 100:0 to 10:1) affording 53.3 g (yield: 96%) of ester compound 2.

1H NMR (CDCl₃, 300 MHz) δ: 6.71 (dd, 1H, J=1.5, 10.2 Hz), 4.19 (m, 2H), 3.77 (m, 1H), 3.66 (m, 2H), 2.61 (m, 1H), 1.85 (d, 3H, J=1.5 Hz), 1.68 (m, 2H), 1.30 (t, 3H, J=7.2 Hz), 0.98 (d, 3H, 6.9 Hz), 0.90 (m, 18H), 0.05 (m, 12H).

¹³C NMR (CDCl₃, 75 MHz) δ: 168.3, 145.4, 126.7, 72.2, 60.4, 59.7, 38.4, 38.0, 25.9, 18.2, 18.1, 14.3, 14.3, 12.6, −4.4, −4.6, −5.4.

Synthesis of Intermediate 3

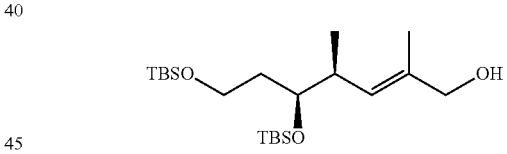

Over a −78° C. cooled solution of ester 2 (46.7 g, 0.105 mol) in anhydrous THF (525 mL) under argon atmosphere, Diisobutylaluminum hydride (DIBAL) 1M in toluene (231 mL, 0.231 mol) was added over a period of 10 min and the mixture was stirred at −78° C. After 4 hours the reaction was quenched with MeOH (10 mL) and a saturated solution of sodium potassium tartrate was added (800 mL) and diluted with EtOAc (1000 mL). This mixture was stirred for 2 h and then the organic layer was decanted. The aqueous residue was extracted with additional EtOAc (2×400 mL) and the combined organic layers were dried over anhydrous Na₂SO₄ and the solvent was evaporated. The resulting oil was purified by column chromatography (hexane/EtOAc 20:1 to 10:1) affording 32.5 g (yield: 77%) of alcohol 3.

¹H NMR (CDCl₃, 300 MHz) δ: 5.31 (d, 1H, J=9.6 Hz), 3.98 (m, 2H), 3.66 (m, 3H), 2.49 (m, 1H), 1.67 (s, 3H), 1.70-1.62 (m, 2H), 0.91 (d, 3H, J=6.9 Hz), 0.88 (m, 18H), 0.03 (m, 12H).

¹³C NMR (CDCl₃, 75 MHz) δ: 133.9, 129.8, 73.1, 69.1, 59.9, 37.8, 37.5, 25.9, 18.3, 18.1, 15.9, 13.9, −4.4, −4.4, −5.3.

Synthesis of Intermediate 4

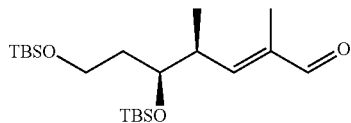 [SMILES: C/C(C=O)=C\[C@H](C)[C@H](CCO[Si](C)(C)C(C)(C)C)O[Si](C)(C)C(C)(C)C]

Over a solution of alcohol 3 (31.2 g, 77.5 mmol) in ethyl ether (387 mL) under argon atmosphere, $MnO_2$ (101 g, 1.16 mol) was added and the mixture was stirred at room temperature for 2 hours. This mixture was filtrated over a silica gel column eluting with EtOAc (3 L) and the resulting solution was dried under reduced pressure to afford 29.1 g (yield: 94%) of aldehyde 4.

$^1$H NMR (CDCl$_3$, 300 MHz) δ: 9.37 (s, 1H), 6.44 (d, 1H, J=9.6 Hz), 3.82 (dd, 1H, J=6.3, 10.8 Hz), 3.65 (m, 2H), 2.82 (m, 1H), 1.74 (s, 3H), 1.67 (m, 2H), 1.02 (d, 3H, J=6.9 Hz), 0.86 (s, 18H), 0.04-0.01 (m, 12H).

$^{13}$C NMR (CDCl$_3$, 75 MHz) δ: 195.4, 157.8, 138.3, 72.0, 59.5, 38.7, 37.5, 25.8, 18.2, 18.0, 14.3, 9.4, −4.4, −4.5, −5.4.

Synthesis of Intermediate 5

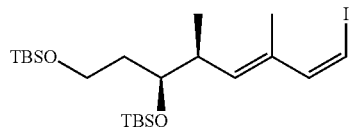 [SMILES: CC(/C=C\I)=C\[C@H](C)[C@H](CCO[Si](C)(C)C(C)(C)C)O[Si](C)(C)C(C)(C)C]

To a suspension of iodomethyl triphenylphosphonium iodide (Gilbert Stork, K Z. *Tetrahedron letters* 1989, 30(17), 2173) (96.3 g, 181.7 mmol) in anhydrous THF (727 mL) at 0° C., a 1M solution of sodium hexamethyldisilazane (NaHMDS) (181.7 mL, 181.7 mmol) was slowly added, via addition funnel, over a period of 10 min. After stirring for an additional 5 min, the solution was cooled to −78° C. and 1,3-Dimethyl-3,4,5,6-tetrahydro-2(1H)-pyrimidinone (DMPU) (43.9 mL, 363.4 mmol) was then added via cannula, followed by the addition of aldehyde 4 (29.1 g, 72.7 mmol) dissolved in anhydrous THF (727 mL). The temperature was kept at −78° C. while the reaction mixture was stirred for 2 hours. Hexane (1 L) was added and the resulting slurry was filtrated over celite and washed with additional hexane (3 L). The filtrate was evaporated under reduced pressure and the resulting oil was purified by column chromatography (hexane/EtOAc 100:0 to 20:1) affording 32 g (yield: 84%) of iodide 5.

$^1$H NMR (CDCl$_3$, 300 MHz) δ: 6.73 (d, 1H, J=8.4 Hz), 6.09 (dd, 1H, J=8.4, 1.2 Hz), 5.57 (dd, 1H, J=9.6, 1.2 Hz), 3.63-3.71 (m, 3H), 2.58 (m, 1H), 1.90 (s, 3H), 1.70 (m, 2H), 0.96 (dd, 3H, J=6.6, 1.2 Hz), 0.88 (s, 18H), 0.04 (m, 12H).

$^{13}$C NMR (CDCl$_3$, 75 MHz) δ: 142.3, 138.1, 131.8, 74.6, 72.9, 59.8, 38.1, 37.9, 26.0, 18.3, 18.2, 15.7, 15.7, −4.4, −5.2, −5.2.

Synthesis of Intermediate 6

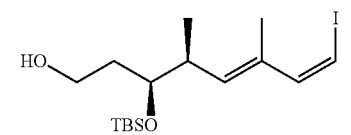 [SMILES: CC(/C=C\I)=C\[C@H](C)[C@H](CCO)O[Si](C)(C)C(C)(C)C]

To a solution of iodide 5 (12 g, 22.9 mmol) in EtOH (114 mL) pyridinium p-toluenesulfonate (PPTS) (2.01 g, 8.0 mmol) was added and the reaction mixture was stirred at room temperature for 25 hours. Then the solvent was removed under reduced pressure and the resulting oil was purified by column chromatography (hexane/EtOAc 10:1) affording 8.7 g (yield: 93%) of alcohol 6.

$^1$H NMR (CDCl$_3$, 300 MHz) δ: 6.69 (d, 1H, J=8.4 Hz), 6.12 (d, 1H, J=8.4 Hz), 5.47 (d, 1H, J=9.9 Hz), 3.67-3.87 (m, 4H), 2.71 (m, 1H), 1.89 (s, 3H), 1.73-1.86 (m, 2H), 1.01 (d, 3H, J=6.9 Hz), 0.91 (s, 9H), 0.087-0.115 (m, 6H).

$^{13}$C NMR (CDCl$_3$, 75 MHz) δ: 142.4, 136.4, 132.6, 75.8, 75.2, 60.0, 38.1, 36.4, 26.1, 18.2, 17.1, 16.0, −4.1, −4.2.

Synthesis of Intermediate 7

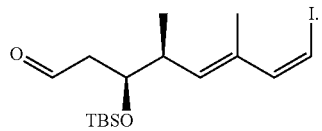 [SMILES: CC(/C=C\I)=C\[C@H](C)[C@H](CC=O)O[Si](C)(C)C(C)(C)C]

To a 0° C. solution of alcohol 6 (8.7 g, 21.2 mmol) in a mixture of Dichloromethane/DMSO (50.9 mL/22.9 mL), Et$_3$N (14.8 mL, 106 mmol) was added via addition funnel. After 10 min, SO$_3$.Pyr (8.43 g, 53.0 mol) was added portionwise and the solution was stirred for another 2 h at 0° C. Then, it was diluted with Dichloromethane (800 mL) and quenched with HCl (0.5N, 50 mL). The organic layer was decanted, dried over MgSO$_4$ and concentrated in vacuo. Purification by column chromatography (hexane/EtOAc 10:1) afforded 6.9 g (yield: 80%) of aldehyde 7.

$^1$H NMR (CDCl$_3$, 300 MHz) δ: 9.89 (t, 1H, J=1.5 Hz), 6.67 (d, 1H, J=8.4 Hz), 6.13 (d, 1H, J=8.4 Hz), 5.43 (d, 1H, J=10.2 Hz), 3.98 (m, 1H), 2.59-2.69 (m, 3H), 1.85 (s, 3H), 1.01 (d, 3H, J=6.6 Hz), 0.86 (s, 9H), 0.06 (s, 3H), 0.03 (s, 3H).

$^{13}$C NMR (CDCl$_3$, 75 MHz) δ: 201.8, 141.9, 135.2, 133.3, 76.3, 71.9, 49.3, 39.3, 25.8, 18.0, 16.7, 15.9, −4.4, −4.5.

Synthesis of Intermediate 8

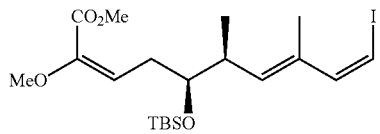 [SMILES: COC(=O)/C(=C\C[C@H](O[Si](C)(C)C(C)(C)C)[C@@H](C)/C=C(C)/C=C\I)OC]

To a solution of Diethyl(methoxy[methoxycarbonyl]methyl) phosphonate (5.51 g, 14.45 mmol) and 18-crown-6 (11.5 g, 43.34 mmol) in anhydrous THF (390 mL) stirred under argon atmosphere at −78° C., a 0.5 M Potassium bis(trimethylsilyl) amide solution (KHMDS) (43.34 mL, 21.67 mmol) was added dropwise. After 15 min aldehyde 7 (5.9 g, 14.45 mmol) in anhydrous THF was added dropwise over a period of 30 min and stirred at −78° C. for 90 min. Then, the reaction was quenched with a saturated NH$_4$Cl solution (200 mL), warmed to room temperature and diluted with Dichloromethane (1000 mL). The organic phase was dried over anhydrous Na$_2$SO$_4$ and evaporated at reduced pressure. Purification by column chromatography (hexane/Et$_2$O 20:1) afforded pure 4.2 g (59%) of (E)-8.

$^1$H NMR (CDCl$_3$, 300 MHz) δ: 6.70 (d, 1H, J=8.4 Hz), 6.08 (d, 1H, J=8.4 Hz), 5.47 (d, 1H, J=9.9 Hz), 5.37 (t, 1H, J=7.2 Hz), 3.78 (s, 3H), 3.60 (s, 3H), 3.60 (m, 1H), 2.79 (m, 1H), 2.52-2.67 (m, 2H), 1.83 (s, 3H), 0.99 (d, 3H, J=6.6 Hz), 0.89 (s, 9H), 0.05 (s, 3H), 0.04 (s, 3H).

$^{13}$C NMR (CDCl$_3$, 75 MHz) δ: 163.7, 145.9, 142.1, 137.3, 132.1, 110.4, 75.4, 74.8, 55.4, 51.9, 38.1, 32.3, 25.9, 18.1, 16.5, 15.7, −4.3, −4.5.

Synthesis of Intermediate 9

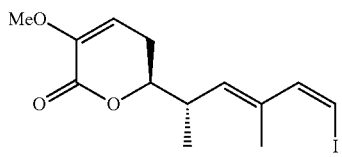 [SMILES: COC1=CC[C@@H]([C@@H](C)/C=C(C)/C=C\I)OC1=O]

To a solution of ester 8 (4.15 g, 8.39 mmol) in MeOH (125 mL) at room temperature, HCl 37% (1.04 mL) was added and the reaction mixture was stirred for 6 hours. Then the mixture was neutralized with a saturated aqueous solution of NaHCO$_3$ (pH 7-8) and the organic solvent was evaporated under reduced pressure. The resulting suspension was extracted with Dichloromethane (3×200 mL), dried and evaporated. Filtration by column chromatography (hexane/EtOAc 10:1 to 2:1) afforded 2.76 g (yield: 94%) of lactone 9.

$^1$H NMR (500 MHz, CDCl$_3$) δ: 6.68 (d, 1H, J=9.0 Hz), 6.20 (d, 1H, J=8.5 Hz), 5.63 (dd, 1H, J=2.5, 6.5 Hz), 5.43 (d, 1H, J=10.0 Hz), 4.19 (m, 1H), 3.65 (s, 3H), 2.84 (m, 1H), 2.55 (m, 1H), 2.43 (dc, 1H, J=3.0, 12.0, 15.0, 18.0 Hz), 1.87 (s, 3H), 1.16 (d, 3H, J=6.5 Hz).

$^{13}$C NMR (125 MHz, CDCl$_3$) δ: 161.6, 145.2, 141.8, 134.4, 132.7, 108.3, 81.7, 77.4, 55.4, 37.1, 26.6, 16.5, 16.1.

Example 2

Synthesis of Fragments 21 and 22

Scheme 2 provides an example of the synthesis of fragments 21 and 22.

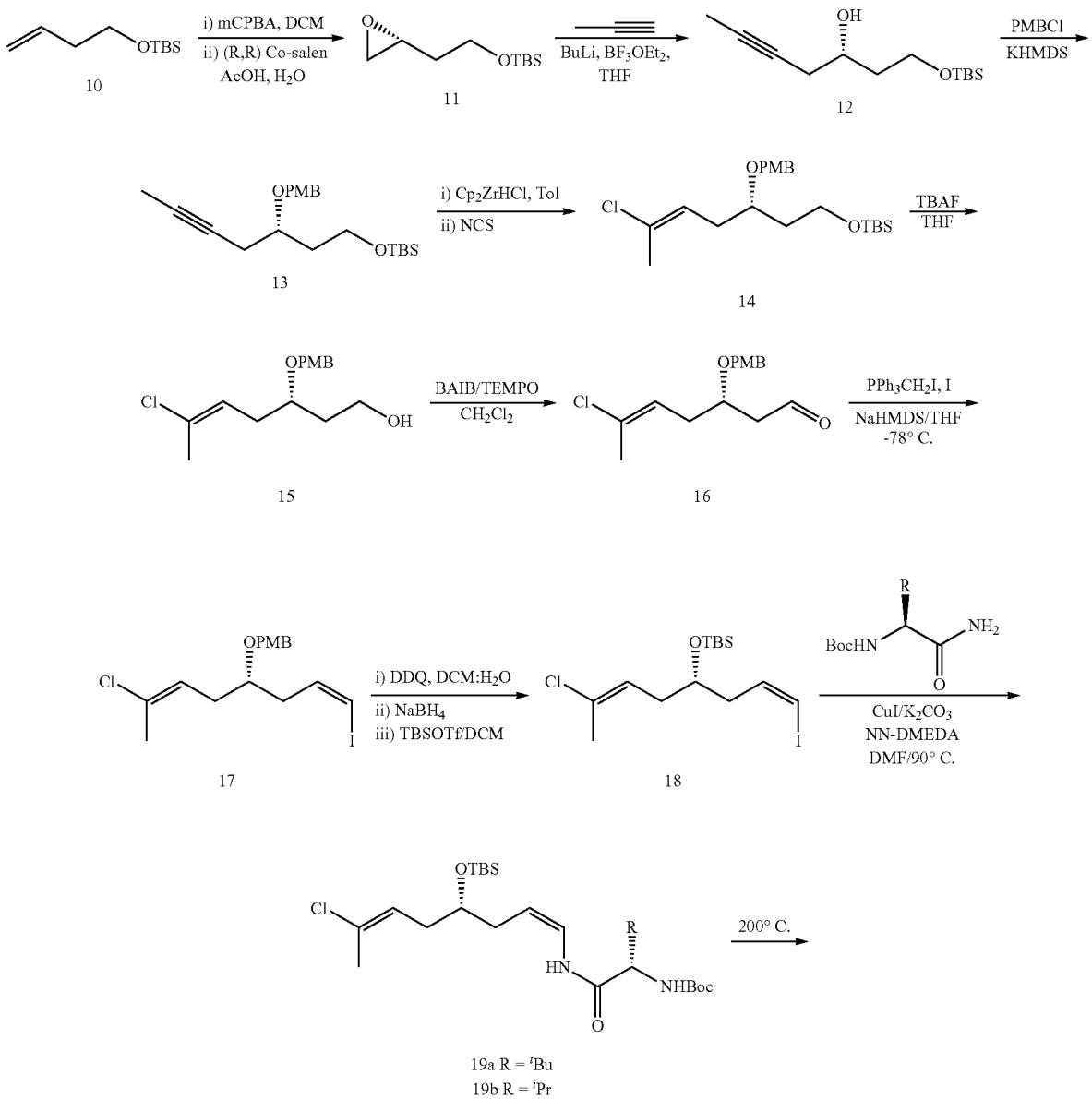

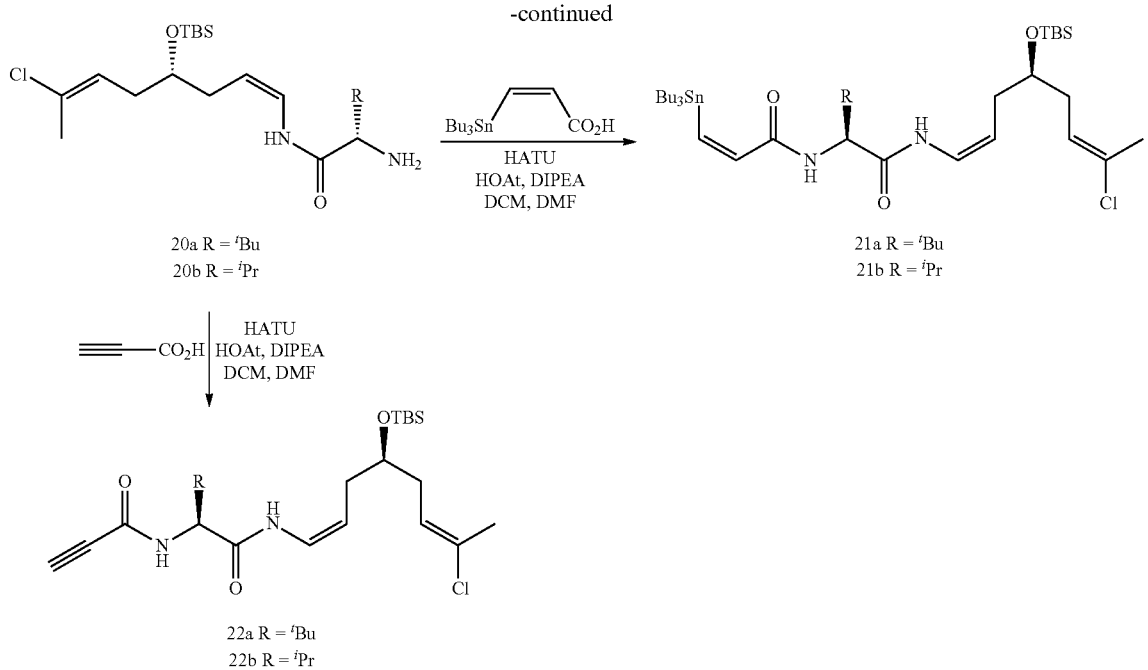

Synthesis of Intermediate 11

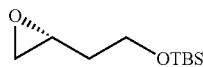 [SMILES: CC(C)(C)[Si](C)(C)OCC[C@@H]1CO1]

To a solution of intermediate 10 (72.3 g, 0.39 mol)) in anhydrous dichloromethane (DCM) (918 mL) at room temperature 3-Chloroperbenzoic acid (m-CPBA) (100 g, 0.58 mol) was added portionwise, and the mixture was stirred at room temperature for 18 h. The white precipitate was, quenched with saturated aqueous solution of $NaHCO_3$, extracted with DCM (3×250 mL) and washed again with saturated aqueous solution of $NaHCO_3$ (3×250 mL). The organic layers were combined, dried over anhydrous $Na_2SO_4$ and concentrated in vacuo. The resulting oil was purified on silica gel (Hexane-EtOAc; 15:1) to provide epoxide as a colourless oil (64.5 g, 82%). To a solution of racemic epoxide (30 g, 0.15 mol) in anhydrous THF (7.5 mL) (R,R)-(−)—N,N'-Bis(3,5-di-tert-butylsalicylidene)-1,2-cyclohexanediaminocobalt(II) [(R,R) Co(II) complex] (448 mg, 0.74 mmol) was added, followed by AcOH (0.14 mL). The solution was cooled to 0° C. and water (1.2 mL) was added dropwise. The reaction was allowed to warm to room temperature and stirred for 18 h. After that time the volatile materials were concentrated in vacuo and the crude was directly loaded on a silica gel column. Flash chromatography using Hexane/EtOAc (15:1 to 12:1) as eluent, provided chiral epoxide (+)-11 (13.6 g, yield: 46%) as a colourless oil.

$[\alpha]_D$=+14.1 (c 1, $CHCl_3$).

$^1$H NMR ($CDCl_3$, 300 MHz) δ: 3.74 (t, 2H, J=6.3 Hz), 3.01 (m, 1H), 2.74 (t, 1H, J=4.6 Hz), 2.48 (dd, 1H, J=5.1, 3.1 Hz), 1.70 (m, 2H), 0.87 (s, 9H), 0.04 (s, 6H).

$^{13}$C NMR ($CDCl_3$, 75 MHz) δ: 60.2, 50.2, 47.3, 36.1, 26.1, 18.4, −5.2.

Synthesis of Intermediate 12

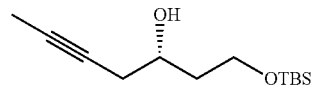 [SMILES: CC#CC[C@H](O)CCO[Si](C)(C)C(C)(C)C]

Propyne (10 mL, 0.176 mol) was condensed at −78° C. and dissolved in anhydrous THF (165 mL). n-Butyllithium (75.1 mL, 0.188 mol) was added dropwise under $N_2$ over 30 min, and the resultant white suspension was stirred for an additional 30 min at −78° C. A solution of (+) (R)-2-[2-(tert-butyldimethylsilyloxy)ethyl]oxirane 11 (23.7 g, 0.117 mol)) in anhydrous THF (125 mL) was then added dropwise followed by addition of $BF_3.OEt_2$ (22.1 mL, 0.176 mol). The mixture was stirred for 1 h at −78° C. and for an additional hour at 0° C. The reaction mixture was quenched with saturated aqueous solution of $NH_4Cl$ (150 mL) and extracted with $Et_2O$ (3×150 mL). The combined organic layers were dried over $Na_2SO_4$, filtered, and concentrated. Flash chromatography (hexane/EtOAc 10:1 to 1:1) provided alcohol 12 (22.7 g, yield: 80%) as a colourless oil.

$[\alpha]_D$=+5.6 (c 0.1, $CHCl_3$).

$^1$H NMR (500 MHz, $CDCl_3$) δ: 3.75-3.90 (m, 3H), 3.47 (d, 1H, J=2.7 Hz, OH), 2.34 (m, 2H), 1.79, (t, 3H, J=2.4 Hz), 1.75 (m, 2H), 0.89 (s, 9H), 0.07 (s, 6H).

$^{13}$C NMR (125 MHz, $CDCl_3$) δ: 77.8, 75.8, 70.7, 62.4, 37.6, 27.6, 26.1, 18.3, 3.7, −5.3, −5.4.

MS (ES) m/z 243.2 $[M+H]^+$, 265.2 $[M+Na]^+$

Synthesis of Intermediate 13

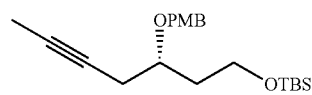

Over a solution of 12 (41.8 g, 0.173 mol) and 18-crown-6 ether (50.27 g, 0.190 mol) in anhydrous THF (1190 mL) at −78° C. under N$_2$ atmosphere, a 0.5N solution of KHMDS in toluene (380 mL, 0.190 mol) was added via addition funnel over a period of 30 min. The mixture was stirred at this temperature for 45 min, followed by addition of a solution of 4-methoxybenzyl chloride (PMBCl) (23.89 g, 0.176 mol) in anhydrous THF (100 mL). After 2 h at −78° C., the mixture was quenched with saturated aqueous solution of NH$_4$Cl (600 mL). The organic layer was separated and the aqueous phase was exhaustively extracted with EtOAc (3×500 mL). The combined organic layers were washed with saturated aqueous solution of NaCl, dried over anhydrous Na$_2$SO$_4$, filtered, and concentrated to afford 13 as yellow oil, which was used in the next steps without further purification (61.3 g, yield: 99%).

$^1$H NMR (CDCl$_3$, 300 MHz) δ: 7.25 (d, 2H, J=8.7 Hz), 6.90 (d, 2H, J=8.7 Hz), 4.45 (m, 2H), 3.80 (s, 3H), 3.65 (m, 3H), 2.40 (m, 2H), 1.82 (m, 2H), 1.79 (t, 3H, J=2.4 Hz), 0.92 (s, 9H), 0.05 (s, 6H).

Synthesis of Intermediate 14

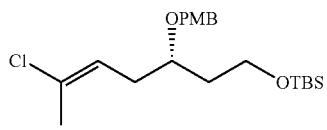

To a solution of 13 (61.3 g, 0.169 mol) in anhydrous toluene (2.1 L), under N$_2$ atmosphere and at 0° C. Schwartz's reagent (Bis(cyclopentadienyl)zirconium(IV) chloride hydride, Cp2ZrHCl) (130.3 g, 0.507 mol) was added and the reaction was stirred 5 min at room temperature. The reaction temperature was increased to 50° C. over a period of 20 min and stirred at 50° C. for 2.5 h. During this time the reaction solution turned of orange colour. The reaction was cooled to 0° C. and N-chlorosuccinimide (58.45 g, 0.440 mol) was added in one portion. Stirring was continued for 30 min at room temperature and the reaction was diluted with Hexane/EtOAc (95:5; 500 mL). Removing of the solid by filtration and evaporation of volatiles provided 14 as yellow oil which was used without further purification (15.1 g, yield: 86%).

[α]$_D$=+20.5 (c 1, CHCl$_3$).

$^1$H NMR (CDCl$_3$, 300 MHz) δ: 7.25 (d, 2H, J=8.7 Hz), 6.87 (d, 2H, J=8.7 Hz), 5.64 (td, 1H, J=7.8, 0.9 Hz), 4.45 (q, 2H, J=11.1 Hz), 3.80 (s, 3H), 3.70 (m, 2H), 3.62 (m, 1H), 2.27 (t, 2H, J=6.9 Hz), 2.03 (s, 3H), 1.70 (m, 2H), 0.89 (s, 9H), 0.05 (s, 6H).

$^{13}$C NMR (CDCl$_3$, 75 MHz)δ: 159.4, 130.9, 130.7, 129.6, 124.2, 114.0, 75.2, 71.4, 59.8, 55.5, 37.7, 33.8, 26.1, 21.2, 18.5, −5.1.

Synthesis of Intermediate 15

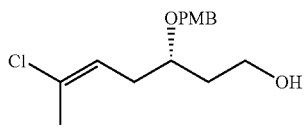

To a solution of 14 (23 g, 0.058 mol)) in anhydrous THF (288 mL) under N$_2$ and at 0° C. a solution of Tetrabutylammonium fluoride (TBAF) (115.3 mL, 0.115 mol) was added dropwise over a period of 20 min (the solution turned red). The reaction mixture was stirred at room temperature for 2 h, and then was quenched with saturated aqueous solution of NH$_4$Cl (200 mL). The layers were separated and the aqueous phase was exhaustively extracted with EtOAc (3×150 mL). The combined organic layers were dried over Na$_2$SO$_4$, filtered, and concentrated. Flash chromatography (hexane/EtOAc 4:1 to 1:1) provided 15 as a colourless oil (11.9 g, yield: 73%).

$^1$H NMR (CDCl$_3$, 300 MHz) δ: 7.25 (d, 2H, J=8.7 Hz), 6.86 (d, 2H, J=8.7 Hz), 5.62 (t, 1H, J=7.8 Hz), 4.45 (m, 2H), 3.80 (s, 3H), 3.70 (m, 3H), 2.35 (m, 2H), 2.03 (s, 3H), 1.75 (m, 2H).

Synthesis of Intermediate 16

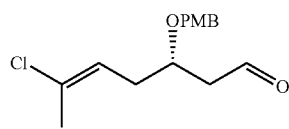

(Diacetoxyiodo)benzene (BAIB) (11.5 g, 35.7 mmol) was added to a solution of alcohol 15 (9.2 g, 32.4 mmol) and 2,2,6,6-Tetramethylpiperidine 1-oxyl (TEMPO) (515 mg, 3.3 mmol) in anhydrous dichloromethane (92 mL). The reaction mixture was stirred at room temperature for 20 h until the alcohol was no longer detectable (TLC), and then it was quenched with a saturated aqueous solution of NH$_4$Cl and extracted with DCM (3×100 mL). The combined organic phases were dried over anhydrous Na$_2$SO$_4$, filtered and concentrated. The residue was purified by flash chromatography (Hexane/EtOAc 4:1 to 1:1) to afford 16 as colourless oil (6.3 g, yield: 69%)

$^1$H NMR (CDCl$_3$, 300 MHz) δ: 9.78 (s, 1H), 7.25 (d, 2H, J=8.7 Hz), 6.85 (d, 2H, J=8.7 Hz), 5.64 (t, 1H, J=7.8 Hz), 4.45 (q, 2H, J=11.1 Hz), 4.02 (m, 1H), 3.80 (s, 3H), 2.60 (m, 2H), 2.35 (m, 2H), 2.03 (s, 3H).

$^{13}$C NMR (CDCl$_3$, 75 MHz) δ: 201, 159.6, 132.1, 130.1, 129.7, 122.8, 114.1, 73.3, 71.5, 55.5, 48.3, 33.5, 21.3.

Synthesis of Intermediate 17

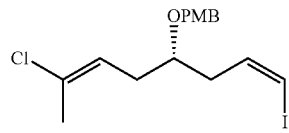

To a suspension of iodomethyltriphenylphosphonium iodide (16.6 g; 31 mmol) in anhydrous THF (126 mL), at room temperature, a 1M solution of NaHMDS in anhydrous THF (31.27 Ml, 31.27 mol) was slowly added. After stirring for 2 min, the yellow mixture was cooled to −78° C. and a solution of 16 (6.3 g, 22 mmol) in anhydrous THF (82 mL) was then added. The reaction mixture was stirred at −78° C. for 2 h, and at room temperature for 5 min, diluted with hexane and filtered through a plug of Celite®. The plug was rinsed with hexane, the combined filtrates were evaporated under reduced pressure and the resulting oil was purified by column chromatography (Hexane/EtOAc 12:1 to 8:1) affording 17 as a yellow oil (5.6 g, yield: 62%).

$^1$H NMR (CDCl$_3$, 300 MHz) δ: 7.25 (d, 2H, J=8.7 Hz), 6.85 (d, 2H, J=8.7 Hz), 6.25 (m, 2H) 5.64 (t, 1H, J=7.8 Hz), 4.42 (m, 2H), 3.80 (s, 3H), 3.55 (m, 1H), 2.40 (m, 2H), 2.25 (m, 2H), 2.03 (s, 3H).

Synthesis of Intermediate 18

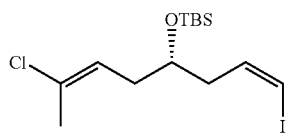 [SMILES: C/C(Cl)=C\C[C@@H](C/C=C\I)O[Si](C)(C)C(C)(C)C]

2,3-Dichloro-5,6-dicyano-p-benzoquinone (DDQ) (3.6 g, 16 mmol) was added to a solution of 17 (5 g, 12 mmol) in DCM-H$_2$O (20:1, 98 mL) under N$_2$ atmosphere at room temperature. After 1.5 h (TLC Hexane/EtOAc 4:1 showed no starting material) the reaction was quenched by pouring into Et$_2$O (200 mL) and washing with 1M NaOH (3×50 mL) and brine (50 mL). The organic phase was dried over anhydrous Na$_2$SO$_4$, filtered and concentrated. Chromatographic separation of p-methoxybenzaldehyde was facilitated by reduction to p-methoxybenzyl alcohol. Towards this end, a solution of the obtained residue in MeOH (98 mL) with NaBH$_4$ (0.60 g, 16 mmol) under N$_2$ atmosphere was maintained at room temperature for 1 h. The reaction mixture was then quenched by pouring into Et$_{20}$ (100 mL) and washing with 1 M HCl (40 mL) and brine (40 mL). The organic phase was dried over anhydrous Na$_2$SO$_4$, filtered and concentrated. The resulting oil was purified on silica gel (Hexane/EtOAc 10:1 to 4:1) to provide the secondary alcohol as colourless oil. (2.8 g, yield: 80%).

To a solution of secondary alcohol (2.8 g; 10 mmol) in anhydrous DCM (38 mL), under N$_2$ atmosphere and at 0° C., 2.6-lutidine (2.28 mL, 20 mmol) was added dropwise, followed by addition of tert-Butyldimethylsilyl trifluoromethanesulfonate (TBSOTf) (2.33 mL, 12 mmol). The reaction mixture was stirred for 2 h. At this point the crude was quenched with 0.5M HCl (25 mL) and extracted with DCM (2×25 mL). The combined organic layers were washed with a saturated aqueous solution of NaHCO$_3$ and brine. The organic phase was dried over Na$_2$SO$_4$, filtered, and concentrated. Flash chromatography (Hexane/EtOAc 100:1 to 20:1) provided 18 as a colourless oil (3.14 g, yield: 80%).

$^1$H NMR (CDCl$_3$, 300 MHz) δ: 6.25 (m, 2H) 5.64 (t, 1H, J=7.8 Hz), 3.82 (m, 1H), 2.38 (t, 2H, J=6.0 Hz), 2.20 (t, 2H, J=6.3 Hz), 2.03 (s, 3H), 0.86 (s, 9H), 0.05 (s, 6H).

$^{13}$C NMR (CDCl$_3$, 75 MHz) δ: 137.7, 130.9, 124.3, 84.6, 70.6, 42.5, 36.6, 25.9, 21.3, 18.2, −4.4.

Synthesis of Intermediate 19a

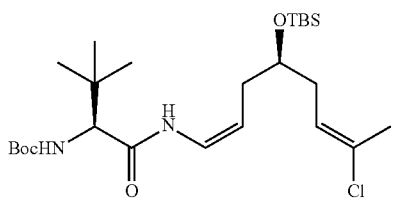 [SMILES: C/C(Cl)=C\C[C@@H](C/C=C\NC(=O)[C@@H](NC(=O)OC(C)(C)C)C(C)(C)C)O[Si](C)(C)C(C)(C)C]

A resealable Schlenk tube was charged with copper (I) iodide (148 mg, 0.78 mmol), potassium carbonate (1.076 g, 7.78 mmol) and Boc-tert-LeuCONH$_2$ (prepared following the procedure described in Pozdnev, V. F., *Tetrahedron Letters* 1995, 36, 7115-7118) (0.96 g, 4.15 mmol), evacuated and filled with N$_2$. N,N'-Dimethylethylenediamine (DMEDA) (0.166 mL, 1.55 mmol), vinyl iodide 18 (1.04 g, 2.59 mmol) and anhydrous DMF (15 mL) were added under N$_2$. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/ EtOAc, 20:1 to 15:1). Intermediate 19a (670 mg, yield: 53%) was obtained as an oil.

$^1$H NMR (CDCl$_3$, 300 MHz) δ: 7.72 (d, 1H, J=9.9 Hz), 6.70 (t, 1H, J=9.6 Hz), 5.54 (t, 1H, J=7.8 Hz), 5.35 (d, 1H, J=9.0 Hz), 4.76 (q, 1H, J=7.8 Hz), 3.89 (d, 1H, J=9.0 Hz), 3.73-3.68 (m, 1H), 2.12 (m, 4H), 1.98 (s, 3H), 1.40 (s, 9H), 0.97 (s, 9H), 0.84 (s, 9H), 0.02 (s, 3H), 0.01 (s, 3H).

$^{13}$C NMR (CDCl$_3$, 75 MHz) δ: 168.9, 156.0, 131.1, 123.9, 122.6, 108.2, 79.9, 71.6, 62.5, 36.5, 34.8, 33.8, 28.1, 26.7, 25.9, 21.2, 18.3, −4.3, −4.4.

Synthesis of Intermediate 19b

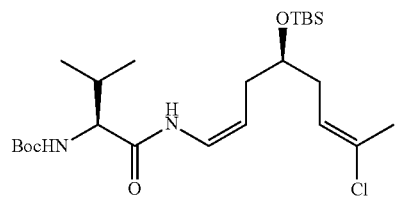 [SMILES: C/C(Cl)=C\C[C@@H](C/C=C\NC(=O)[C@@H](NC(=O)OC(C)(C)C)C(C)C)O[Si](C)(C)C(C)(C)C]

A resealable Schlenk tube was charged with copper (I) iodide (40.4 mg, 0.213 mmol), potassium carbonate (294 mg, 2.13 mmol) and Boc-Val-CONH$_2$ (prepared following the procedure described in Pozdnev, V. F., *Tetrahedron Letters* 1995, 36, 7115-7118) (230 mg, 1.06 mmol), evacuated and filled with N$_2$. N,N-Dimethylethylenediamine (45 µL, 0.426 mmol), vinyl iodide 18 (283 mg, 0.71 mmol) and anhydrous DMF (35 mL) were added under N$_2$. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/EtOAc, 7:1 to 3:1). Intermediate 19b (270 g, yield: 77%) was obtained as an oil.

$^1$H NMR (CDCl$_3$, 300 MHz) δ: 7.80 (d, 1H, J=9.3 Hz), 6.79-6.73 (m, 1H), 5.58 (t, 1H, J=7.5 Hz), 5.02 (br. s, 1H), 4.85-4.76 (m, 1H), 3.93 (dd, 1H, J=8.4, 6.0 Hz), 3.80-3.73 (m, 1H), 2.12-2.22 (m, 5H), 2.02 (s, 3H), 1.45 (s, 9H), 0.98 (d, 3H, J=6.9 Hz), 0.93 (d, 3H, J=6.9 Hz), 0.89 (s, 9H), 0.07 (s, 3H), 0.06 (s, 3H).

Synthesis of Intermediate 20a

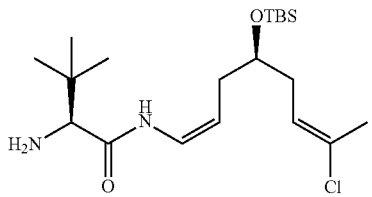 [SMILES: C/C(Cl)=C\C[C@@H](C/C=C\NC(=O)[C@@H](N)C(C)(C)C)O[Si](C)(C)C(C)(C)C]

A solution of amino protected derivative 19a (670 mg, 1.33 mmol) in ethylenglycol (30 mL) was heated at 200° C. for 15 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over anhydrous Na₂SO₄, filtrated and concentrated in vacuo to afford the primary amine 20a (510 mg, yield: 95%) as a yellow oil which was used without further purification.

¹H NMR (CDCl₃, 300 MHz) δ: 8.77 (d, 1H, J=9.9 Hz), 6.71 (t, 1H, J=9.6 Hz), 5.56 (t, 1H, J=7.8 Hz), 4.71 (m, 1H), 3.72 (m, 1H), 3.14 (s, 1H), 2.14 (m, 4H), 1.97 (s, 3H), 0.97 (s, 9H), 0.84 (s, 9H), 0.02 (s, 6H).

¹³C NMR (CDCl₃, 75 MHz) δ: 171.2, 131.0, 124.1, 122.5, 107.1, 71.5, 64.3, 36.2, 34.5, 33.8, 26.5, 26.0, 21.2, 18.2, −4.4, −4.5.

Synthesis of Intermediate 20b

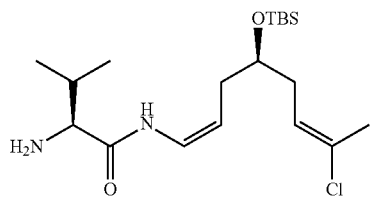 [SMILES: C/C(Cl)=C\C[C@@H](C/C=C\NC(=O)[C@@H](N)C(C)C)O[Si](C)(C)C(C)(C)C]

A solution of amino protected derivative 19b (255 mg, 0.52 mmol) in ethylenglycol (15 mL) was heated at 200° C. for 15 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over anhydrous Na₂SO₄, filtrated and concentrated in vacuo to afford the primary amine 20b (170 mg, yield 85%) as a yellow oil which was used without further purification.

¹H NMR (CDCl₃, 300 MHz) δ: 9.27 (d, 1H, J=10.2 Hz), 6.76 (dd, 1H, J=11.1, 9.6 Hz), 5.61 (t, 1H, J=7.8 Hz), 4.80-4.72 (m, 1H), 3.81-3.73 (m, 1H), 3.31 (d, 1H, J=3.6 Hz) 2.44-2.33 (m, 1H), 2.20-2.16 (m, 4H), 2.03 (s, 3H), 1.59 (br s, 2H), 1.00 (d, 3H, J=6.9 Hz), 0.89 (s, 9H), 0.82 (d, 3H, J=6.9 Hz), 0.05 (s, 6H).

¹³C NMR (CDCl₃, 75 MHz) δ: 172.1, 131.1, 124.1, 122.5, 107.4, 71.5, 60.2, 36.2, 33.7, 30.8, 26.0, 21.3, 20.0, 18.3, 16.1, −4.3, −4.4.

Synthesis of Intermediate 21a

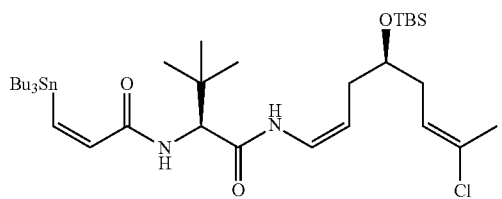

To a solution of amine 20a (918 mg, 2.27 mmol) in anhydrous DCM/DMF (10:1, 39.6 mL), a solution of (Z)-3-tributylstannylpropenoic acid (1028 mg, 2.84 mmol) in anhydrous DCM was added, under N₂ atmosphere, and then was cooled at 0° C. Diisopropylethylamine (DIPEA) (0.6 mL, 3.4 mmol), 1-Hydroxy-7-azabenzotriazole (HOAt) (310 mg, 2.27 mmol), and N,N,N',N'-Tetramethyl-O-(7-azabenzotriazol-1-yl)uronium hexafluorophosphate (HATU) (860 mg, 2.27 mmol) were added to the solution and after 30 min the cold bath was removed. The reaction mixture was stirred at room temperature for 2 h, quenched with a saturated aqueous solution of NH₄Cl, poured into water and extracted with DCM. The combined organic phases were dried over anhydrous Na₂SO₄, filtered and concentrated. The residue was purified by flash chromatography (Hexane/EtOAc 20:1 to 15:1) to give amide 21a (1.11 g; yield: 66%) as an oil.

¹H NMR (CDCl₃, 300 MHz) δ: 7.63 (d, 1H, J=10.5 Hz), 6.97 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, 1H, J=6.6 Hz), 4.83 (q, 1H, J=9.0 Hz), 4.41 (d, 1H, J=9.6 Hz) 3.76 (m, 1H), 2.17 (m, 4H), 2.01 (s, 3H), 1.45 (m, 6H), 1.25 (m, 8H), 1.0 (s, 9H), 0.88 (s, 9H), 0.84 (m, 13H), 0.06 (s, 6H).

Synthesis of Intermediate 21b

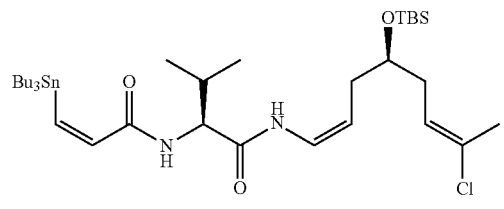

To a solution of amine 20b (170 mg, 0.437 mmol) in anhydrous DCM/DMF (10:1, 7.7 mL), a solution of (Z)-3-tributylstannylpropenoic acid (197.2 mg, 0.546 mmol) in anhydrous DCM was added, under N₂ atmosphere, and then was cooled at 0° C. DIPEA (0.11 mL, 0.655 mmol), HOAt (59.4 mg, 0.437 mmol), and HATU (166 mg, 0.437 mmol) were added to the solution and after 30 min the cold bath was removed. The reaction mixture was stirred at room temperature for 2 h, quenched with a saturated aqueous solution of NH₄Cl, poured into water and extracted with DCM. The combined organic phases were dried over anhydrous Na₂SO₄, filtered, and concentrated. The residue was purified by flash chromatography (Hexane/EtOAc 20:1 to 15:1) to give amide 21b (250 mg, yield: 78%) as a white foam.

¹H NMR (CDCl₃, 300 MHz) δ: 7.94 (d, 1H, J=10.8 Hz), 7.00 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, J=6.6 Hz, 1H), 4.83 (q, 1H, J=9.0 Hz), 4.41 (t, 1H, J=9.0 Hz), 3.76 (m, 1H), 2.17 (m, 4H), 2.01 (s, 3H), 1.45 (m, 7H), 1.25 (m, 8H), 0.88 (s, 9H), 0.84 (m, 19H), 0.06 (s, 6H).

¹³C NMR (CDCl₃, 75 MHz) δ: 169.2, 166.8, 153.8, 136.2, 131.1, 123.9, 122.6, 108.7, 71.6, 59.2, 36.5, 33.7, 31.4, 29.5, 27.6, 26.1, 21.3, 19.5, 18.5, 14.0, 11.8, −4.3, −4.4.

Synthesis of Intermediate 22a

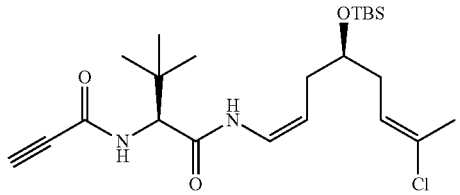 [SMILES: C#CC(=O)N[C@H](C(=O)N/C=C\C[C@H](C/C=C(\C)Cl)O[Si](C)(C)C(C)(C)C)C(C)(C)C]

To a solution of 20a (120 mg, 0.30 mmol) and propiolic acid (23 μL, 0.37 mmol) in anhydrous DCM/DMF 10:1 (4.2 mL) at 0° C., HATU (113 mg, 0.30 mmol), HOAt (40 mg, 0.30 mmol) and DIPEA (0.78 μL, 0.44 mmol) were added. The reaction was stirred at 0° C. for 30 min and 2 hours at room temperature. Then, the crude mixture was treated with a saturated aqueous solution of NH₄Cl and extracted with CH₂Cl₂. The combined filtrates were washed with H₂O. After drying and evaporating the solvent under reduced pressure the crude was purified by column chromatography (Ethyl acetate/hexanes mixture) to afford pure compound 22a (50 mg, yield: 40%).

$^1$H NMR (CDCl$_3$, 300 MHz) δ: 8.20 (d, 1H, J=10.2 Hz), 6.83 (d, 1H, J=9.6 Hz), 6.72 (t, 1H, J=9.3 Hz), 5.55 (t, 1H, J=6.9 Hz), 4.88 (q, 1H, J=8.7 Hz), 4.58 (d, 1H, J=9.6 Hz), 3.75 (m, 1H), 2.90 (s, 1H), 2.17 (m, 4H), 2.00 (s, 3H), 1.02 (s, 9H), 0.87 (s, 9H), 0.05 (s, 3H), 0.04 (s, 3H).

$^{13}$C NMR (CDCl3, 75 MHz) δ: 167.5, 152.1, 131.0, 124.1, 122.3, 109.4, 77.1, 74.8, 71.7, 60.9, 36.5, 35.7, 33.8, 26.7, 26.1, 21.2, 18.3, −4.3, −4.4.

Synthesis of Intermediate 22b

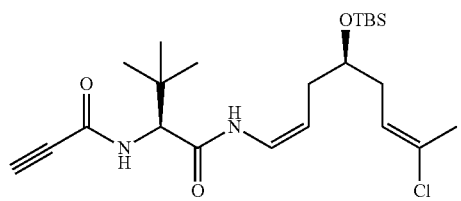 [SMILES: C#CC(=O)N[C@H](C(=O)N/C=C\C[C@H](C/C=C(\C)Cl)O[Si](C)(C)C(C)(C)C)C(C)(C)C]

To a solution of 20b (200 mg, 0.51 mmol) and propiolic acid (39 μL, 0.64 mmol) in anhydrous DCM/DMF 10:1 (8 mL) at 0° C., HATU (194 mg, 0.51 mmol), HOAt (69 mg, 0.51 mmol) and DIPEA (133 μL, 0.76 mmol) were added. The reaction was stirred at 0° C. for 30 min and 2 hours at room temperature. Then, the crude mixture was treated with a saturated aqueous solution of NH$_4$Cl and extracted with CH$_2$Cl$_2$. The combined filtrates were washed with H$_2$O. After drying and evaporating the solvent under reduced pressure the crude was purified by column chromatography (Ethyl acetate/hexanes mixture) to afford pure compound 22b (150 mg, yield: 67%).

$^1$H NMR (CDCl$_3$, 300 MHz) δ: 7.02 (d, 1H, J=11.4 Hz), 6.75 (dd, 1H, J=10.8, 9.0 Hz), 6.53 (d, 1H, J=10.2 Hz), 5.58 (dd, 1H, J=9.0, 7.8 Hz), 4.87 (q, 1H, J=7.8 Hz), 4.33 (dd, 1H, J=8.7, 6.3 Hz), 3.84-3.76 (m, 1H), 2.83 (s, 1H), 2.23-2.11 (m, 5H), 2.05-2.03 (m, 3H), 0.99 (d, 6H, J=6.9 Hz), 0.89 (s, 9H), 0.08 (s, 3H), 0.06 (s, 3H).

Example 3

Synthesis of Fragment 27

Scheme 3 provides an example of the synthesis of fragment 27.

Scheme 3

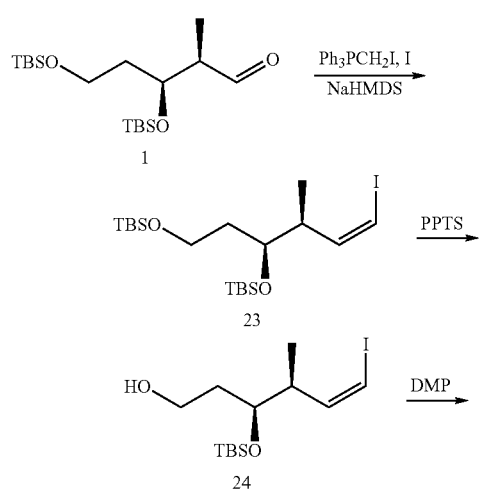

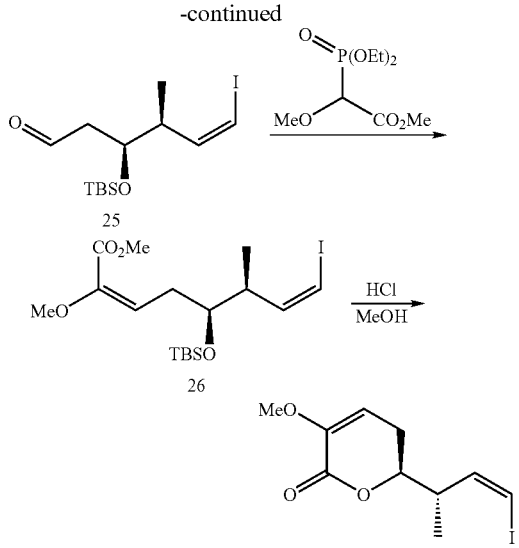

Synthesis of Intermediate 23

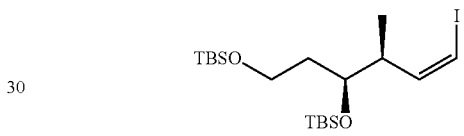

To a suspension of iodomethyl triphenylphosphonium iodide (Gilbert Stork, K Z. *Tetrahedron letters* 1989, 30(17), 2173) (6.6 g, 12.47 mmol) in anhydrous THF (50 mL) at 0° C., a 1M solution of sodium hexamethyldisilazane (NaHMDS) (12.5 mL, 12.47 mmol) was slowly added, via addition funnel, over a period of 10 min. After stirring for an additional 5 min, the solution was cooled to −78° C. and 1,3-Dimethyl-3,4,5,6-tetrahydro-2(1H)-pyrimidinone (DMPU) (3.02 mL, 24.95 mmol) was then added via cannula, followed by the addition of aldehyde 1 (1.80 g, 4.99 mmol) dissolved in anhydrous THF (50 mL). The temperature was kept at −78° C. while the reaction mixture was stirred for 2 hours. Hexane (200 mL) was added and the resulting slurry was filtrated over Celite® and washed with additional hexane (200 mL). The filtrate was evaporated under reduced pressure and the resulting oil was purified by column chromatography (hexane/EtOAc 100:0 to 20:1) affording 1.64 g (yield: 68%) of iodide 23.

$^1$H NMR (CDCl$_3$, 300 MHz) δ: 6.18-6.09 (m, 2H), 3.79 (m, 1H), 3.67 (m, 2H), 2.57 (m, 1H), 1.75-1.63 (m, 2H), 0.96 (d, 3H, J=6.9 Hz), 0.89 (m, 18H), 0.04 (m, 12H).

Synthesis of Intermediate 24

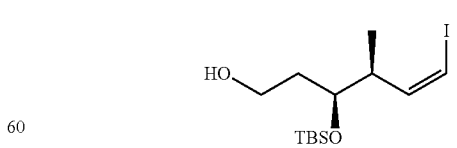

To a solution of iodide 23 (520 mg, 1.07 mmol) in EtOH (5.3 mL) pyridinium p-toluenesulfonate (PPTS) (94.4 mg, 0.38 mmol) was added and the reaction mixture was stirred at room temperature for 25 hours. Then the solvent was removed under reduced pressure and the resulting oil was purified by column chromatography (hexane/EtOAc 4:1) affording 380 mg (yield: 87%) of alcohol 24.

¹H NMR (CDCl₃, 300 MHz) δ: 6.20 (d, 1H, J=7.5 Hz), 6.08 (m, 1H), 3.87-3.72 (m, 3H), 2.69 (m, 1H), 1.85-1.80 (m, 1H), 1.71-1.65 (m, 1H), 0.99 (d, 3H, J=6.6 Hz), 0.90 (m, 9H), 0.09 (m, 6H)

Synthesis of Intermediate 25

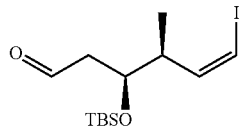 [SMILES: C[C@@H](/C=C\I)[C@H](CC=O)O[Si](C)(C)C(C)(C)C]

To a 0° C. solution of alcohol 24 (380 mg, 1.03 mmol) in anhydrous DCM (10.3 mL), Dess-Martin periodinane (870 mg, 2.05 mmol) was added. After 1 h, a saturated aqueous solution of NaHCO₃ (50 mL) was added and the organic layer was decanted, dried over anhydrous MgSO₄ and concentrated in vacuo. Purification by column chromatography (hexane/EtOAc 1:1) afforded 350 mg (yield: 93%) of aldehyde 25.

¹H NMR (CDCl₃, 300 MHz) δ: 9.82 (t, 1H, J=2.1 Hz), 6.26 (dd, 1H, J=0.6, 7.5 Hz), 6.05 (dd, 1H, J=1.5, 9.0 Hz), 4.14 (m, 1H), 2.68 (m, 1H), 2.58 (m, 2H), 1.01 (d, 3H, J=6.6 Hz), 0.87 (m, 9H), 0.07 (s, 3H), 0.03 (s, 3H).

Synthesis of Intermediate 26

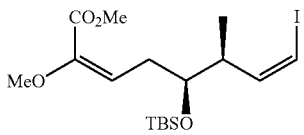 [SMILES: COC(=O)/C(=C\C[C@H](O[Si](C)(C)C(C)(C)C)[C@@H](C)/C=C\I)OC]

To a solution of Diethyl(methoxy[methoxycarbonyl]methyl)phosphonate (362 mg, 1.42 mmol) and 18-crown-6 (754 mg, 2.85 mmol) in anhydrous THF (27 mL) stirred under argon atmosphere at −78° C., a 0.5 M Potassium bis(trimethylsilyl)amide solution (KHMDS) (2.85 mL, 1.42 mmol) was added dropwise. After 15 min aldehyde 25 (350 mg, 0.95 mmol) in anhydrous THF (14 mL) was added dropwise over a period of 30 min and stirred at −78° C. for 90 min. Then, the reaction was quenched with a saturated NH₄Cl solution (20 mL), warmed to room temperature and diluted with Dichloromethane (50 mL). The organic phase was dried (anhydrous Na₂SO₄) and evaporated at reduced pressure. Purification by column chromatography (hexane/Et₂O 20:1) afforded pure 370 mg (86%) of (E)-26.

¹H NMR (CDCl₃, 300 MHz) δ: 6.12 (d, 1H, J=7.2 Hz), 6.03 (m, 1H), 5.32 (t, 1H, J=7.5 Hz), 3.78 (s, 3H), 3.77-3.70 (m, 1H), 3.63 (s, 3H), 2.69 (m, 2H), 2.58 (m, 1H), 0.97 (d, 3H, J=6.6 Hz), 0.88 (s, 9H), 0.04 (s, 6H).

Synthesis of Intermediate 27

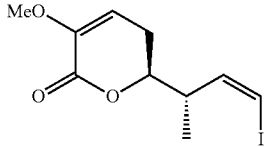

To a solution of ester 26 (95 mg, 0.21 mmol) in MeOH (3.15 mL) at room temperature, HCl 37% (26 µL) was added and the reaction mixture was stirred for 6 hours. Then the mixture was neutralized with a saturated aqueous solution of NaHCO₃ (pH 7-8) and the organic solvent was evaporated under reduced pressure. The resulting suspension was extracted with Dichloromethane (4×20 mL), dried and evaporated. Filtration by column chromatography (hexane/EtOAc 10:1 to 2:1) afforded 210 mg (yield: 84%) of lactone 27.

¹H NMR (CDCl₃, 300 MHz) δ: 6.32 (dd, 1H, J=0.6, 7.5 Hz), 6.08 (dd, 1H, J=1.5, 9.3 Hz), 5.62 (dd, 1H, J=3.0, 6.3 Hz), 4.28 (m, 1H), 3.63 (s, 3H), 2.84 (m, 1H), 2.54 (m, 1H), 2.34 (m, 1H), 1.13 (d, 3H, J=6.6 Hz).

Example 4

Synthesis of Fragment 30

Scheme 4 provides an example of the synthesis of fragment 30.

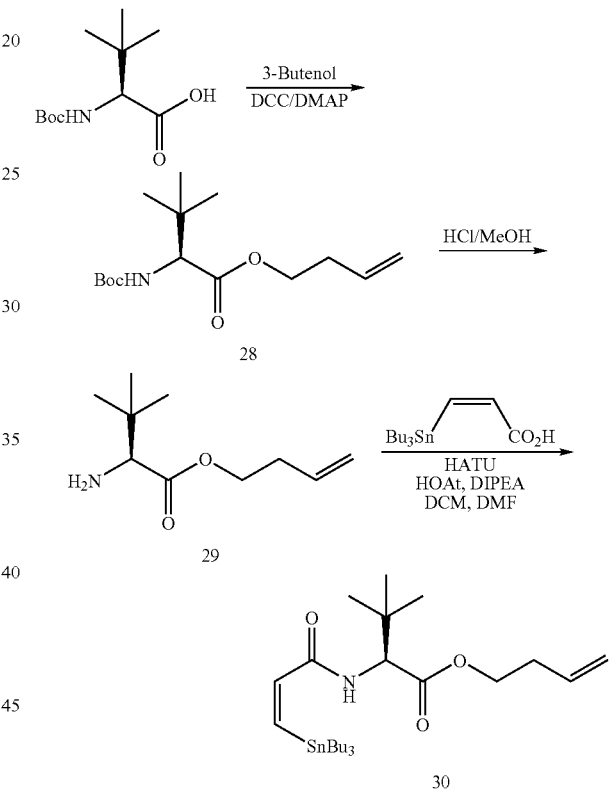

Scheme 4

Synthesis of Intermediate 28

To a mixture of L-Boc-tert-leucine (300 mg, 1.3 mmol) in anhydrous DCM (13 mL) and Dicyclohexylcarbodiimide (DCC) (295 mg, 1.43 mmol) at 0° C., under N₂, the 3-butenol (0.3 ml, 3.9 mmol) and the Dimethylaminopyridine (DMAP) (15.9 mg, 0.13 mmol) were added. The reaction mixture was stirred for 5 minutes at 0° C. and 4 hours at room temperature. The organic solvent was evaporated under reduced pressure and the resulting solid was purified by column chromatography (hexane/EtOAc 10:1) affording ester 28 (300 mg, yield: 81%).

$^1$H NMR (CDCl$_3$, 300 MHz) δ: 5.82-5.71 (m, 1H), 5.14-5.06 (m, 2H), 4.24-4.12 (m, 2H), 4.08 (d, 1H, J=9.8 Hz), 2.41 (q, 2H, J=6.7 Hz), 1.43 (s, 9H), 0.96 (s, 9H).

Synthesis of Intermediate 29

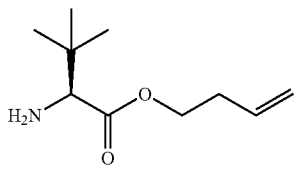

The solution of the ester 28 (180 mg, 0.63 mmol) in HCl.MeOH 1M (3.6 ml) was stirred at room temperature for 24 hours. The organic solvent was evaporated under reduced pressure and the resulting solid was diluted in DCM and washed with H$_2$O, the resulting organic phase was dried over anhydrous Na$_2$SO$_4$, filtered, and the solvent was evaporated affording 116 mg (yield: 100%) of 29.

$^1$H NMR (CDCl$_3$, 300 MHz) δ: 5.85-5.72 (m, 1H), 5.15-5.06 (m, 2H), 4.16 (t, 2H, J=6.7 Hz), 3.15 (s, 1H), 4.44-4.37 (m, 2H), 0.96 (s, 9H)

Synthesis of Intermediate 30

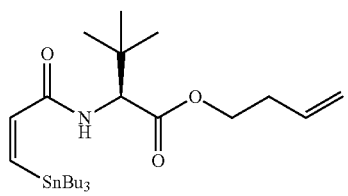

DIPEA (0.24 ml, 1.4 mmol), HOAt (123.3 mg, 0.9 mmol), and HATU (345 mg, 0.9 mmol) were added to a solution of 29 (168 mg, 0.9 mmol), and (Z)-3-tributylstannylpropenoic acid (393 mg, 1.2 mmol) in anhydrous DCM/DMF (10:1, 14 mL) at 0° C. under argon. After 2 hours, the cold bath was removed and the reaction mixture was stirred at room temperature for 1 hour, quenched with saturated aqueous solution of NH$_4$Cl, poured into water and extracted with DCM. The combined organic phases were dried over anhydrous Na$_2$SO$_4$, filtered and concentrated. The residue was purified by flash chromatography (Hexane/EtOAc 15:1 to 10:1) to give 30 (340 mg; yield: 72%).

$^1$H NMR (CDCl$_3$, 300 MHz) δ: 7.01 (d, 1H, J=12.3 Hz), 6.75 (d, 1H, J=12.3 Hz), 6.03 (d, 1H, J=9.73 Hz), 5.84-5.69 (m, 1H), 5.14-5.05 (m, 2H), 4.60 (d, 1H, J=9.76 Hz), 4.19-4.14 (m, 2H), 2.40 (q, 2H, J=6.70 Hz), 1.48-1.40 (m, 6H), 1.31-1.19 (m, 6H), 0.96 (s, 9H), 0.93-0.83 (m, 15H)

Example 5

Synthesis of Fragment 37

Scheme 5 provides the synthesis of the fragment 37.

Scheme 5

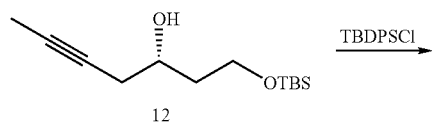

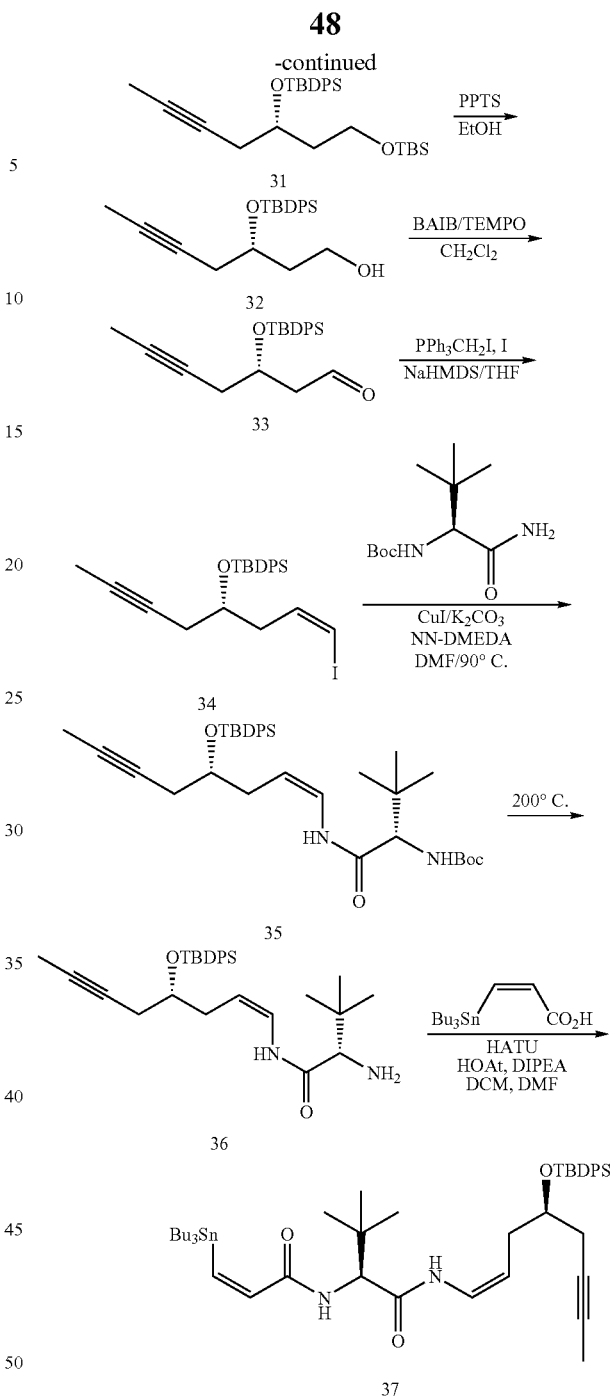

Synthesis of Intermediate 31

A solution of alcohol 12 (2.88 g, 11.9 mmol), tert-butyldiphenylsilyl chloride (4.39 mL, 16.89 mmol), and 4-(dimethylamino)pyridine (43.6 mg) in DMF (14 mL) was stirred overnight at room temperature. The mixture was diluted with water and extracted with Et$_{2O}$, and the organic phase was washed with brine, dried over anhydrous Na$_2$SO$_4$, filtered and concentrated. Flash chromatography (Hex/EtOAc, 95:1) gave the silyl ester 31 (5.3 g, 93%) as a colourless liquid.

$^1$H NMR (300 MHz, CDCl$_3$) δ: 7.70-7.66 (m, 4H), 7.40-7.34 (m, 6H), 3.99-3.95 (m, 1H), 3.70-3.62 (m, 2H), 2.23-2.22 (m, 2H), 1.84-1.81 (m, 2H), 1.69 (t, 3H, J=2.7 Hz), 1.05 (s, 9H), 0.84 (s, 9H), 0.01 (s, 6H).

$^{13}$C NMR (CDCl$_3$, 75 MHz) δ: 136.1, 134.6, 129.7, 127.8, 77.8, 76.2, 69.9, 60.1, 39.6, 27.5, 27.2, 26.2, 19.6, 18.5, 3.7, −5.1.

Synthesis of Intermediate 32

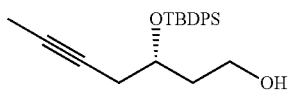

PPTS (837.7 mg, 3.33 mmol) was added in one portion to a solution of 31 (4 g, 8.33 mmol) in ethanol (80 mL). The reaction mixture was stirred at room temperature for 7 h and then was concentrated. The residue was diluted in DCM and washed with a saturated aqueous solution of NaHCO$_3$. The organic layer was extracted, dried over anhydrous Na$_2$SO$_4$, filtered and concentrated. Flash chromatography (Hex/EtOAc, 95:1) gave the silyl ester 32 (2.12 g, yield: 69%) as a colourless oil.

$^1$H NMR (500 MHz, CDCl$_3$) δ: 7.71-7.63 (m, 4H), 7.45-7.26 (m, 6H), 4.14-4.01 (m, 2H), 3.80-3.71 (m, 1H), 2.31-2.28 (m, 2H), 1.94-1.80 (m, 2H), 1.79 (t, 3H, J=2.4 Hz), 1.07 (s, 9H).

Synthesis of Intermediate 33

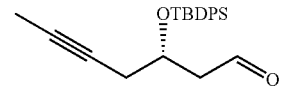

(Diacetoxyiodo)benzene (BAIB) (1.93 g, 6.00 mmol) was added to a solution of alcohol 32 (2.0 g, 5.46 mmol) and 2,2,6,6-Tetramethylpiperidine 1-oxyl (TEMPO) (85 mg, 0.55 mmol) in anhydrous dichloromethane (27 mL). The reaction mixture was stirred at room temperature for 18 h until the alcohol was no longer detectable (TLC), and then it was quenched with a saturated aqueous solution of NH$_4$Cl and extracted with DCM (3×500 mL). The combined organic phases were dried over anhydrous Na$_2$SO$_4$, filtered and concentrated. The residue was purified by flash chromatography (Hexane/EtOAc 20:1 to 10:1) to afford 33 as colourless oil (1.64 g; yield: 82%).

$^1$H NMR (CDCl$_3$, 300 MHz) δ: 9.72 (s, 1H), 7.71-7.63 (m, 4H), 7.45-7.26 (m, 6H), 4.29 (m, 1H), 2.65 (m, 2H), 2.33 (m, 2H), 1.70 (s, 3H), 1.04 (s, 9H).

Synthesis of Intermediate 34

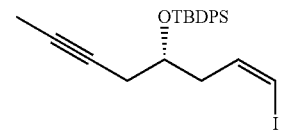

To a suspension of iodomethyltriphenylphosphonium iodide (3.14 g; 6.04 mmol) in anhydrous THF (60 mL), at room temperature, a 1M solution of NaHMDS in THF (6.0 mL) was slowly added. After stirring for 2 min, the yellow mixture was cooled to −78° C. and a solution of 33 (1.57 g, 4.31 mmol) in anhydrous THF (35 mL) was then added. The reaction mixture was stirred at −78° C. for 2 h, and at room temperature for 5 min, diluted with hexane and filtered through a plug of Celite®. The plug was rinsed with hexane and the combined filtrates were evaporated under reduced pressure and the resulting oil was purified by column chromatography (Hexane/EtOAc 50:1) affording 34 as yellow oil (1.31 g, yield: 62%).

$^1$H NMR (500 MHz, CDCl$_3$) δ: 7.70-7.66 (m, 4H), 7.44-7.34 (m, 6H), 6.27-6.24 (m, 2H), 3.99-3.95 (m, 1H), 2.47-2.41 (m, 2H), 2.27-2.23 (m, 2H), 1.71 (t, 3H, J=2.7 Hz), 1.07 (s, 9H).

Synthesis of Intermediate 35

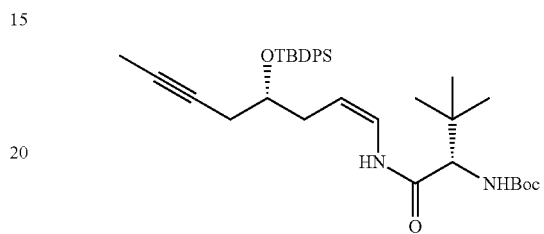

A resealable Schlenk tube was charged with copper (I) iodide (85.1 mg, 0.447 mmol), potassium carbonate (0.618 g, 4.47 mmol) and Boc-tert-LeuCONH$_2$ (prepared following the procedure described in Pozdnev, V. F., *Tetrahedron Letters* 1995, 36, 7115-7118) (0.514 g, 2.23 mmol), evacuated and filled with argon. N,N'-Dimethylethylenediamine (DMEDA) (0.095 mL, 0.89 mmol), vinyl iodide 34 (0.727 g, 1.49 mmol) and anhydrous DMF (11 mL) were added under argon. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/EtOAc, 20:1 to 15:1). Intermediate 35 (388 mg, yield: 44%) was obtained as an oil.

$^1$H NMR (300 MHz, CDCl$_3$) δ: 7.70-7.66 (m, 4H), 7.53 (d, 1H, J=10.5 Hz), 7.43-7.26 (m, 6H), 6.73 (t, 1H, J=9.6 Hz), 5.29 (m, 1H), 4.79 (m, 1H), 3.85-3.81 (m, 2H), 2.39-2.30 (m, 1H), 2.27-2.21 (m, 3H), 1.88 (s, 3H), 1.43 (s, 9H), 1.06 (s, 9H), 0.97 (s, 9H).

Synthesis of Intermediate 36

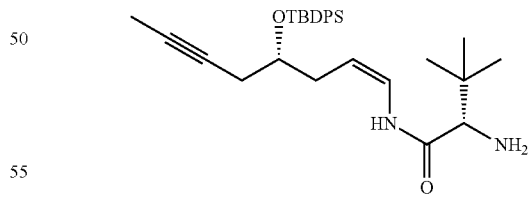

A solution of amino protected derivative 35 (288 mg, 0.487 mmol) in ethylenglycol (17 mL) was heated at 200° C. for 15 min. The reaction mixture was then cooled at room temperature, diluted with DCM, quenched with brine and poured into water. A few drops of 3M NaOH were added until the solution reached pH. 14 and then was extracted thoroughly with DCM. The combined organic phases were dried over anhydrous Na$_2$SO$_4$, filtrated and concentrated in vacuo to afford the primary amine 36 (165 mg, yield: 69%) as a yellow oil which was used without further purification.

$^1$H NMR (CDCl$_3$, 300 MHz) δ: 8.46 (d, 1H, J=11.1 Hz), 7.71-7.63 (m, 4H), 7.45-7.26 (m, 6H), 6.76 (t, 1H, J=10.2 Hz), 4.77 (q, 1H, J=10.2 Hz), 3.89 (m, 1H), 3.06 (s, 1H), 2.30 (m, 2H), 2.24 (m, 2H), 1.70 (s, 3H), 1.05 (s, 9H), 0.98 (s, 9H).

Synthesis of Intermediate 37

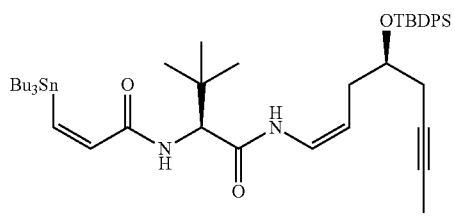

To a solution of amine 36 (221 mg, 0.450 mmol) in anhydrous DCM/DMF (4:1, 5 mL), a solution of (Z)-3-tributylstannyl-propenoic acid (195 mg, 0.54 mmol) in anhydrous DCM was added, under argon atmosphere, and then was cooled at 0° C. DIPEA (0.094 mL, 0.54 mmol), HOAt (73.5 mg, 0.54 mmol), and HATU (205 mg, 0.54 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over anhydrous Na$_2$SO$_4$, filtered, and concentrated. The residue was purified by flash chromatography (Hexane/EtOAc 20:1 to 15:1) to give amide 37 (288 mg, yield: 77%) as an oil.

$^1$H NMR (300 MHz, CDCl$_3$) δ: 7.70-7.66 (m, 4H), 7.61 (d, 1H, J=10.2 Hz), 7.42-7.38 (m, 6H), 7.02 (d, 1H, J=12.0 Hz), 6.77-6-70 (m, 2H), 6.28 (d, 1H, J=9.6 Hz), 4.82 (q, 1H, J=8.4 Hz), 4.36 (d, 1H, J=9.6 Hz), 3.89-3-86 (m, 1H), 2.39-2.24 (m, 4H), 1.94 (s, 3H), 1.50-1.41 (m, 6H), 1.30-1-23 (m, 6H), 1.07 (s, 9H), 0.92 (s, 9H), 0.92-0.84 (m, 15H).

Example 6

Synthesis of Fragment 40

Scheme 6 provides the synthesis of the fragment 40.

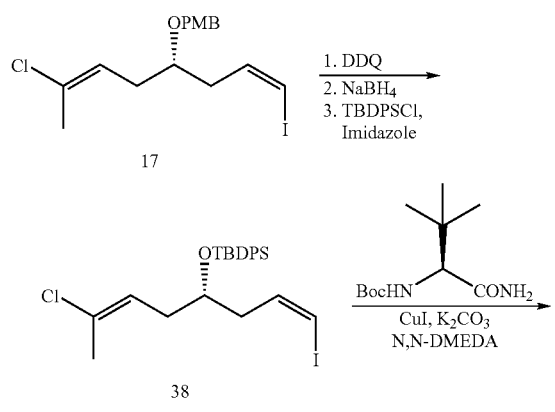

Scheme 6

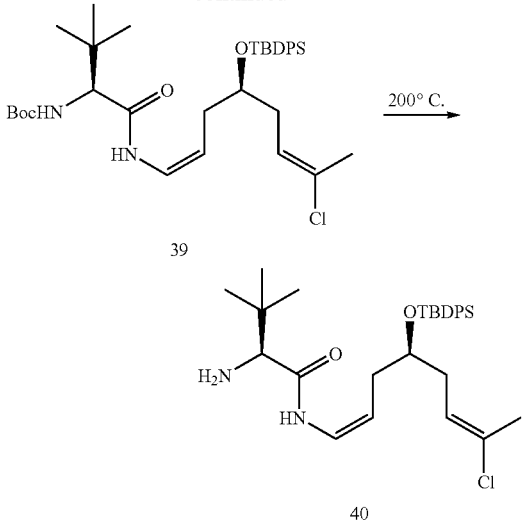

Synthesis of Intermediate 38

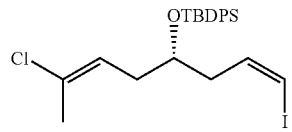

2,3-Dichloro-5,6-dicyano-p-benzoquinone (DDQ) (8.70 g, 38 mmol) was added to a solution of 17 (12 g; 30 mmol) in dichloromethane-H$_2$O (20:1) (236 mL) under Ar atmosphere at room temperature. After 1:30 h (TLC Hexane/EtOAc 4:1 showed no starting material) the reaction was quenched by pouring into Et$_{2O}$ (400 mL) and washing with aqueous 1M NaOH (3×200 mL) and brine (200 mL). The organic phase was dried over anhydrous Na$_2$SO$_4$, filtered and concentrated. Chromatographic separation of p-methoxybenzaldehyde was facilitated by reduction to p-methoxybenzyl alcohol. Towards this end, a solution of the residue obtained in MeOH (236 mL) with NaBH$_4$ (1.5 g, 38 mmol) under Ar atmosphere was maintained at room temperature for 1 h. The reaction mixture was then quenched by pouring into Et$_{2O}$ (400 mL) and washing with aqueous 1 M HCl (200 mL) and brine (200 mL). The organic phase was dried over anhydrous Na$_2$SO$_4$, filtered and concentrated. The resulting oil was purified on silica gel (Hexane/EtOAc 10:1 to 4:1) to provide the secondary alcohol as colourless oil. (6 g, 73% yield).

To a solution of secondary alcohol (6 g; 21 mmol) in anhydrous DMF (25 mL), under Ar atmosphere and at room temperature, imidazole (3.3 g, 48.6 mmol) was added in portions, followed by addition of tert-Butyldiphenylsilyl chloride (TBDPSCl) (7.6 mL, 29.3 mmol) and DMAP (77 mg, 0.63 mmol). The mixture was stirred overnight and at this point the crude was quenched with water (30 mL) and extracted with Et$_2$O (3×30 mL). The combined organic layers were washed thoroughly with water and brine. The organic phase was dried over anhydrous Na$_2$SO$_4$, filtered, and concentrated. Flash chromatography (Hexane/EtOAc 100:1 to 30:1) provided 38 (9.6 g, 92%) as a colourless oil.

$^1$H NMR (CDCl$_3$, 300 MHz) δ: 7.67 (m, 4H), 7.45-7.37 (m, 6H), 6.25 (m, 2H), 5.51 (t, 1H, J=7.8 Hz), 3.89 (m, 1H), 2.30 (t, 2H, J=5.5 Hz), 2.14 (t, 2H, J=6.4 Hz), 1.85 (s, 3H), 1.07 (s, 9H).

Synthesis of Intermediate 39

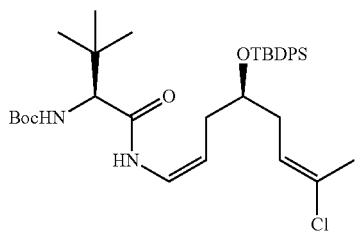

A resealable Schlenk tube was charged with copper (I) iodide (1.05 g, 5.54 mmol), potassium carbonate (7.65 g, 55.4 mmol) and Boc-tert-LeuCONH$_2$ (prepared following the procedure described in Pozdnev, V. F., *Tetrahedron Letters* 1995, 36, 7115-7118) (6.8 g, 29.6 mmol), evacuated and filled with argon. N,N'-Dimethylethylenediamine (DMEDA) (1.18 mL, 11.1 mmol), vinyl iodide 38 (9.7 g, 18.5 mmol) and anhydrous DMF (92 mL) were added under argon. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/EtOAc, 20:1 to 15:1) affording compound 39 (5.8 g, yield 51%) as a white solid.

$^1$H NMR (CDCl$_3$, 300 MHz) δ: 7.67 (m, 4H), 7.47-7.37 (m, 6H), 7.02 (d, 1H, J=10.2 Hz), 6.67 (t, 1H, J=9.4 Hz), 5.51 (t, 1H, J=7.3 Hz), 5.23 (d, 1H, J=8.4 Hz), 4.72 (q, 1H, J=8.1 Hz), 3.81 (m, 2H), 2.18-2.04 (m, 4H), 1.86 (s, 3H), 1.42 (s, 9H), 1.05 (s, 9H), 0.97 (s, 9H).

Synthesis of Compound 40

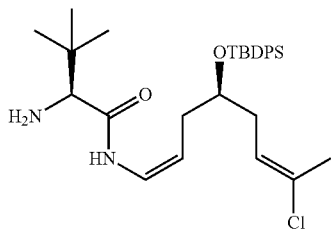

A solution of amino protected derivative 39 (4.75 g, 7.6 mmol) in ethylene-glycol (140 mL) was heated at 200° C. for 15 min. The reaction mixture was then cooled at room temperature, diluted with dichlorometane, quenched with brine and poured into water. A few drops of 3M NaOH were added until the solution reached pH 14 and then was extracted thoroughly with dichloromethane. The combined organic phases were washed with water, dried over anhydrous Na$_2$SO$_4$, filtrated and concentrated under reduced pressure to afford the primary amine 40 (3.8 g, 95% yield) as a yellow oil which was used without further purification.

$^1$H NMR (CDCl$_3$, 300 MHz) δ: 8.66 (d, 1H, J=10.5 Hz), 7.66 (m, 4H), 7.47-7.33 (m, 6H), 6.71 (t, 1H, J=9.3 Hz), 5.53 (t, 1H, J=8.3 Hz), 4.72 (q, 1H, J=8.4 Hz), 3.83 (m, 1H), 3.19 (s, 1H), 2.22-2.05 (m, 4H), 1.83 (s, 3H), 1.05 (s, 9H), 0.99 (s, 9H).

Example 7

Synthesis of Fragment 45

Scheme 7 provides an example of the synthesis of fragment 45.

Scheme 7

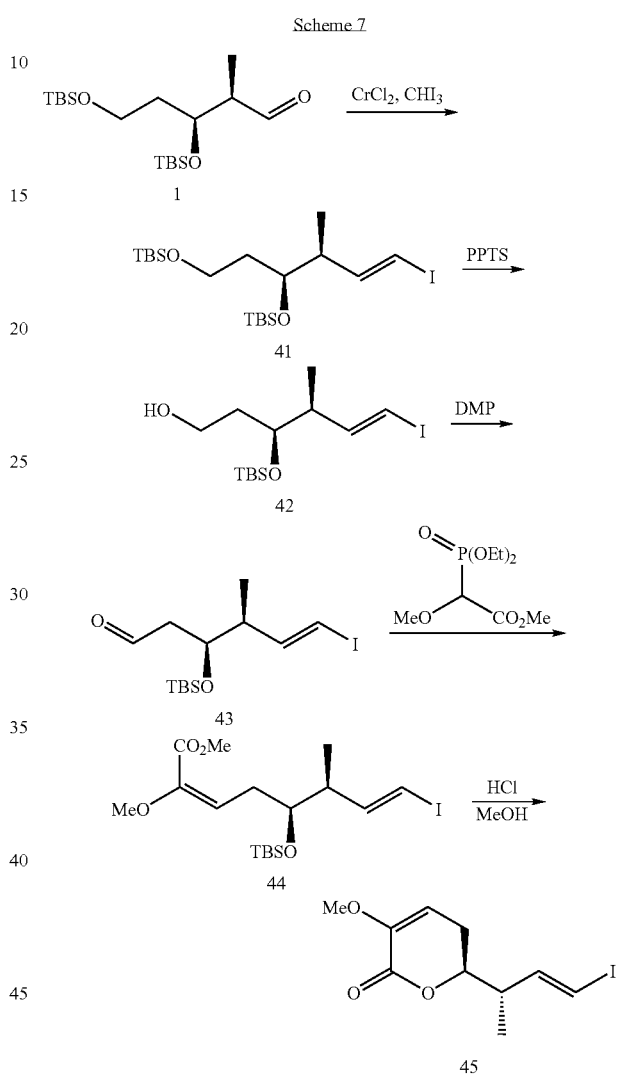

Synthesis of Intermediate 41

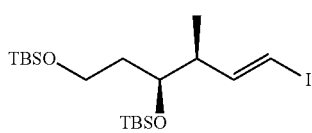 [SMILES: C[C@@H](/C=C/I)[C@H](CCO[Si](C)(C)C(C)(C)C)O[Si](C)(C)C(C)(C)C]

To a solution of anhydrous CrCl$_2$ (2.03 g, 16.55 mmol) in anhydrous THF (30 mL) at 0° C. was added a solution of the aldehyde 1 (0.995 g, 2.76 mmol) and iodoform (2.17 g, 5.52 mmol) in anhydrous THF (10 mL). After 4 hours of stirring at 23° C., the mixture was diluted with Et$_{2O}$ and filtered through Celite®. The filtrated was concentrated to afford a residue which was purified by flash chromatography on silica (hexane/dichloromethane from 50:1 to 5:1) to give vinyl iodide 41 (0.79 g, 57% yield) as a slightly yellow oil.

¹H NMR (CDCl₃, 300 MHz) δ: 6.58 (dd, 1H, J=14.5, 6.7 Hz), 5.98 (dd, 1H, J=14.5, 1.3 Hz), 3.76-3.70 (m, 1H), 3.67-3.59 (m, 2H), 2.37-2.32 (m, 1H), 1.62-1.53 (m, 2H), 0.96 (d, 3H, J=7.2 Hz), 0.89 (m, 18H), 0.04 (m, 12H).

Synthesis of Intermediate 42

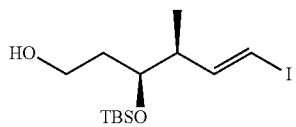 [SMILES: C[C@@H](/C=C/I)[C@H](CCO)O[Si](C)(C)C(C)(C)C]

To a solution of iodide 41 (786 mg, 1.58 mmol) in EtOH (15 mL) pyridinium p-toluenesulfonate (PPTS) (139 mg, 0.55 mmol) was added and the reaction mixture was stirred at room temperature for 25 hours. Then the solvent was removed under reduced pressure and the resulting oil was purified by column chromatography (hexane/EtOAc 4:1) affording 379.7 mg (63% yield) of alcohol 42 as colourless oil.

1H NMR (CDCl₃, 300 MHz) δ: 6.56 (dd, 1H, J=14.5, 6.7 Hz), 6.01 (dd, 1H, J=14.5, 1.3 Hz), 3.78-3.3.69 (m, 3H), 2.45-2.39 (m, 1H), 1.87-1.83 (m, 1H), 1.71-1.59 (m, 2H), 1.00 (d, 3H, J=6.6 Hz), 0.90 (s, 9H), 0.09 (s, 3H), 0.07 (s, 3H).

Synthesis of Intermediate 43

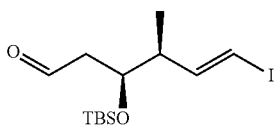 [SMILES: C[C@@H](/C=C/I)[C@H](CC=O)O[Si](C)(C)C(C)(C)C]

To a 0° C. solution of alcohol 42 (389 mg, 1.01 mmol) in anhydrous DCM (10 mL), Dess-Martin periodinane (644 mg, 1.52 mmol) was added. After 1 hour stirring at 0° C. and 30 min at 23° C. the reaction mixture was quenched with a saturated aqueous solution of NaHCO₃. The organic layer was decanted, dried over anhydrous Na₂SO₄ and concentrated under reduced pressure. Purification by column chromatography (hexane/EtOAc 20:1 to 2:1) afforded 349.3 mg (90% yield) of aldehyde 43 as a colourless oil.

¹H NMR (CDCl₃, 300 MHz) δ: 9.77 (t, 1H, J=2.1 Hz), 6.52 (dd, 1H, J=14.7, 7.5 Hz), 6.05 (dd, 1H, J=14.7, 1.2 Hz), 4.12-4.07 (m, 1H), 2.52-2.47 (m, 2H), 2.2.43-2.36 (m, 1H), 0.98 (d, 3H, J=7.2 Hz), 0.87 (s, 9H), 0.07 (s, 3H), 0.03 (s, 3H).

Synthesis of Intermediate 44

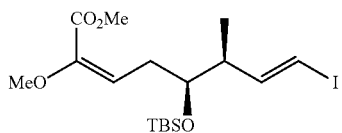 [SMILES: COC(=O)/C(=C\C[C@H](O[Si](C)(C)C(C)(C)C)[C@@H](C)/C=C/I)OC]

To a solution of Diethyl(methoxy[methoxycarbonyl]methyl) phosphonate (348.4 mg, 1.37 mmol) and 18-crown-6 (722.3 mg, 2.73 mmol) in anhydrous THF (13 mL) stirred under argon atmosphere at −78° C., a 0.5 M Potassium bis(trimethylsilyl)amide (KHMDS) solution in toluene (2.74 mL, 1.37 mmol) was added dropwise. After 15 min aldehyde 43 (349.4 mg, 0.91 mmol) in anhydrous THF (9 mL) was added dropwise over a period of 30 min and stirred at −78° C. for 90 min. Then, the reaction was quenched with a saturated aqueous solution of NH₄Cl (20 mL), warmed to room temperature and diluted with dichloromethane (50 mL). The organic phase was dried (anhydrous Na₂SO₄) and evaporated under reduced pressure. Purification by column chromatography (hexane/EtOAc 30:1 to 5:1) afforded 410. mg (99% yield) of 44 as a mixture E/Z (regioselectivity>5:1 determined by ¹H NMR).

¹H NMR (CDCl₃, 300 MHz) for (2E, 7E)-44 δ: 6.51 (dd, 1H, J=14.4, 7.8 Hz), 5.97 (dd, 1H, J=14.4, 1.2 Hz), 5.29 (t, 1H, J=7.7 Hz), 3.82 (s, 3H), 3.77-3.70 (m, 1H), 3.60 (s, 3H), 2.65-2.61 (m, 2H), 2.39-2.21 (m, 1H), 1.00 (d, 3H, J=6.9 Hz), 0.89 (s, 9H), 0.04 (s, 6H).

Synthesis of Intermediate 45

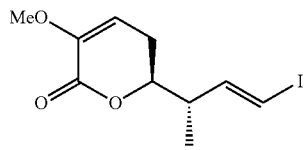

To a solution of ester 44 (410.9 mg, 0.90 mmol) in MeOH (13.5 mL) at room temperature, aqueous HCl 37% (160 μL) was added and the reaction mixture was stirred for 6 hours. Then the mixture was neutralized with a saturated aqueous solution of NaHCO₃ (pH 7-8) and the organic solvent was evaporated under reduced pressure. The resulting suspension was extracted with dichloromethane (4×20 mL), dried and evaporated. The crude was purified by column chromatography (hexane/EtOAc 10:1 to 2:1) to yield 192 mg (69% yield) of lactone 45 as a white solid.

¹H NMR (CDCl₃, 300 MHz) δ: 6.32 (dd, 1H, J=14.7, 8.4 Hz), 6.21 (dd, 1H, J=14.7, 1.2 Hz), 5.62 (dd, 1H, J=6.6, 2.7 Hz), 4.27-4.19 (m, 1H), 3.64 (s, 3H), 2.61-2.54 (m, 1H), 2.43-2.34 (m, 2H), 1.14 (d, 3H, J=6.9 Hz).

MS (ES) [m/z]=331.1 [M+Na]⁺.

Example 8

Synthesis of Fragment 51

Scheme 8 provides an example of the synthesis of fragment 51.

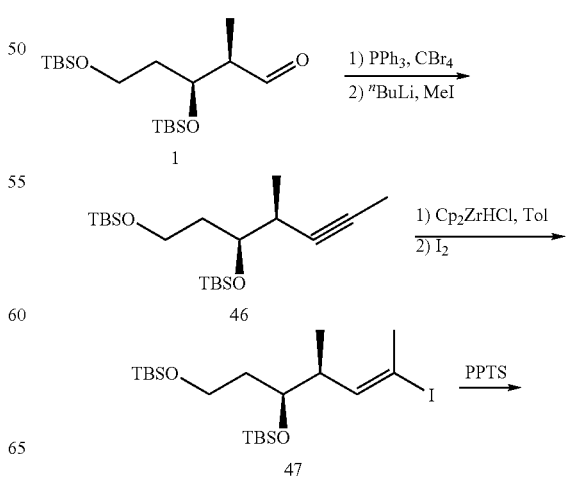

Scheme 8

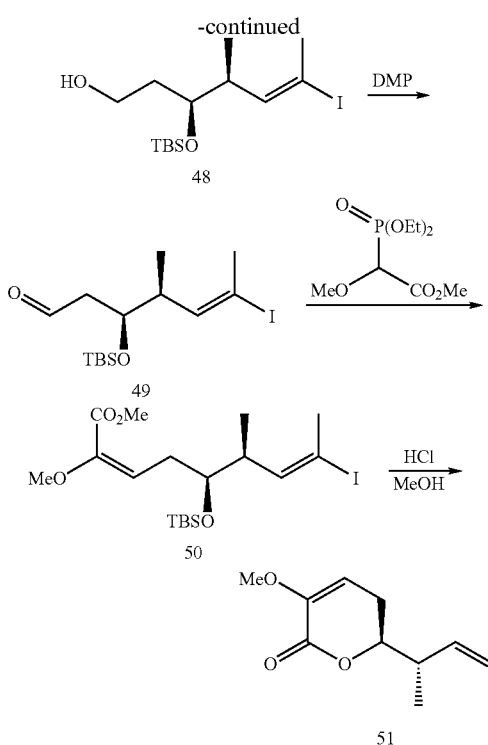

Synthesis of Intermediate 46

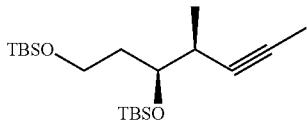 [SMILES: CC#C[C@H](C)[C@H](CCO[Si](C)(C)C(C)(C)C)O[Si](C)(C)C(C)(C)C]

To a solution of carbon tetrabromide (8.74 g, 26.35 mmol) in dry dichloromethane (26 mL) was added dropwise a solution of triphenylphosphine (1.38 g, 52.69 mmol) in anhydrous DCM (50 mL) at 0° C. The dark yellow solution was cooled to −78° C. and aldehyde 1 (4.75 g, 13.2 mmol) in anhydrous DCM (13 mL) was added quickly. The resulting mixture was stirred at −78° C. (30 min) and at 0° C. (10 min). The reaction was diluted with Et$_2$O and then washed with brine. The aqueous layer was extracted with Et$_2$O and the organic layers were combined, dried, filtered and evaporated under reduced pressure. Purification by flash chromatography (hexane/dichloromethane 10:1) afforded 4.37 g (66% yield) of vinyl dibromide as colourless oil. To a solution of the dibromoolefin in anhydrous THF (80 mL) was added dropwise a 2.5 M solution of n-butyllithium in hexane (7.03 mL) at −78° C. The reaction was warmed to −25° C. and stirred for 1 h. The reaction was cooled back down to −78° C. and methyl iodide (0.55 mL, 8.79 mmol) in anhydrous THF (9 mL) was added dropwise. The resulting mixture was allowed to warm to room temperature and stir for an additional 1 h. The reaction was quenched with a saturated aqueous solution of NH$_4$Cl then diluted with Et$_2$O. The organic layer was dried, filtered and evaporated under reduced pressure. Purification by flash chromatography (hexane/dichloromethane from 50:1 to 5:1) afforded 2.77 mg (89% yield) of alkyne 46 as a colourless oil.

$^1$H NMR (CDCl$_3$, 300 MHz) δ: 3.74-3.66 (m, 3H), 2.49-2.46 (m, 1H), 1.83-1.72 (m, 2H), 1.78 (s, 3H), 1.08 (d, 3H, J=7.2 Hz), 0.89 (m, 18H), 0.07 (s, 3H), 0.06 (s, 3H), 0.05 (s, 6H).

Synthesis of Intermediate 47

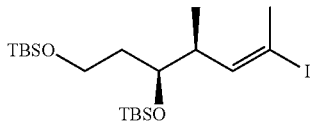 [SMILES: C/C(I)=C\[C@H](C)[C@H](CCO[Si](C)(C)C(C)(C)C)O[Si](C)(C)C(C)(C)C]

To a solution of 46 (200 mg, 0.56 mmol) in anhydrous toluene (7 mL), under Ar and at 23° C. bis(cyclopentadienyl)zirconium(IV) chloride hydride (432.3 mg, 1.68 mmol) was added and the reaction was stirred at 50° C. for 1 hour. During this time the reaction solution turned of orange colour. The reaction was cooled to 23° C. and iodine (284.3 mg, 1.12 mmol) was added in one portion. Stirring was continued for 30 min at room temperature and the reaction was diluted with hexane and filtered through Celite®. The filtrated was concentrated to afford a residue which was purified by flash chromatography eluting with hexane/dichloromethane (from 10:1 to 1:2) to furnish vinyl iodine 47 (140.4 mg, 49% yield) as pale yellow oil.

$^1$H NMR (CDCl$_3$, 300 MHz) δ: 6.07 (dd, 1H, J=9.9, 1.5 Hz), 3.72-3.67 (m, 1H), 3.65-3.61 (t, 2H, J=6.6 Hz), 2.53-2.47 (m, 1H), 2.37 (s, 3H), 1.68-1.61 (m, 2H), 0.92 (d, 3H, J=6.6 Hz), 0.89 (m, 18H), 0.05 (m, 12H).

Synthesis of Intermediate 48

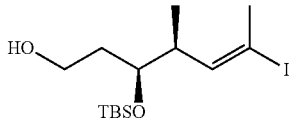 [SMILES: C/C(I)=C\[C@H](C)[C@H](CCO)O[Si](C)(C)C(C)(C)C]

To a solution of iodide 47 (140.4 mg, 0.27 mmol) in EtOH (2 mL) pyridinium p-toluenesulfonate (PPTS) (24 mg, 0.09 mmol) was added and the reaction mixture was stirred at room temperature for 25 hours. Then the solvent was removed under reduced pressure and the resulting oil was purified by column chromatography (hexane/EtOAc 4:1) affording 90.3 mg (83% yield) of alcohol 48 as colourless oil.

$^1$H NMR (CDCl$_3$, 300 MHz) δ: 6.01 (dd, 1H, J=9.9, 1.5 Hz), 3.78-3.67 (m, 3H), 2.62-2.55 (m, 1H), 2.39 (s, 3H), 2.00-1.98 (m, 1H), 1.80-1.62 (m, 2H), 0.96 (d, 3H, J=6.6 Hz), 0.89 (s, 9H), 0.09 (s, 3H), 0.08 (s, 3H).

Synthesis of Intermediate 49

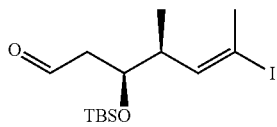 [SMILES: C/C(I)=C\[C@H](C)[C@H](CC=O)O[Si](C)(C)C(C)(C)C]

To a 0° C. solution of alcohol 48 (87 mg, 0.22 mmol) in anhydrous DCM (2 mL), Dess-Martin periodinane (140 mg, 0.33 mmol) was added. After 1 hour stirring at 0° C. and 30 min at 23° C. the reaction mixture was quenched with a saturated aqueous solution of NaHCO$_3$. The organic layer was decanted, dried over anhydrous Na$_2$SO$_4$ and concentrated under reduced pressure. Purification by column chromatography (hexane/EtOAc 20:1 to 2:1) afforded 76.6 mg (86% yield) of aldehyde 49 as a colourless oil.

$^1$H NMR (CDCl$_3$, 300 MHz) δ: 9.79 (t, 1H, J=2.4 Hz), 5.98 (dd, 1H, J=9.9, 1.5 Hz), 4.02-3.97 (m, 1H), 2.57-2.51 (m, 3H), 2.38 (s, 3H), 0.97 (d, 3H, J=6.6 Hz), 0.87 (s, 9H), 0.08 (s, 3H), 0.04 (s, 3H).

$^{13}$C NMR (CDCl$_3$, 75 MHz) δ: 201.5, 143.5, 95.1, 71.3, 49.3, 41.9, 28.3, 26.0, 18.2, 15.8, −4.2, −4.4.

Synthesis of Intermediate 50

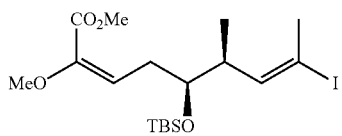 [SMILES: COC(=O)/C(=C\C[C@H](O[Si](C)(C)C(C)(C)C)[C@@H](C)/C=C(\C)I)OC]

To a solution of Diethyl(methoxy[methoxycarbonyl]methyl)phosphonate (73.7 mg, 0.29 mmol) and 18-crown-6 (153.4 mg, 0.58 mmol) in anhydrous THF (3 mL) stirred under argon atmosphere at −78° C., a 0.5 M Potassium bis(trimethylsilyl)amide (KHMDS) solution in toluene (0.58 mL, 0.29 mmol) was added dropwise. After 15 min aldehyde 49 (76.6 mg, 0.19 mmol) was added drop wise in anhydrous THF (2 mL) over a period of 10 min and stirred at −78° C. for 90 min. Then, the reaction was quenched with a saturated aqueous solution of NH$_4$Cl, warmed to room temperature and diluted with dichloromethane. The organic phase was dried (anhydrous Na$_2$SO$_4$) and evaporated under reduced pressure. Purification by column chromatography (hexane/EtOAc 30:1 to 5:1) afforded 89.0 mg (100% yield) of 50 as a mixture E/Z (regioselectivity>2.5:1 determined by $^1$H NMR) as a colourless oil mixture.

$^1$H NMR (CDCl$_3$, 300 MHz) for (2E, 7E)-50 δ: 6.28 (d, 1H, J=9.0 Hz), 5.33 (t, 1H, J=9.0 Hz), 3.84 (s, 3H), 3.61-3.57 (m, 1H), 3.61 (s, 3H), 2.77-2.70 (m, 1H), 2.64-2.55 (m, 1H), 2.49-2.37 (m, 1H), 2.30 (s, 3H), 0.96 (d, 3H, J=6.6 Hz), 0.89 (s, 9H), 0.06 (s, 3H), 0.05 (s, 3H).

Synthesis of Intermediate 51

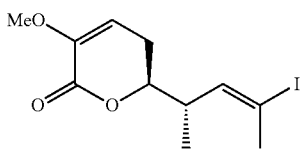

To a solution of ester 50 (90.8 mg, 0.19 mmol) in MeOH (3 mL) at room temperature, aqueous HCl 37% (34 μL) was added and the reaction mixture was stirred for 6 hours. Then the mixture was neutralized with a saturated aqueous solution of NaHCO$_3$ (pH 7-8) and the organic solvent was evaporated under reduced pressure. The resulting suspension was extracted with dichloromethane, dried and evaporated. The crude was purified by column chromatography (hexane/EtOAc 10:1 to 2:1) to yield 34 mg (50% yield) of lactone 51 as a white solid.

$^1$H NMR (CDCl$_3$, 300 MHz) δ: 5.99 (dd, 1H, J=9.9, 1.2 Hz), 5.62 (dd, 1H, J=5.1, 4.2 Hz), 4.19-4.11 (m, 1H), 3.64 (s, 3H), 2.78-2.70 (m, 1H), 2.41 (s, 3H), 2.42-2.37 (m, 2H), 1.11 (d, 3H, J=6.6 Hz).

Example 9

Synthesis of Fragment 56

Scheme 9 provides an example of the synthesis of fragment 56.

Scheme 9

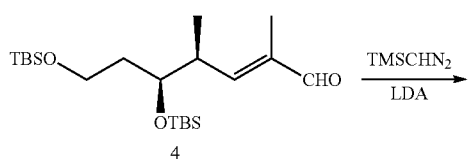

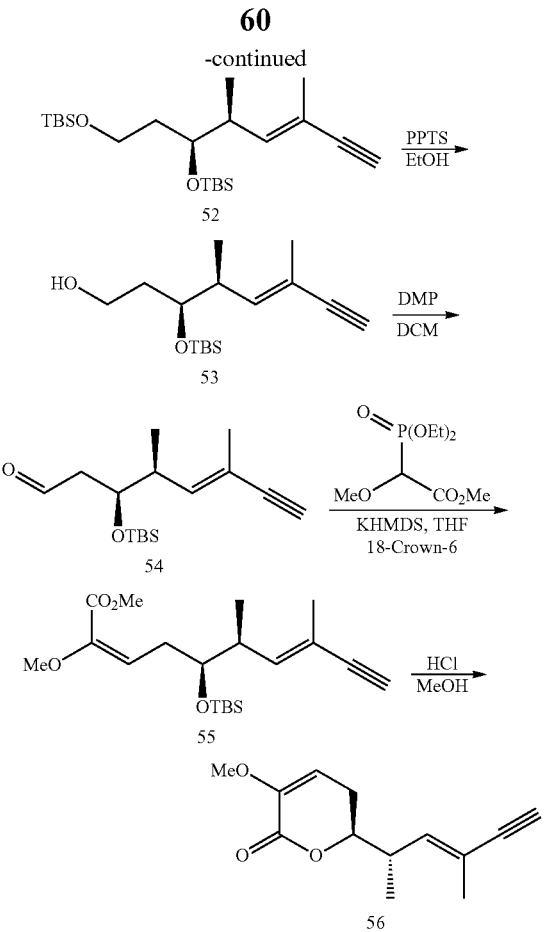

Synthesis of Intermediate 52

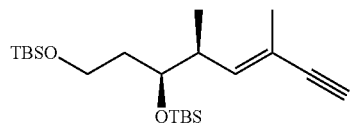 [SMILES: C#C/C(C)=C/[C@H](C)[C@H](CCO[Si](C)(C)C(C)(C)C)O[Si](C)(C)C(C)(C)C]

A solution of 1.8 M of Lithium diisopropylamide in heptane/THF/ethylbenzene (8.96 mL, 16.13 mmol) was diluted in 88 mL of anhydrous THF. After cooling down to −78° C., trimethylsilyldiazomethane (8.06 mL, 2M in THF, 16.13 mmol) was added and the resulting mixture was stirred for 30 min. A solution of 4 (4.377 g, 10.75 mmol) in anhydrous THF (35 mL) was added and stirring was maintained for 1 h at −78° C. and for 2 h at 23° C. The reaction mixture was added to ice-cooled water, and extracted with Et$_2$O. The combined organic layers were dried (anhydrous Na$_2$SO$_4$) and the solvent was removed. The residue was purified by flash chromatography to afford 2.38 g (55% yield) of 52 as yellow oil.

$^1$H NMR (CDCl$_3$, 300 MHz) δ: 5.86 (d, 1H, J=9.9 Hz), 3.73-3.63 (m, 3H), 2.74 (s, 1H), 2.58-2.50 (m, 1H), 1.80 (s, 3H), 1.70-1.63 (m, 2H), 0.93 (d, 3H, J=6.6 Hz), 0.88 (m, 18H), 0.04 (m, 12H).

$^{13}$C NMR (CDCl$_3$, 75 MHz) δ: 143.3, 116.3, 87.1, 73.7, 72.8, 60.0, 38.6, 38.0, 26.1, 26.1, 18.5, 18.3, 17.4, 15.3, −4.2, −5.1.

Synthesis of Intermediate 53

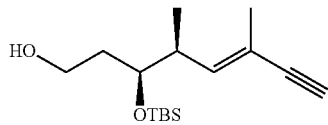 [SMILES: C#C/C(C)=C/[C@H](C)[C@H](CCO)O[Si](C)(C)C(C)(C)C]

To a solution of 52 (2.05 g, 5.17 mmol) in EtOH (50 mL) pyridinium p-toluenesulfonate (PPTS) (511.7 mg, 2.04 mmol) was added and the reaction mixture was stirred at room temperature for 25 hours. Then the solvent was removed under reduced pressure and the resulting oil was purified by column chromatography (hexane/EtOAc 4:1) affording 1.055 g (72% yield) of alcohol 53 as colourless oil.

$^1$H NMR (CDCl$_3$, 300 MHz) δ: 5.76 (d, 1H, J=9.9 Hz), 3.73-3.63 (m, 3H), 2.79 (s, 1H), 2.64-2.59 (m, 1H), 2.24 (bs, 1H), 1.80 (s, 3H), 1.70-1.60 (m, 2H), 0.95 (d, 3H, J=6.9 Hz), 0.88 (s, 9H), 0.08 (s, 3H), 0.06 (s, 3H).

Synthesis of Intermediate 54

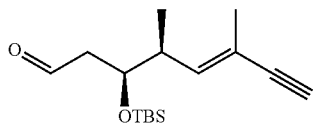 [SMILES: C#C/C(C)=C/[C@H](C)[C@H](CC=O)O[Si](C)(C)C(C)(C)C]

To a 0° C. solution of alcohol 53 (140 mg, 0.48 mmol) in anhydrous DCM (5 mL), Dess-Martin periodinane (308.5 mg, 0.73 mmol) was added.

After 30 min stirring at 0° C. and 60 min at 23° C. the reaction mixture was quenched with a saturated aqueous solution of NaHCO$_3$. The organic layer was decanted, dried over anhydrous Na$_2$SO$_4$ and concentrated under reduced pressure. Purification by column chromatography (hexane/dichloromethane 5:1 to 1:1) afforded 100 mg (73% yield) of aldehyde 54 as a colourless oil.

$^1$H NMR (CDCl$_3$, 300 MHz) δ: 9.79 (t, 1H, J=2.4 Hz), 5.72 (d, 1H, J=10.2 Hz), 4.02-3.96 (m, 1H), 2.77 (s, 1H), 2.64-2.53 (m, 3H), 1.80 (s, 3H), 0.98 (d, 3H, J=6.9 Hz), 0.87 (s, 9H), 0.08 (s, 3H), 0.04 (s, 3H).

$^{13}$C NMR (CDCl$_3$, 75 MHz) δ: 201.7, 141.2, 117.9, 86.6, 74.5, 71.8, 49.4, 39.7, 26.0, 18.2, 17.6, 16.2, −4.3, −4.4.

Synthesis of Intermediate 55

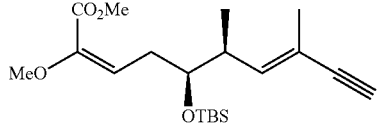 [SMILES: C#C/C(C)=C/[C@H](C)[C@H](C/C=C(/OC)C(=O)OC)O[Si](C)(C)C(C)(C)C]

To a solution of Diethyl(methoxy[methoxycarbonyl]methyl) phosphonate (768.6 mg, 3.02 mmol) and 18-crown-6 (1.60 g, 6.06 mmol) in anhydrous THF (30 mL) stirred under argon atmosphere at −78° C., a 0.5 M Potassium bis(trimethylsilyl) amide (KHMDS) solution in toluene (6.1 mL, 3.05 mmol) was added dropwise. After 15 min aldehyde 54 (578 mg, 2.02 mmol) in anhydrous THF (20 mL) was added dropwise over a period of 10 min and stirred at −78° C. for 90 min. Then, the reaction was quenched with a saturated aqueous solution of NH$_4$Cl, warmed to room temperature and diluted with dichloromethane. The organic phase was dried (anhydrous Na$_2$SO$_4$) and evaporated under reduced pressure. Purification by column chromatography (hexane/EtOAc 30:1 to 5:1) afforded 839.4 mg (>100% yield) of 55 as a colourless oil mixture E/Z (regioselectivity>4:1 determined by $^1$H NMR).

$^1$H NMR (CDCl$_3$, 300 MHz) for (2E, 7E)-55 δ: 5.73 (d, 1H, J=9.9 Hz), 5.33 (dd, 1H, J=7.8, 6.9 Hz), 3.80 (s, 3H), 3.61-3.57 (m, 1H), 3.59 (s, 3H), 2.77-2.68 (m, 1H), 2.73 (bs, 1H), 2.58-2.44 (m, 2H), 1.72 (bs, 3H), 0.95 (d, 3H, J=6.6 Hz), 0.85 (s, 9H), 0.05 (s, 3H), 0.04 (s, 3H).

Synthesis of Intermediate 56

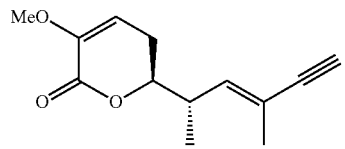 [SMILES: C#C/C(C)=C/[C@H](C)[C@@H]1CC=C(OC)C(=O)O1]

To a solution of ester 55 (839.4 mg, 2.29 mmol) in MeOH (30 mL) at room temperature, aqueous HCl 37% (766 μL, 9.16 mmol) was added and the reaction mixture was stirred for 4 hours. Then the mixture was neutralized with a saturated aqueous solution of NaHCO$_3$ (pH 7-8) and the organic solvent was evaporated under reduced pressure. The resulting suspension was extracted with dichloromethane, dried and evaporated. The crude was purified by column chromatography (hexane/EtOAc 10:1 to 1:3) to yield 312.7 mg (62% yield) of lactone 56 as a white solid.

$^1$H NMR (CDCl$_3$, 300 MHz) δ: 5.72 (dd, 1H, J=10.2, 1.8 Hz), 5.60 (dd, 1H, J=5.1, 4.2 Hz), 4.20-4.10 (m, 1H), 3.64 (s, 3H), 2.85-2.2.77 (m, 1H), 2.81 (s, 1H), 2.41-2.36 (m, 2H), 1.84 (s, 3H), 1.13 (d, 3H, J=6.9 Hz).

$^{13}$C NMR (CDCl$_3$, 125 MHz) δ: 161.3, 145.1, 138.6, 118.9, 108.0, 85.9, 81.3, 74.8, 55.4, 37.2, 26.2, 17.5, 16.2.

MS (ES) [m/z]=243.2 [M+Na]$^+$.

Example 10

Synthesis of Fragment 62

Scheme 10 provides an example of the synthesis of fragment 62.

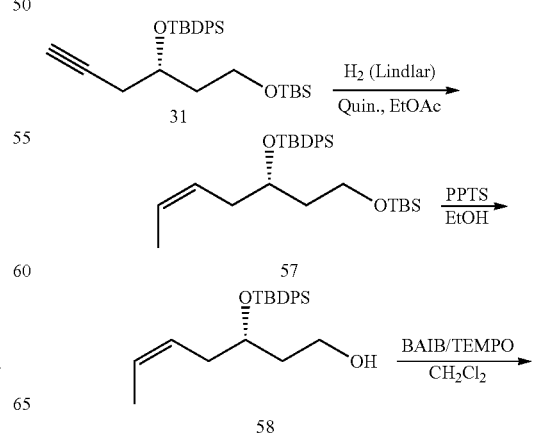

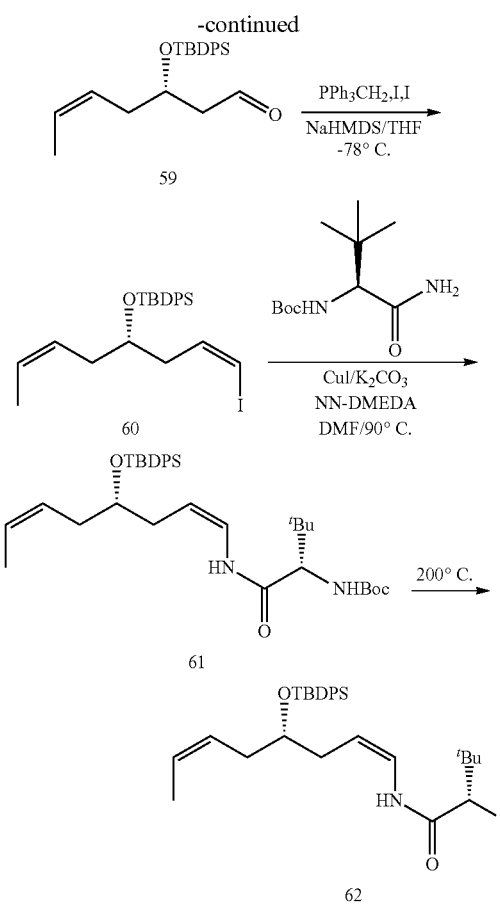

Synthesis of Intermediate 57

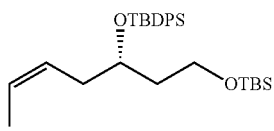

A flask containing a mixture of 31 (4.73 g, 9.85 mmol), quinoline (0.582 mL, 4.92 mmol) and Lindlar catalyst (2.18 g) in ethyl acetate was evacuated and flushed with $H_2$. The reaction mixture was stirred at room temperature under $H_2$ (1 atm) for 2 h and then filtered through a plug of celite. The plug was rinsed with ethyl acetate and the combined filtrates were washed with 0.1% HCl. The organic layer was dried over anhydrous $Na_2SO_4$, filtered and concentrated to afford intermediate 57 (4.27 g, yield: 90%) as a colourless oil that was used without further purification.

$^1$H NMR (CDCl$_3$, 300 MHz) δ: 7.70-7.67 (m, 4H), 7.44-7.36 (m, 6H), 5.48 (m, 1H), 5.36-5.27 (m, 1H), 3.95-3.87 (m, 1H), 3.71-3.55 (m, 2H), 2.16 (dd, 2H, J=6.9, 6.3 Hz), 1.73-1.66 (m, 2H), 1.41 (dd, 3H, J=6.6, 1.2 Hz), 1.05 (s, 9H), 0.84 (s, 9H), −0.02 (s, 6H).

$^{13}$C NMR (CDCl$_3$, 75 MHz) δ: 136.2, 134.8, 129.8, 127.8, 126.4, 125.8, 70.9, 60.4, 39.6, 34.8, 27.3, 26.2, 19.7, 18.5, 13.1, −5.1.

Synthesis of Intermediate 58

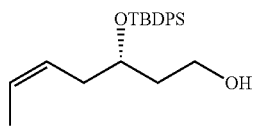

PPTS (837.7 mg, 3.33 mmol) was added in one portion to a solution of 57 (4 g, 8.33 mmol) in ethanol (80 mL). The reaction mixture was stirred at room temperature for 7 h and then was concentrated. The residue was diluted in DCM and washed with a saturated solution of NaHCO$_3$. The organic layer was extracted, dried over anhydrous Na$_2$SO$_4$, filtered and concentrated. Flash chromatography (Hex/EtOAc, 95:1) gave the silyl ether 58 (2.12 g, yield: 69%) as a colourless oil.

$^1$H NMR (CDCl$_3$, 300 MHz) δ: 7.73-7.69 (m, 4H), 7.44-7.36 (m, 6H), 5.44-5.38 (m, 1H), 5.21-5.17 (m, 1H), 4.01-3.94 (m, 1H), 3.84-3.76 (m, 1H), 3.69-3.64 (m, 1H), 2.32-2.14 (m, 2H), 1.89-1.78 (m, 1H), 1.70-1.60 (m, 1H), 1.37 (d, 3H, J=6.9 Hz), 1.07 (s, 9H).

$^{13}$C NMR (CDCl$_3$, 75 MHz) δ: 136.2, 134.1, 130.0, 127.8, 126.3, 125.9, 72.3, 60.1, 37.7, 34.3, 27.2, 19.5, 13.0.

Synthesis of Intermediate 59

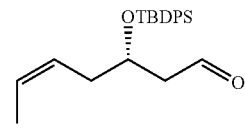

BAIB (1.97 g, 6.11 mmol) was added to a solution of alcohol 58 (2.05 g, 5.56 mmol) and TEMPO (86.87 mg, 0.56 mmol) in 25 mL of DCM. The reaction mixture was stirred at room temperature for 16-18 h until the alcohol was no longer detectable (TLC), and then it was quenched with a saturated aqueous solution of NH$_4$Cl, and extracted with DCM. The combined organic phases were dried over anhydrous Na$_2$SO$_4$, filtered and concentrated. The residue was purified by flash chromatography (Hexane/DCM 5:1 to 1:2) to give 59 (1.733 mg, yield: 79%) as a colourless oil.

$^1$H NMR (CDCl$_3$, 300 MHz) δ: 9.72 (t, 1H, J=2.7 Hz), 7.74-7.67 (m, 4H), 7.48-7.37 (m, 6H), 5.56-5.45 (m, 1H), 5.32-5.23 (m, 1H), 4.29-4.20 (m, 1H), 2.51-2.48 (m, 2H), 2.31-2.27 (m, 2H), 1.43 (dd, 3H, J=6.9, 1.5 Hz), 1.06 (s, 9H).

$^{13}$C NMR (CDCl$_3$, 75 MHz) δ: 202.3, 136.1, 134.0, 130.1, 127.9, 127.4, 125.1, 69.4, 50.1, 35.1, 27.2, 19.5, 13.1.

Synthesis of Intermediate 60

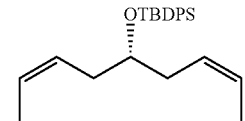

To a suspension of iodomethyltriphenylphosphorane (3.32 g, 6.38 mmol) in anhydrous THF (60 mL) at room temperature 6.83 mL of a 1M solution of NaHMDS (6.38 mmol) in THF was slowly added. After stirring for 2 min, the yellow mixture was cooled to −78° C. and a solution of 59 (1.67 g, 4.56 mmol) in anhydrous THF (40 mL) was then added. The reaction mixture was stirred at −78° C. for 90 min, then at room temperature for 5 min, diluted with hexane and filtered through a plug celite/SiO$_2$. The plug was rinsed with Hexane/

EtOAc (10:1 to 5:1) to afford compound 60 (2 g, yield: 89%) as a colourless oil that was used without further purification.

$^1$H NMR (CDCl$_3$, 300 MHz) δ: 7.70-7.66 (m, 4H), 7.45-7.34 (m, 6H), 6.21-6.31 (m, 2H), 5.49-5.43 (m, 1H), 5.35-5.27 (m, 1H), 3.94-3.75 (m, 1H), 2.30-2.27 (m, 2H), 2.24-2.04 (m, 2H), 1.43 (d, 3H, J=6.6 Hz), 1.06 (s, 9H).

$^{13}$C NMR (CDCl$_3$, 75 MHz) δ: 138.2, 136.2, 134.3, 129.9, 127.8, 126.4, 126.0, 84.1, 71.9, 41.6, 34.5, 27.2, 19.6, 13.2.

Synthesis of Intermediate 61

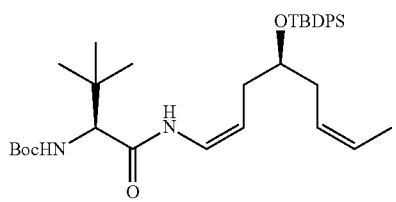

A resealable Schlenk tube was charged with copper (I) iodide (232.4 mg, 1.22 mmol), potassium carbonate (1.688 g, 12.23 mmol) and Boc-tert-LeuCONH$_2$ (2.474 g, 6.12 mmol), evacuated and filled with argon. N,N'-Dimethylethylenediamine (0.26 mL, 2.45 mmol), vinyl iodide 60 (2 g, 4.08 mmol) and anhydrous DMF (35 mL) were added under argon. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/EtOAc, 20:1 to 15:1). Intermediate 61 (1.06 g, yield: 44%) was obtained as an oil.

$^1$H NMR (CDCl$_3$, 300 MHz) δ: 7.70-7.67 (m, 4H), 7.43-7.35 (m; 6H), 7.13 (d, 1H, J=10.5 Hz), 6.67 (dd, 1H, J=10.2, 9.6 Hz), 5.56-5.45 (m, 1H), 5.36-5.28 (m, 2H), 4.86-4.78 (m, 2H), 3.88-3.77 (m, 1H), 2.26-2.04 (m, 4H), 1.44 (d, 3H, J=6.9 Hz), 1.43 (s, 9H), 1.06 (s, 9H), 0.96 (s, 9H).

Synthesis of Intermediate 62

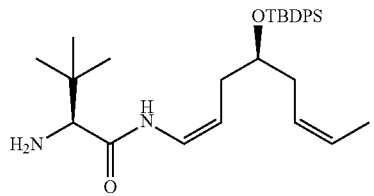

A solution of amino protected derivative 61 (847 mg, 1.43 mmol) in ethylenglycol (50 mL) was heated at 200° C. for 10-20 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over anhydrous Na$_2$SO$_4$, filtrated and concentrated in vacuo to afford the primary amine 62 (435 mg, 62%) as a white foam after purification by flash chromatography (Hexane/EtOAc 10:1 to 1:2).

$^1$H NMR (CDCl$_3$, 300 MHz) δ: 8.50 (d, 1H, J=10.8 Hz), 7.70-7.66 (m, 4H), 7.45-7.33 (m, 6H), 6.67 (dd, 1H, J=11.1, 9.3 Hz), 5.48-5.40 (m, 1H), 5.36-5.28 (m, 1H), 4.79 (dd, 1H, J=16.2, 7.5 Hz), 3.87-3.79 (m, 1H), 3.08 (s, 1H), 2.22-2.14 (m, 4H), 1.43 (d, 3H, J=6.9 Hz), 1.05 (s, 9H), 0.97 (s, 9H).

$^{13}$C NMR (CDCl$_3$, 75 MHz) δ: 171.0, 136.1, 134.5, 129.8, 127.8, 126.3, 126.2, 122.1, 107.6, 72.6, 64.4, 34.0, 34.4, 32.8, 27.2, 26.9, 19.6, 13.2.

Example 11

Synthesis of Fragment 63

Scheme 11 provides an example of the synthesis of fragment 63.

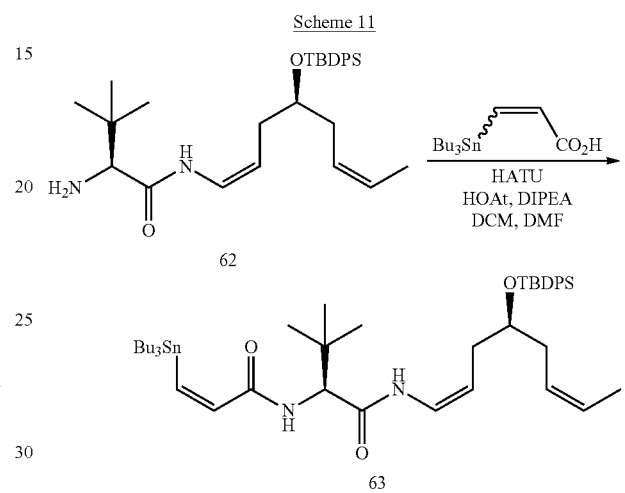

Synthesis of Intermediate 63

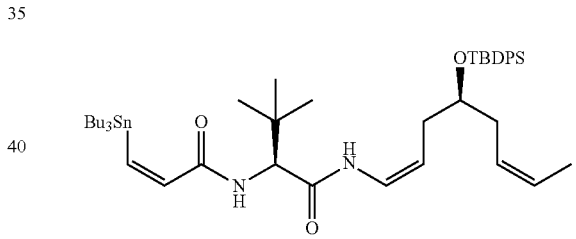

To a solution of amine 62 (575 mg, 1.17 mmol) in anhydrous DCM/DMF (4:1, 12.5 mL), a solution of (Z)-3-tributylstannylpropenoic acid (505.6 mg, 1.4 mmol) in anhydrous DCM was added, under argon atmosphere, and then was cooled at 0° C. DIPEA (0.243 mL, 1.76 mol), 7-hydroxybenzotriazole (HOBt) (189.2 mg, 1.4 mmol), and HATU (532.28 mg, 1.4 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over anhydrous Na$_2$SO$_4$, filtered and concentrated. The residue was purified by flash chromatography (Hexane/EtOAc 20:1 to 15:1) to give amide 63 (780.4 mg; yield: 77%) as a white foam.

$^1$H NMR (CDCl$_3$, 300 MHz) δ: 7.70-7.68 (m, 4H), 7.43-7.36 (m, 6H), 7.02 (d, 1H, J=12.3 Hz), 7.00 (d, 1H, J=10.8 Hz), 6.75 (d, 1H, J=12.3 Hz), 6.66 (t, 1H, J=9.3 Hz), 6.26 (d, 1H, J=9.6 Hz), 5.57-5.34 (m, 1H), 5.38-5.28 (m, 1H), 4.83 (dd, 1H, J=16.5, 7.8 Hz), 4.31 (d, 1H, J=9.6 Hz), 3.89-3.82 (m, 1H), 2.26-2.02 (m, 4H), 1.50-1.42 (m, 6H), 1.43 (d, 3H, J=6.9 Hz), 1.33-1.20 (m, 6H), 1.06 (s, 9H), 0.96 (s, 9H), 0.95-0.83 (m, 15H)

$^{13}$C-RMN (CDCl$_3$, 75 MHz) δ: 168.0, 166.2, 153.8, 136.3, 136.1, 134.3, 130.0, 127.8, 126.7, 126.0, 121.6, 109.0, 72.6, 60.7, 35.7, 34.0, 32.7, 29.5, 27.7, 27.2, 26.7, 19.5, 14.0, 13.2, 11.8.

Example 12

Scheme 12 provides the synthesis of several compounds of the invention.

Scheme 12

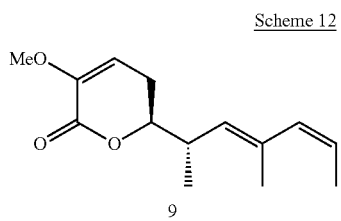

9

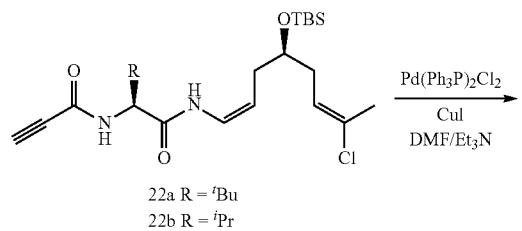

22a R = $^t$Bu
22b R = $^i$Pr

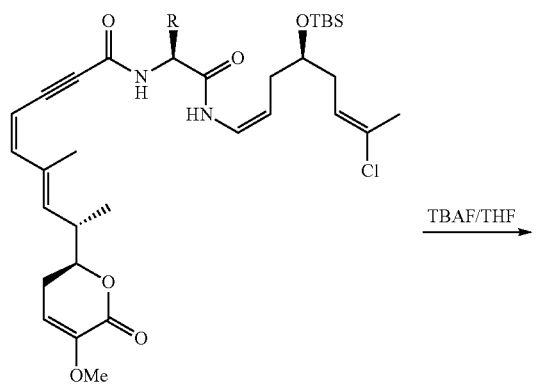

64a R = $^t$Bu
64b R = $^i$Pr

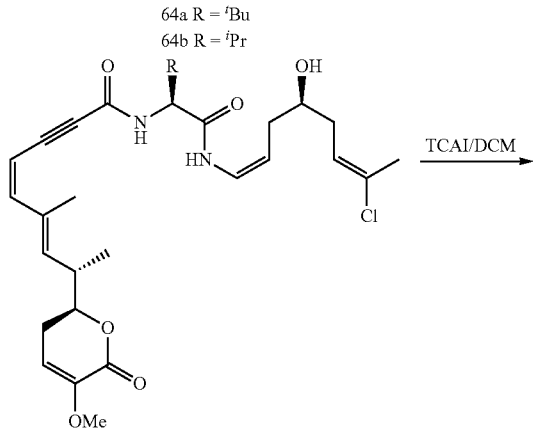

65a R = $^t$Bu
65b R = $^i$Pr

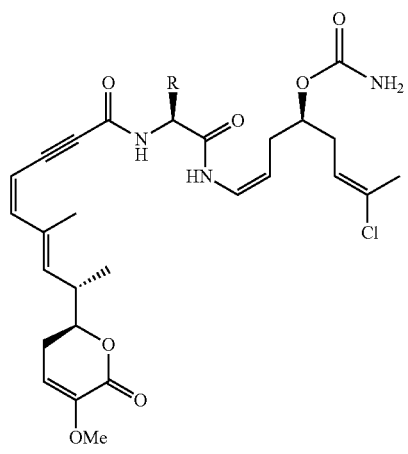

66a R = $^t$Bu
66b R = $^i$Pr

Synthesis of Intermediate 64a

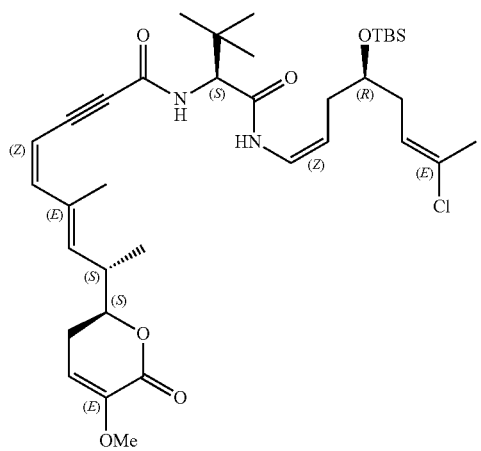

To a solution of iodo compound 9-(11 mg, 0.033 mmol) in DMF/Et$_3$N (0.25 ml and 0.05 ml) under N$_2$ at −20° C., Pd(Ph$_3$P)$_2$Cl$_2$ (2.3 mg, 0.0033 mmol) and CuI (1.9 mg, 0.01 mmol) were added. Then, compound 22a (15 mg, 0.03 mmol in 0.1 ml DMF) was added and the reaction mixture was stirred at −20° C. to room temperature for 3 hours. The crude was quenched with H$_2$O and extracted with ethyl acetate. The organic phase was dried (anhydrous Na$_2$SO$_4$) and evaporated under reduced pressure. Purification by column chromatography (Ethyl acetate/hexanes mixture) to afforded pure compound 64a (10 mg, yield: 46%).

$^1$H NMR (CDCl$_3$, 300 MHz) δ: 7.75 (d, 1H, J=10.5 Hz), 6.70 (t, 1H, J=10.2 Hz), 6.50 (d, 1H J=9.3 Hz), 6.38 (d, 1H, J=12.3 Hz), 5.60 (m, 3H), 5.45 (d, 1H, J=12.0 Hz), 4.87 (q, 1H, J=8.1 Hz), 4.37 (d, 1H, J=9.3 Hz), 4.21 (m, 1H), 3.77 (m, 1H), 3.64 (s, 3H), 2.87 (m, 1H), 2.40 (m, 2H), 2.20 (m, 4H), 2.09 (s, 3H), 2.01 (s, 3H), 1.15 (d, 3H, J=6.6 Hz), 1.02 (s, 9H), 0.89 (s, 9H), 0.07 (s, 3H), 0.05 (s, 3H).

Synthesis of Intermediate 64b

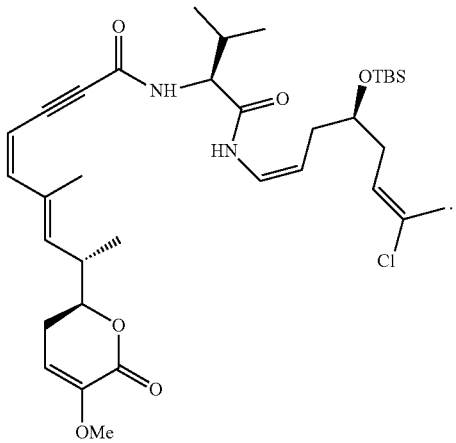 [SMILES: COC1=CC[C@@H]([C@@H](C)/C=C(C)/C=C\C#CC(=O)N[C@H](C(=O)N/C=C\C[C@H](C/C=C(\C)Cl)O[Si](C)(C)C(C)(C)C)C(C)C)OC1=O]

To a solution of 9 (40 mg, 0.113 mmol) in DMF/Et$_3$N (1 ml and 0.19 ml) at −20° C., Pd(Ph$_3$P)$_2$Cl$_2$ (7.9 mg, 0.113 mmol) and CuI (6.5 mg, 0.034 mmol) were added. Then, 22b (50 mg, 0.113 mmol in 0.4 ml DMF) was added and the reaction was stirred at −20° C. to room temperature for 3 hours. The crude mixture was quenched with H$_2$O and extracted with Ethyl acetate. The organic phase was dried (anhydrous Na$_2$SO$_4$) and evaporated under reduced pressure. Purification by column chromatography (Ethyl acetate/hexanes mixture) to afforded pure 64b (40 mg, yield: 54%).

$^1$H NMR (CDCl$_3$, 300 MHz) δ: 7.77 (d, 1H, J=11.4 Hz), 6.75 (t, 1H, J=10.2 Hz), 6.41-6.36 (m, 2H), 5.64-5.56 (m, 3H), 5.46 (d, 1H, J=11.7 Hz), 4.86 (q, 1H, J=8.1 Hz), 4.31 (dd, 1H, J=8.4; 6.6 Hz), 4.25-4.16 (m, 1H), 3.84-3.76 (m, 1H), 3.65 (s, 3H), 2.92-2.81 (m, 1H), 2.44-2.39 (m, 2H), 2.22-2.12 (m, 5H), 2.10 (s, 3H), 2.03 (s, 3H), 1.16 (d, 3H, J=6.6 Hz), 0.99 (dd, 6H, J=9.3; 6.9 Hz), 0.89 (s, 9H), 0.0080 (s, 3H), 0.0064 (s, 3H).

Synthesis of Compound 65a

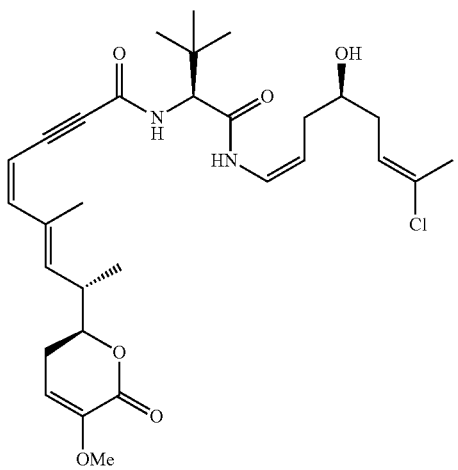 [SMILES: COC1=CC[C@@H]([C@@H](C)/C=C(C)/C=C\C#CC(=O)N[C@H](C(=O)N/C=C\C[C@@H](O)C/C=C(\C)Cl)C(C)(C)C)OC1=O]

To a solution of 64a (15 mg, 0.022 mmol) in anhydrous THF (0.5 mL) under N$_2$ and at room temperature, TBAF 1M in THF (0.044 mL, 0.044 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (Hexane/EtOAc 3:1 to 1:2) to give alcohol 65a (5 mg; yield: 42%).

$^1$H NMR (CDCl$_3$, 300 MHz) δ: 8.78 (d, 1H, J=9.6 Hz), 6.77 (t, 1H, J=9.0 Hz), 6.57 (d, 1H J=9.0 Hz), 6.38 (d, 1H, J=12.3 Hz), 5.60 (m, 3H), 5.45 (d, 1H, J=12.0 Hz), 4.90 (q, 1H, J=8.7 Hz), 4.29 (d, 1H, J=9.6 Hz), 4.23 (m, 1H), 3.80 (m, 1H), 3.65 (s, 3H), 2.86 (m, 1H), 2.66 (bs, 1H), 2.40 (m, 2H), 2.21 (m, 4H), 2.07 (s, 3H), 2.04 (s, 3H), 1.15 (d, 3H, J=6.6 Hz), 1.02 (s, 9H).

Synthesis of Compound 65b

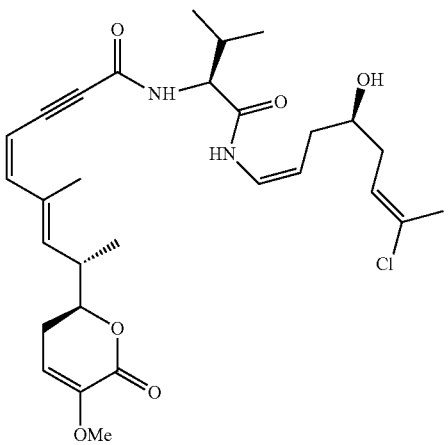 [SMILES: COC1=CC[C@@H]([C@@H](C)/C=C(C)/C=C\C#CC(=O)N[C@H](C(=O)N/C=C\C[C@@H](O)C/C=C(\C)Cl)C(C)C)OC1=O]

To a solution of 64b (40 mg, 0.06 mmol) in anhydrous THF (0.9 ml) under N$_2$ and at room temperature, TBAF 1M in THF (0.12 ml, 0.067 mmol) was added. The reaction was stirred at room temperature for 16 hours and then quenched with NH$_4$Cl and extracted with CH$_2$Cl$_2$. The organic phase was dried (anhydrous Na$_2$SO$_4$) and evaporated under reduced pressure. Purification by column chromatography (Ethyl acetate/hexanes mixture) afforded pure 65b (15 mg, yield: 45%).

$^1$H NMR (CDCl$_3$, 300 MHz) δ: 8.95 (d, 1H, J=10.2 Hz), 6.77 (t, 1H, J=9.3 Hz), 6.60 (d, 1H, J=9.0 Hz), 6.38 (d, 1H, J=12.6 Hz), 5.64-5.60 (m, 3H), 5.45 (d, 1H, J=12.0 Hz), 4.88 (q, 1H, J=8.4 Hz), 4.34 (dd, 1H, J=8.7; 7.2 Hz), 4.27-4.20 (m, 1H), 3.82-3.74 (m, 1H), 3.65 (s, 3H), 2.92-2.82 (m, 1H), 2.45-2.38 (m, 2H), 2.11-2.04 (m, 5H), 1.57-1.45 (m, 6H), 1.28-1.23 (m, 3H), 1.15 (d, 6H, J=6.6 Hz).

Synthesis of Compound 66a

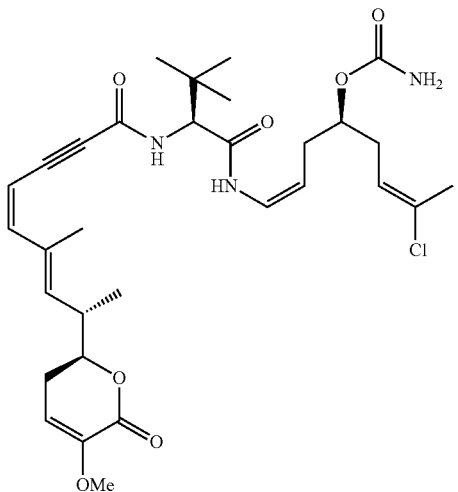 [SMILES: COC1=CC[C@@H]([C@@H](C)/C=C(C)/C=C\C#CC(=O)N[C@H](C(=O)N/C=C\C[C@H](C/C=C(\C)Cl)OC(N)=O)C(C)(C)C)OC1=O]

To a solution of 65a (3.5 mg, 0.0062 mmol) in anhydrous DCM (0.45 mL) at room temperature, trichloroacetyl isocyanate (TCAI) (1 µl, 0.0075 mmol) was added. The reaction was stirred at room temperature for 30 min and then neutral aluminium oxide was added (100 mg). The mixture was stirred for 30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 2:1 to 1:2) affording compound 66a (2.5 mg, yield: 70%).

$^1$H NMR (CDCl$_3$, 500 MHz) δ: 8.72 (d, 1H, J=10.5 Hz), 6.84 (t, 1H, J=9.0 Hz), 6.66 (d, 1H J=10.0 Hz), 6.38 (d, 1H, J=12.0 Hz), 5.60 (m, 3H), 5.46 (d, 1H, J=12.0 Hz), 4.82 (q, 1H, J=8.0 Hz), 4.42 (m, 2H), 4.22 (m, 1H), 3.65 (s, 3H), 2.88 (m, 1H), 2.44-2.32 (m, 6H), 2.10 (s, 3H), 2.06 (s, 3H), 1.15 (d, 3H, J=7.0 Hz), 1.05 (s, 9H).

MS (ES) (m/z) 604.2 [M+1]$^+$, 626.2 (M+Na$^+$).

Synthesis of Compound 66b

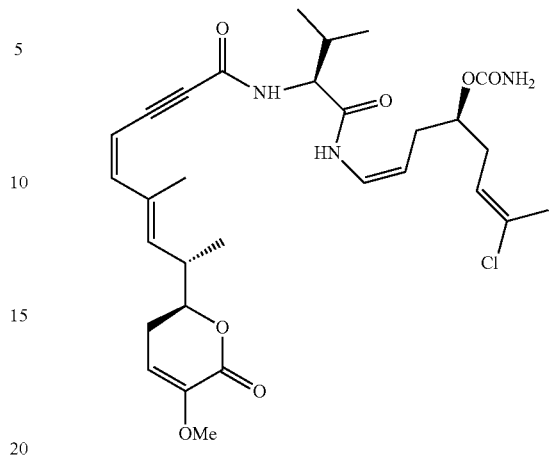

To a solution of 65b (32 mg, 0.06 mmol) in CH$_2$Cl$_2$ (4.2 ml) at r.t, trichloroacetyl isocyanate (TCAI) (8.5 µl, 0.072 mmol) was added. The reaction was stirred at room temperature for 30 min and then neutral Alumina was added (450 mg) while stirring for additional 30 min. The reaction mixture was filtered over alumina using a mixture of CH$_2$Cl$_2$/MeOH 1:1 and after evaporation of the filtrated at reduced pressure the product was purified by column chromatography (Hexane/EOAct mixtures) to afford pure 66b (12 mg, yield: 35%).

$^1$H NMR (CDCl$_3$, 300 MHz) δ: 8.90 (d, 1H, J=10.8 Hz), 6.84 (t, 1H, J=9.0 Hz), 6.74 (d, 1H, J=8.7 Hz), 6.38 (d, 1H, J=12.0 Hz), 5.64-5.58 (m, 3H), 5.45 (d, 1H, J=12.0 Hz), 5.38 (br s, 2H), 4.86-4.78 (m, 1H), 4.44-4.39 (m, 2H), 4.27-4.19 (m, 1H), 3.65 (s, 3H), 2.96-2.84 (m, 1H), 2.51-2.39 (m, 2H), 2.37-2.30 (m, 5H), 2.18-2.04 (m, 6H), 1.15 (d, 3H, J=6.6 Hz), 1.00-0.96 (m, 6H).

Example 13

Scheme 13 provides the synthesis of several compounds of the invention.

Scheme 13

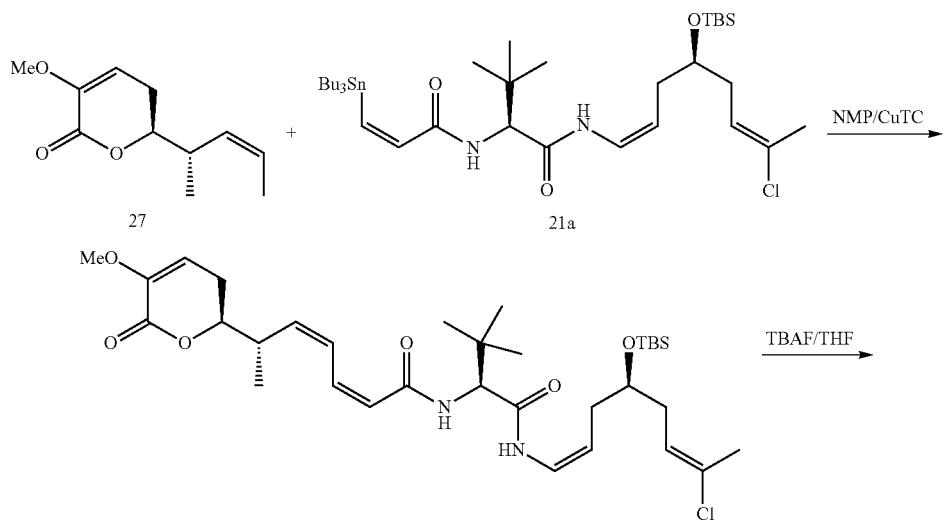

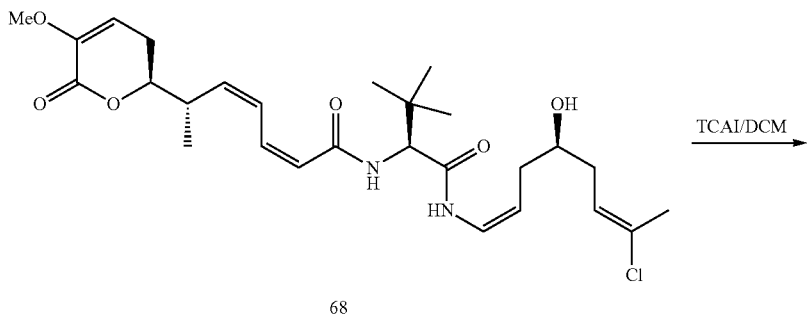

68

TCAI/DCM →

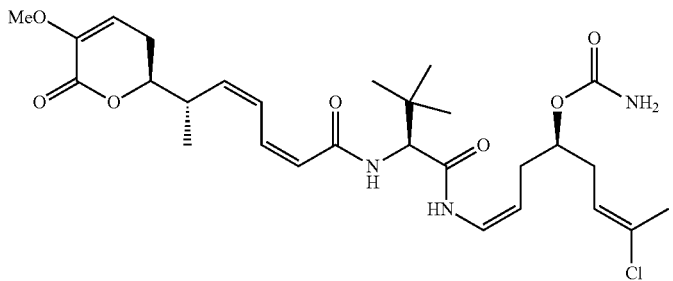

69

Synthesis of Compound 67

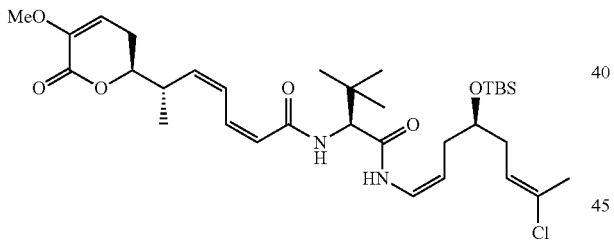

Synthesis of Compound 68

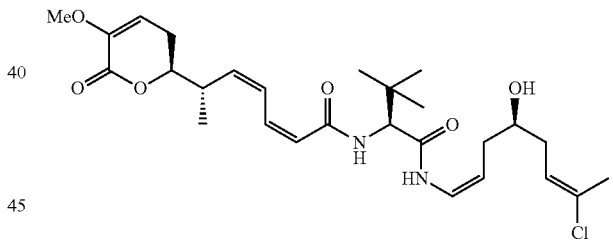

To a solution of alkenylstannane 21a (50 mg, 0.07 mmol) and iodide 27 (24.8 mg, 0.08 mmol) in 1-methyl-2-pyrrolidinone (NMP) (1 mL) at 0° C., Copper thiophenecarboxylate (CuTC) (19.2 mg, 0.1 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×5 mL). The organic solution was dried and evaporated to give the crude product which was purified by column chromatography (Hexane/EtOAc 10:1 to 6:1) to give triene 67 (19 mg, yield: 44%) as an oil.

$^{1}$H NMR (CDCl$_{3}$, 300 MHz) δ: 7.73 (d, 1H, J=10.5 Hz), 7.41 (dd, 1H, J=11.7, 11.1 Hz), 6.77-6.68 (m, 2H), 6.37 (d, 1H, J=9.3 Hz), 5.74 (d, 1H, J=11.4 Hz), 5.61-5.52 (m, 3H), 4.87-4.79 (m, 1H), 4.37 (d, 1H, J=9.3 Hz), 4.21-4.14 (m, 1H), 3.79-3.72 (m, 1H), 3.64 (s, 3H), 3.09-2.99 (m, 1H), 2.39-2.35 (m, 2H), 2.20-2.10 (m, 4H), 2.01 (s, 3H), 1.16 (d, 3H, J=6.6 Hz), 1.03 (s, 9H), 0.88 (s, 9H), 0.07 (s, 3H), 0.05 (s, 3H).

To a solution of 67 (18 mg, 0.03 mmol) in anhydrous THF (0.42 mL) under N$_{2}$ and at room temperature, TBAF 1M in THF (0.05 mL, 0.05 mmol) was added. The reaction was stirred at room temperature for 18 hours and then quenched with a saturated aqueous solution of NH$_{4}$Cl and extracted with EtOAc. The combined organic phases were dried over anhydrous Na$_{2}$SO$_{4}$, filtered, and concentrated. The residue was purified by flash chromatography (Hexane/EtOAc 3:1 to 1:2) to give alcohol 68 (16 mg, yield: 80%) as an oil.

$^{1}$H NMR (CDCl$_{3}$, 300 MHz) δ: 8.90 (d, 1H, J=10.5 Hz), 7.42 (dd, 1H, J=11.7, 11.1 Hz), 6.78-6.69 (m, 2H), 6.59 (d, 1H, J=9.3 Hz), 5.75 (d, 1H, J=11.4 Hz), 5.64-5.53 (m, 3H), 4.88-4.80 (m, 1H), 4.37 (d, 1H, J=9.3 Hz), 4.22-4.15 (m, 1H), 3.77-3.69 (m, 1H), 3.64 (s, 3H), 3.11-3.01 (m, 1H), 2.39-2.35 (m, 2H), 2.24-2.14 (m, 4H), 2.03 (s, 3H), 1.16 (d, 3H, J=6.6 Hz), 1.03 (s, 9H).

Synthesis of Compound 69

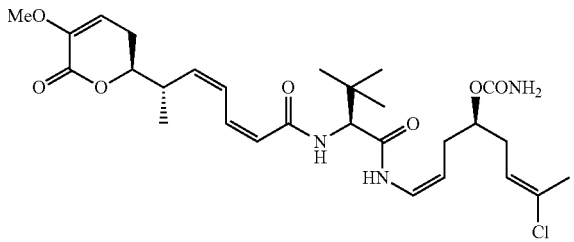

To a solution of 68 (15 mg, 0.02 mmol) in anhydrous DCM (0.3 mL) at room temperature, trichloroacetyl isocyanate (TCAI) (4.1 μl, 0.64 mmol) was added. The reaction was stirred at room temperature for 30 min and then neutral aluminium oxide was added (450 mg). The mixture was stirred for 30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 2:1) to give compound 69 (14 mg, yield: 86%).

$^1$H NMR (CDCl$_3$, 300 MHz) δ: 8.89 (d, 1H, J=10.5 Hz), 7.45 (m, 1H), 6.87-6-71 (m, 2H), 6.53 (d, 1H, J=9.6 Hz), 5.75 (m, 2H), 5.60-5.57 (m, 2H), 4.81 (m, 1H), 4.40-4.37 (m, 2H), 4.19 (dd, 1H, J=9.3, 9.5 Hz), 3.66 (s, 3H), 3.06 (m, 1H), 2.40-2.30 (m, 5H), 2.15-2.08 (m, 1H), 2.07 (s, 3H), 1.17 (d, 3H, J=4.2 Hz), 1.04 (s, 9H).

$^{13}$C NMR (CDCl$_3$, 75.5 MHz) δ: 168.1, 165.9, 161.4, 157.7, 145.2, 138.3, 135.2, 132.0, 125.9, 124.5, 122.3, 121.8, 108.1, 105.2, 81.4, 75.1, 60.7, 55.4, 36.1, 35.0, 32.9, 30.8, 26.7, 26.3, 21.0, 17.0

Example 14

Scheme 14 provides the synthesis of several compounds of the invention

Scheme 14

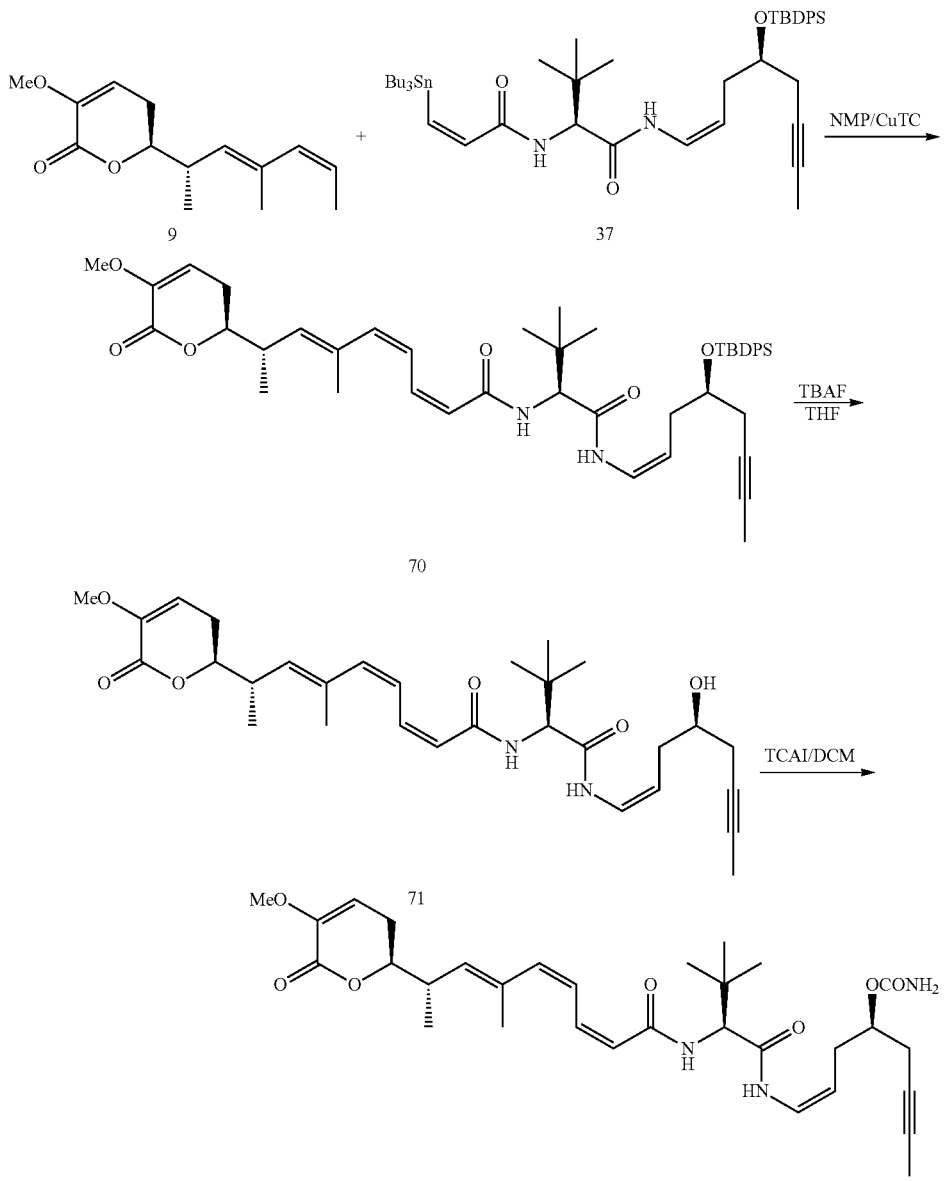

Synthesis of Compound 70

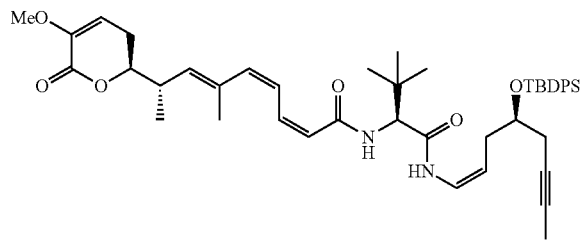

To a solution of alkenylstannane 37 (94 mg, 0.112 mmol) and 9 (47 mg, 0.135 mmol in 1-methyl-2-pyrrolidinone (NMP) (1.1 mL) at 0° C., Copper thiophenecarboxylate (CuTC) (32.2 mg, 0.168 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×15 mL). The organic solution was dried and evaporated to give the crude product which was purified by column chromatography (Hexane/EtOAc 2:1 to 1:1) to give triene 70 (81.4 mg, yield: 79%) as an oil.

$^1$H NMR (CDCl$_3$, 300 MHz) δ: 7.74 (d, 1H, J=10.5 Hz), 7.66-7.64 (m, 4H), 7.44-7.38 (m, 6H), 7.22 (dd, 1H, J=12.3, 11.4 Hz), 6.86 (dd, 1H, J=11.7, 11.4 Hz), 6.70 (dd, 1H, J=9.9, 9.3 Hz), 6.40 (d, 1H, J=9.3 Hz), 6.17 (d, 1H, J=11.4 Hz), 5.66 (d, 1H, J=11.4 Hz), 5.60 (dd, 1H, J=5.4, 3.9 Hz), 5.26 (d, 1H, J=10.2 Hz), 4.84-4.76 (m, 1H), 4.3 (d, 1H, J=9.3 Hz), 4.20-4.16 (m, 1H), 3.88-3.80 (m, 1H), 3.64 (s, 3H), 2.89-2.77 (m, 1H), 2.41-2.33 (m, 3H), 2.28-2.20 (m, 3H), 1.91 (s, 3H), 1.82 (s, 3H), 1.13 (d, 3H, J=6.9 Hz), 1.02 (s, 9H), 0.86 (s, 9H).

Synthesis of Compound 71

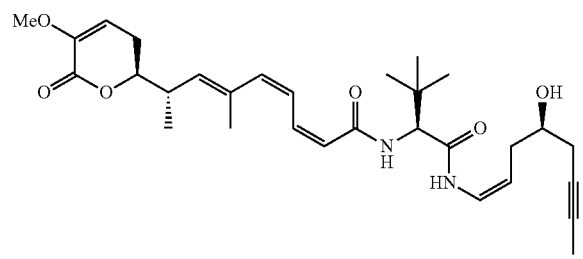 [SMILES: CC#CC[C@H](O)C/C=C\NC(=O)[C@@H](NC(=O)\C=C/C=C\C(C)=C\[C@H](C)[C@@H]1CC=C(OC)C(=O)O1)C(C)(C)C]

To a solution of 70 (77.2 mg, 0.106 mmol) in anhydrous THF (7.5 mL) under N$_2$ and at room temperature, TBAF 1M in THF (0.2 mL, 0.2 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (Hexane/EtOAc 1:2) to give alcohol 71 (25 mg, yield: 44%) as an oil.

$^1$H NMR (CDCl$_3$, 300 MHz) δ: 8.79 (d, 1H, J=9.6 Hz), 7.28-7.22 (m, 1H), 6.85 (t, 1H, J=11.7 Hz), 6.73 (t, 1H, J=9.6 Hz), 6.58 (d, 1H, J=8.7 Hz), 6.12 (d, 1H, J=11.4 Hz), 5.68-5.61 (m, 2H), 5.26 (d, 1H, J=9.9 Hz), 4.86 (q, 1H, J=8.1 Hz), 4.38 (d, 1H, J=9.3 Hz), 4.20-4.18 (m, 1H), 3.78-3.76 (m, 1H), 3.64 (s, 3H), 3.10 (br s, 1H), 2.86-2.79 (m, 1H), 2.41-2.14 (m, 6H), 1.82 (s, 6H), 1.14 (d, 3H, J=6.6 Hz), 1.02 (s, 9H).

Synthesis of Compound 72

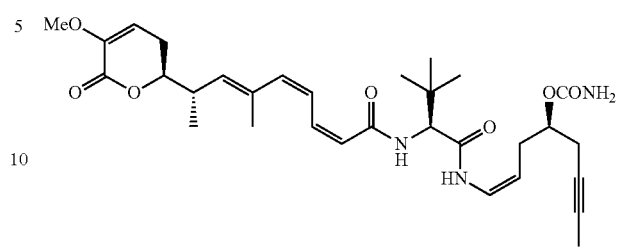

To a solution of 71 (21.6 mg, 0.0443 mmol) in anhydrous DCM (3.1 mL) at 0° C., trichloroacetyl isocyanate (TCAI) (6.4 μl, 0.053 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 1:2). Compound 72 (19.1 mg, yield: 76%) was obtained as a white solid.

$^1$H NMR (CDCl$_3$, 500 MHz) δ: 8.61 (d, 1H, J=11.1 Hz), 7.27 (t, 1H, J=11.4 Hz), 6.92-6.78 (m, 2H), 6.52 (d, 1H, J=9.3 Hz), 6.15 (d, 1H, J=11.4 Hz), 5.69 (d, 1H, J=11.4 Hz), 5.62-5.61 (m, 1H), 5.45 (br s, 2H), 5.28 (d, 1H, J=9.6 Hz), 4.87-4.78 (m, 1H), 4.53-4.45 (m, 1H), 4.42 (d, 1H, J=9.6 Hz), 4.25-4.20 (m, 1H), 3.64 (s, 3H), 2.87-2.80 (m, 1H), 2.44-2.17 (m, 6H), 1.81 (s, 6H), 1.16 (d, 3H, J=6.5 Hz), 1.04 (s, 9H).

Example 15

Scheme 15 provides the synthesis of compound 73.

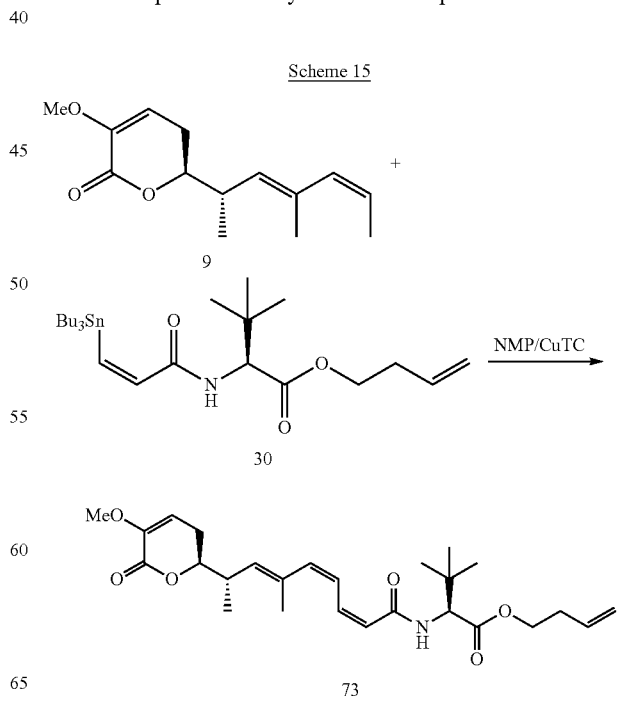

Scheme 15

Synthesis of Compound 73

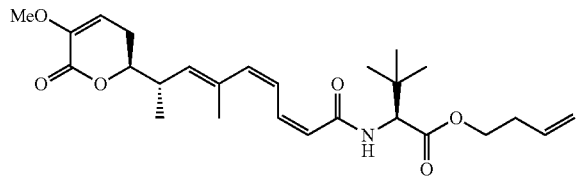 [SMILES: C=CCCOC(=O)[C@@H](NC(=O)\C=C/C=C\C(C)=C\[C@H](C)[C@@H]1CC=C(OC)C(=O)O1)C(C)(C)C]

To a solution of 30 (40 mg, 0.076 mmol) and 9 (31 mg, 0.09 mmol) in NMP (0.8 ml) at 0° C., Copper thiophenecarboxylate (CuTC, 22 mg, 0.11 mmol) was added. The reaction was stirred at 0° C. for 45 min and an hour at room temperature. Then, the crude mixture was filtered through a plug of neutral alumina, washing with EtOAc/Ether 50:50 (20 ml) and the combined filtrates were washed with HCl 0.5N (3×10 ml). After drying and evaporating the solvent under reduced pressure the crude was purified by column chromatography (Ethyl acetate/hexanes, 5:1 to 2:1) to afford pure 73 (6 mg, yield: 17%).

$^1$H NMR (CDCl$_3$, 300 MHz) δ: 7.27 (t, 1H, J=11.46 Hz), 6.90 (t, 1H, J=11.52 Hz), 6.16 (d, 1H, J=11.7), 6.03 (d, 1H, J=9.55 Hz), 5.84-5.70 (m, 1H), 5.67-5.60 (m, 2H), 5.28 (d, 1H, J=10.66 Hz), 5.14-5.06 (m, 2H), 4.53 (d, 1H, J=9.41 Hz), 4.22-4.10 (m, 3H), 3.65 (s, 3H), 2.91-2.81 (m, 1H), 2.47-2.34 (m, 4H), 1.84 (s, 3H), 1.16 (d, 3H, J=6.65 Hz), 0.99 (s, 9H).

Example 16

Scheme 16 provides the synthesis of several compounds of this invention.

Scheme 16

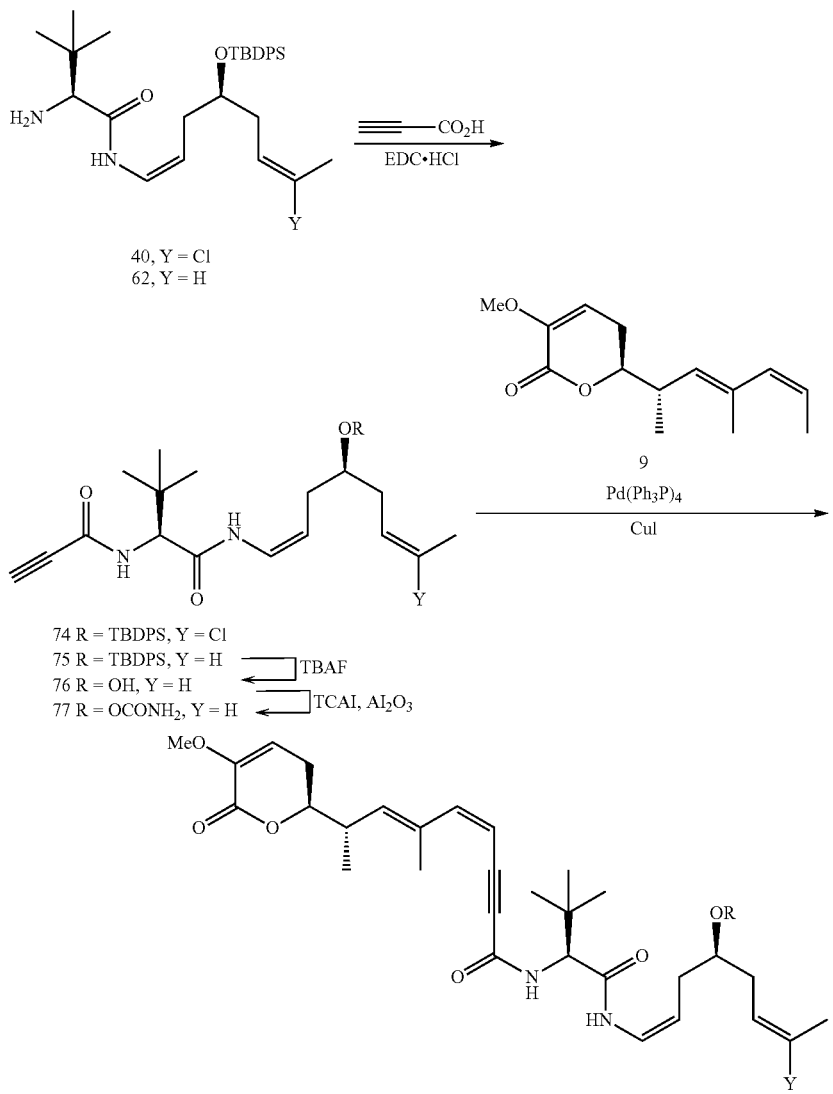

Synthesis of Compound 74

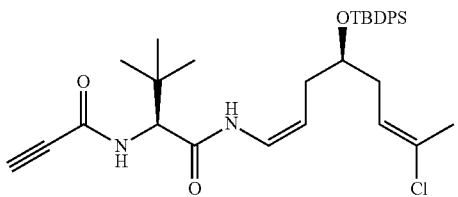

To a solution of 40 (2.7 g, 5.12 mmol) and propiolic acid (0.41 mL, 6.66 mmol) in anhydrous DCM (51 mL) at 0° C., N-(3-dimethylaminopropyl)-N'-ethylcarbodiimide hydrochloride EDC (1.23 g, 6.4 mmol) was added. The reaction was stirred at 0° C. for 30 min and 2 hours at room temperature. Then, the crude mixture was quenched with water and extracted with dichloromethane. The combined filtrates were washed with $H_2O$. After drying and evaporating the solvent under reduced pressure the crude was purified by column chromatography (EtOAc/hexanes mixture) to afford pure compound 74 (2.25 g, 85% yield) as a white solid.

$^1$H NMR (CDCl$_3$, 300 MHz) δ: 7.66 (m, 4H), 7.47-7.36 (m, 6H), 6.96 (d, 1H, J=10.5 Hz), 6.66 (d, 1H, J=9.2 Hz), 6.62 (t, 1H, J=8.9 Hz), 5.52 (t, 1H, J=7.4 Hz), 4.79 (q, 1H, J=8.6 Hz), 4.27 (d, 1H, J=9.4 Hz), 3.83 (m, 1H), 2.82 (s, 1H), 2.19-2.04 (m, 4H), 1.87 (s, 3H), 1.05 (s, 9H), 0.99 (s, 9H).

Synthesis of Intermediate 75

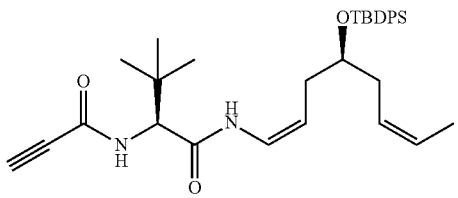

A solution of propiolic acid (45 μl, 0.726 mmol), amine 62 (275 mg, 0.56 mmol) in anhydrous DCM (5.6 mL) was cooled to 0° C. under argon and N-(3-Dimethylaminopropyl)-N'-ethylcarbodiimide hydrochloride, EDC (134 mg, 0.7 mmol) was added. The reaction mixture was stirred at 0° C. for 10 min and then at 23° C. for 3 hours, was quenched with water and extracted with dichloromethane. The combined organic layers were dried (anhydrous Na$_2$SO$_4$), filtered and concentrated. The residue was purified by flash chromatography (EtOAc/hexane 1:10 to 3:1) to afford 75 (260 mg, 85% yield) as a colourless foam solid.

$^1$H NMR (CDCl$_3$, 300 MHz) δ: 7.69-7.67 (m, 4H), 7.44-7.36 (m, 6H), 7.08 (d, 1H, J=10.2 Hz), 6.67-6.61 (m, 2H), 5.53-5.45 (m, 1H), 5.35-5.26 (m, 1H), 4.92-4.84 (m, 1H), 4.26 (d, 1H, J=9.6 Hz), 3.89-3.82 (m, 1H), 2.80 (s, 1H), 2.26-2.05 (m, 4H), 1.44 (d, 3H, J=7.8 Hz), 1.05 (s, 9H), 0.97 (s, 9H).

Synthesis of Intermediate 76

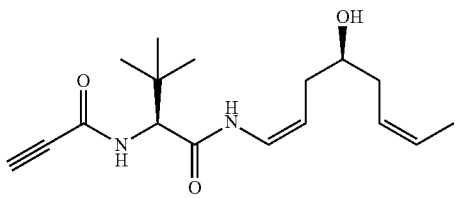 [SMILES: C#CC(=O)N[C@H](C(=O)N/C=C\C[C@@H](O)C/C=C\C)C(C)(C)C]

To a solution of 75 (244.3 mg, 0.45 mmol) in anhydrous THF (5 mL) under N$_2$ and at 0° C., TBAF 1M in THF (0.54 mL, 0.54 mmol) was added. The reaction was stirred at room temperature for 3 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (hexane/EtOAc 4:1 to 1:2) to give alcohol 76 (94.1 mg, 69% yield) as a pale yellow oil.

$^1$H NMR (CDCl$_3$, 300 MHz) δ: 9.02 (d, 1H, J=9.9 Hz), 7.09 (d, 1H, J=9.3 Hz), 6.74 (t, 1H, J=9.9 Hz), 5.65-5.57 (m, 1H), 5.43-5.35 (m, 1H), 4.93-4.85 (m, 1H), 4.44 (d, 1H, J=9.3 Hz), 3.78-3.70 (m, 1H), 2.87 (s, 1H), 2.32-2.12 (m, 4H), 1.61 (d, 3H, J=6.6 Hz), 1.02 (s, 9H).

$^{13}$C NMR (CDCl$_3$, 75 MHz) δ: 167.7, 152.4, 127.7, 126.0, 123.5, 109.4, 77.3, 74.9, 72.1, 61.3, 35.4, 34.7, 33.2, 26.8, 13.3.

Synthesis of Intermediate 77

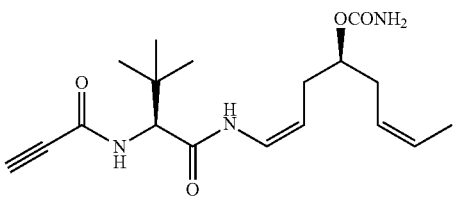

To a solution of 76 (48.6 mg, 0.159 mmol) in anhydrous DCM (1.6 mL) at room temperature, trichloroacetyl isocyanate (TCAI) (23.0 μl, 0.19 mmol) was added. The reaction was stirred at room temperature for 30 min and then neutral aluminium oxide was added (250 mg). The mixture was stirred for 60 min and then was soaked into a pad of aluminium oxide. The product was washed out using a mixture of dichloromethane/MeOH 50:1. The filtrate was evaporated under reduced pressure to give the crude product which was purified by column chromatography (hexane/EtOAc 3:1 to 1:100) affording compound 77 (43 mg, 77% yield) as a white solid.

$^1$H NMR (CDCl$_3$, 300 MHz) δ: 9.02 (d, 1H, J=10.5 Hz), 7.12 (bs, 1H), 7.04 (d, 1H, J=9.6 Hz), 6.98 (bs, 1H), 6.80 (t, 1H, J=9.7 Hz), 5.63-5.53 (m, 1H), 5.42-5.33 (m, 1H), 4.86 (q, 1H, J=8.3 Hz), 4.48-4.30 (m, 1H), 4.39 (d, 1H, J=9.6 Hz), 2.87 (s, 1H), 2.46-2.43 (m, 1H), 2.35-2.30 (m, 2H), 2.18-2.11 (m, 1H), 1.61 (d, 3H, J=6.0 Hz), 1.00 (s, 9H).

Synthesis of Compound 78

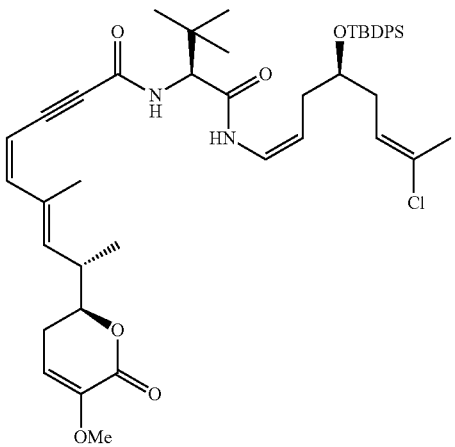

To a solution of iodo compound 9 (300 mg, 0.86 mmol) in diisopropylamine (4.3 mL) under N$_2$ at room temperature, Pd(Ph$_3$P)$_4$ (20 mg, 0.017 mmol) and CuI (6.4 mg, 0.034 mmol) were added. Then, compound 74 (500 mg, 0.86 mmol) was added portionwise and the reaction mixture was stirred at room temperature for 2 hours. The crude was quenched with H$_2$O and extracted with EtOAc. The organic phase was dried (anhydrous Na$_2$SO$_4$) and evaporated under reduced pressure. Purification by column chromatography (Hexane/EtOAc 3:1 to 1:1) afford pure compound 78 (580 mg, yield: 85%) as a yellow solid.

¹H NMR (CDCl₃, 300 MHz) δ: 7.67 (m, 4H), 7.48-7.37 (m, 6H), 7.75 (d, 1H, J=10.5 Hz), 6.65 (t, 1H, J=10.1 Hz), 6.46 (d, 1H J=9.2 Hz), 6.38 (d, 1H, J=12.0 Hz), 5.64-5.48 (m, 3H), 5.43 (d, 1H, J=12.1 Hz), 4.78 (q, 1H, J=7.7 Hz), 4.28 (d, 1H, J=9.3 Hz), 4.20 (m, 1H), 3.82 (m, 1H), 3.65 (s, 3H), 2.86 (m, 1H), 2.40 (m, 2H), 2.14 (m, 4H), 2.09 (s, 3H), 1.86 (s, 3H), 1.15 (d, 3H, J=6.6 Hz), 1.05 (s, 9H), 0.99 (s, 9H).

Synthesis of Compound 79

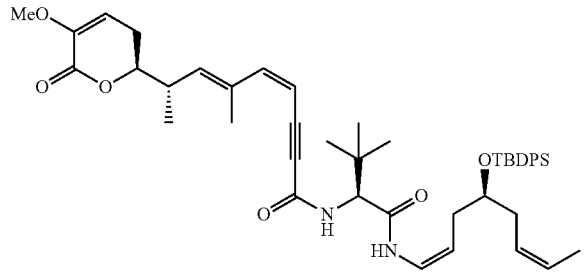

To a solution of 9 (113 mg, 0.325 mmol) in DIPA (1.6 ml) at 23° C., Pd(Ph₃P)₄ (7 mg, 0.006 mmol) and CuI (2.5 mg, 0.013 mmol) were added. Then 75 (195 mg, 0.358 mmol) was added and the reaction was stirred at 23° C. for 3 hours. The crude mixture was quenched with H₂O and extracted with EtOAc. The organic phase was dried (anhydrous Na₂SO₄) and evaporated under reduced pressure. The residue was purified by flash chromatography (EtOAc/hexane 1:3 to 1:1) to afford pure 79 (180 mg, 70% yield) as a colourless foam solid.

¹H NMR (CDCl₃, 300 MHz) δ: 7.67-7.64 (m, 4H), 7.60 (d, 1H, J=10.8 Hz), 7.46-7.35 (m, 6H), 6.66 (t, 1H, J=9.6 Hz), 6.59 (dd, 1H, J=9.9 Hz), 6.31 (d, 1H, J=12.6 Hz), 5.62-5.54 (m, 2H), 5.42-5.37 (m, 1H), 5.32 (d, 1H, J=12.0 Hz), 5.30-5.23 (m, 1H), 4.92-4.84 (m, 1H), 4.42 (d, 1H, J=9.6 Hz), 4.23-4.15 (m, 1H), 3.86-3.78 (m, 1H), 3.63 (s, 3H), 2.88-2.80 (m, 1H), 2.41-2.36 (m, 2H), 2.22-2.11 (m, 4H), 2.06 (s, 3H), 1.39 (d, 3H, J=6.9 Hz), 1.13 (d, 3H, J=6.6 Hz), 1.03 (s, 9H), 0.96 (s, 9H).

¹³C NMR (CDCl₃, 75 MHz) δ: 167.5, 161.7, 153.3, 148.2, 145.4, 138.2, 136.1, 135.7, 134.4, 129.9, 127.8, 127.8, 126.5, 126.1, 121.6, 109.5, 108.5, 103.1, 88.2, 85.1, 81.7, 72.6, 60.8, 55.6, 37.2, 35.6, 34.1, 32.6, 27.2, 26.7, 26.6, 19.5, 16.4, 15.5, 13.1. (One Csp² not located).

Synthesis of Compound 80

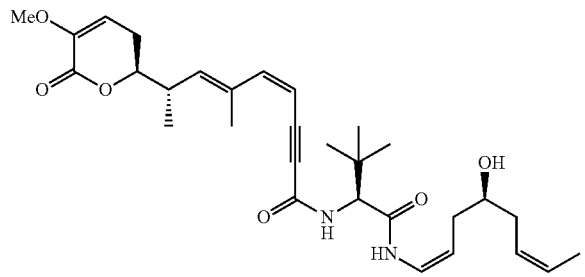 [SMILES: C/C=C\C[C@H](O)C/C=C\NC(=O)[C@@H](NC(=O)C#C/C=C\C(C)=C\[C@H](C)[C@@H]1CC=C(OC)C(=O)O1)C(C)(C)C]

To a solution of 9 (52 mg, 0.15 mmol) in DIPA (0.6 ml) at 23° C., Pd(Ph₃P)₄ (3.5 mg, 0.003 mmol) and CuI (1.14 mg, 0.006 mmol) were added. Then, 76 (45.5 mg, 0.15 mmol) in 0.4 ml of DIPA was added and the reaction was stirred at 23° C. for 120 min. The crude mixture was quenched with H₂O and extracted with EtOAc. The organic phase was dried (anhydrous Na₂SO₄) and evaporated under reduced pressure. The residue was purified by flash chromatography (dichloromethane/MeOH 100:1 to 20:1) to afford pure 80 (59.5 mg, 75% yield) as a colourless oil.

¹H NMR (CDCl₃, 300 MHz) δ: 8.94 (d, 1H, J=9.9 Hz), 6.75 (t, 1H, J=9.3 Hz), 6.69 (d, 1H, J=9.0 Hz), 6.37 (d, 1H, J=12.0 Hz), 5.68-5.57 (m, 3H), 5.44 (d, 1H, J=12.0 Hz), 5.43-5.35 (m, 1H), 4.95-4.87 (m, 1H), 4.34 (d, 1H, J=9.3 Hz), 4.24-4.17 (m, 1H), 3.76 (m, 1H), 3.64 (s, 3H), 2.91-2.78 (m, 1H), 2.63 (bs, 1H), 2.43-2.38 (m, 2H), 2.32-2.11 (m, 4H), 2.07 (s, 3H), 1.62 (d, 3H, J=6.6 Hz), 1.14 (d, 3H, J=6.6 Hz), 1.01 (s, 9H).

¹³C NMR (CDCl₃, 125 MHz) δ: 167.5, 161.5, 153.2, 147.9, 145.1, 137.8, 135.4, 127.8, 125.5, 123.6, 109.0, 108.3, 103.0, 88.0, 84.7, 81.4, 72.0, 61.1, 55.4, 37.0, 35.2, 34.5, 32.8, 26.6, 26.4, 16.2, 15.3, 13.0.

MS (ES) [m/z]=549.2 [M+Na]⁺.

Synthesis of Compound 81

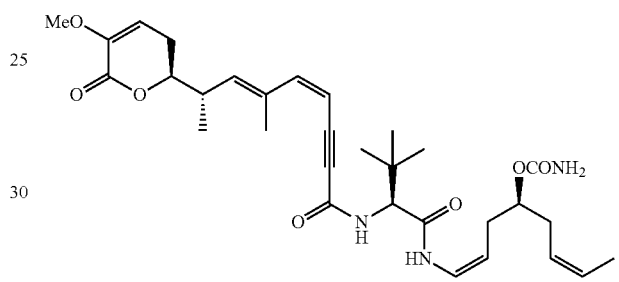

To a solution of 9 (43 mg, 0.123 mmol) in DIPA (0.6 ml) at 23° C., Pd(Ph₃P)₄ (2.8 mg, 0.0025 mmol) and CuI (1.0 mg, 0.005 mmol) were added. Then, 77 (43 mg, 0.123 mmol) in 0.4 ml of DIPA was added and the reaction was stirred at 23° C. for 120 min. The crude mixture was quenched with H₂O and extracted with EtOAc. The organic phase was dried (anhydrous Na₂SO₄) and evaporated under reduced pressure. The residue was purified by flash chromatography (dichloromethane/MeOH 100:1 to 20:1) to afford pure 81 (38 mg, 54% yield) as a colourless oil.

¹H NMR (CDCl₃, 300 MHz) δ: 9.00 (d, 1H, J=10.8 Hz), 6.81 (t, 1H, J=9.6 Hz), 6.73 (d, 1H, J=9.6 Hz), 6.38 (d, 1H, J=12.0 Hz), 5.63-5.56 (m, 5H), 5.45 (d, 1H, J=11.7 Hz), 5.43-5.36 (m, 1H), 4.90-4.81 (m, 1H), 4.40 (d, 1H, J=9.3 Hz), 4.40-4.33 (m, 1H), 4.24-4.17 (m, 1H), 3.64 (s, 3H), 2.90-2.82 (m, 1H), 2.42-2.31 (m, 5H), 2.18-2.09 (m, 1H), 2.09 (s, 3H), 1.62 (d, 3H, J=6.6 Hz), 1.15 (d, 3H, J=6.6 Hz), 1.01 (s, 9H).

Example 17

Scheme 17 provides the synthesis of several compounds of this invention

Scheme 17

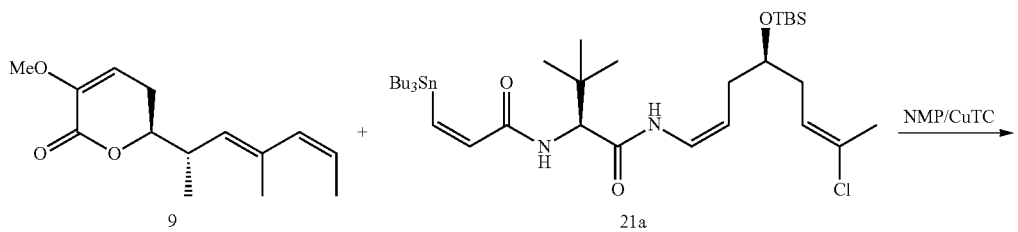

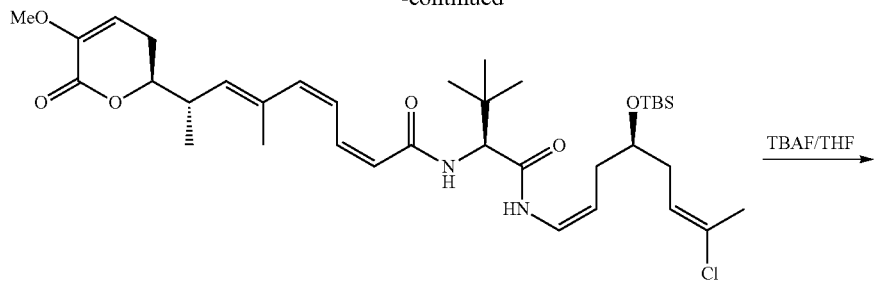

82

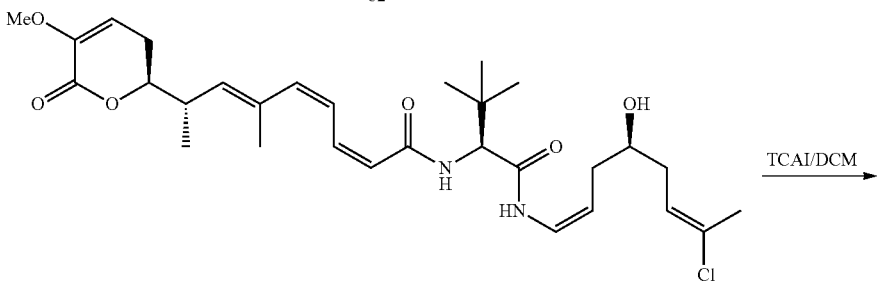

83

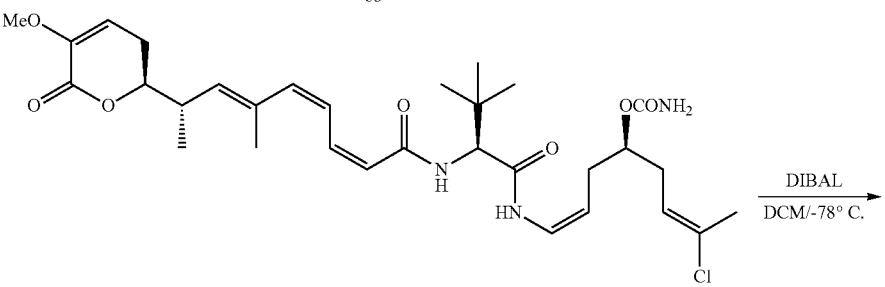

84

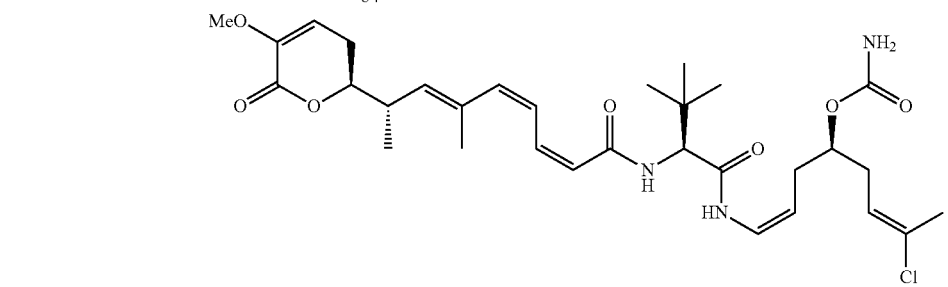

85

Synthesis of Compound 82

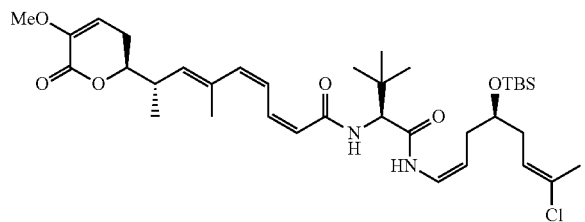 [SMILES: COC1=CC[C@@H]([C@@H](C)/C=C(C)/C=C\C=C/C(=O)N[C@H](C(=O)N/C=C\C[C@H](C/C=C(\C)Cl)O[Si](C)(C)C(C)(C)C)C(C)(C)C)OC1=O]

To a solution of alkenylstannane 21a (1.1 g, 1.47 mmol) and 9 (0.62 g, 1.77 mmol) in 1-methyl-2-pyrrolidinone (NMP) (14.7 mL) at 0° C., Copper thiophenecarboxylate (CuTC) (422 mg, 2.2 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×15 mL). The organic solution was dried and evaporated to give the crude product which was purified by column chromatography (Hexane/EtOAc 5:1 to 1:1) to give triene 82 (0.66 g, yield: 66%) as an oil.

$^1$H NMR (CDCl$_3$, 300 MHz) δ: 7.89 (d, 1H, J=10.8 Hz), 7.22 (dd, 1H, J=12.3, 11.4 Hz), 6.86 (dd, 1H, J=11.7, 11.4 Hz), 6.70 (dd, 1H, J=9.9, 9.3 Hz), 6.35 (d, 1H, J=9.3 Hz), 6.13 (d, 1H, J=11.4 Hz), 5.66 (d, 1H, J=11.4 Hz), 5.60 (dd, 1H, J=5.4, 3.9 Hz), 5.55 (br t, 1H, J=7.8 Hz), 5.26 (d, 1H, J=10.2 Hz), 4.84-4.76 (m, 1H), 4.3 (d, 1H, J=9.3 Hz), 4.20-4.16 (m, 1H), 3.77-3.69 (m, 1H), 3.63 (s, 3H), 2.89-2.77 (m, 1H), 2.41-2.33 (m, 2H), 2.19-2.13 (m, 4H), 2.00 (s, 3H), 1.82 (s, 3H), 1.13 (d, 3H, J=6.9 Hz), 1.02 (s, 9H), 0.86 (s, 9H), 0.4 (s, 3H), 0.03 (s, 3H).

$^{13}$C NMR (CDCl$_3$, 75 MHz) δ: 168.5, 166.4, 161.8, 145.4, 140.3, 137.3, 134.4, 134.3, 131.0, 124.3, 124.1, 122.4, 121.2,

Synthesis of Compound 83

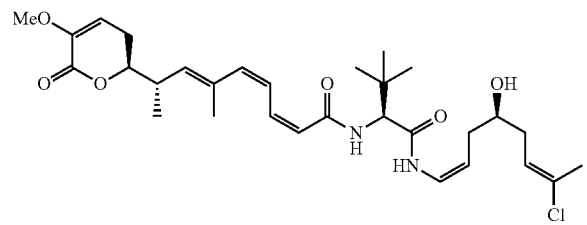 [SMILES: COC1=CC[C@@H]([C@@H](C)/C=C(C)/C=C\C=C/C(=O)N[C@H](C(=O)N/C=C\C[C@@H](O)C/C=C(\C)Cl)C(C)(C)C)OC1=O]

To a solution of 82 (275 mg, 0.41 mmol) in anhydrous THF (6 mL) under N$_2$ and at room temperature, TBAF 1M in THF (0.82 mL, 0.82 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (Hexane/EtOAc 3:1 to 1:2) to give alcohol 83 (175 mg; yield: 76%) as a white solid.

$^1$H NMR (CDCl$_3$, 300 MHz) δ: 9.00 (d, 1H, J=10.2 Hz), 7.25 (dd, 1H, J=12.0, 11.4 Hz), 6.86 (dd, 1H, J=11.7, 11.4 Hz), 6.72 (dd, 1H, J=9.6, 8.7 Hz), 6.68 (d, 1H, J=8.7 Hz), 6.13 (d, 1H, J=11.7 Hz), 5.68 (d, 1H, J=11.4 Hz), 5.63-5.58 (m, 2H), 5.27 (d, 1H, J=10.2 Hz), 4.85-4.76 (m, 1H), 4.42 (d, 1H, J=9.3 Hz), 4.25-4.17 (m, 1H), 3.70-3.69 (m, 1H), 3.63 (s, 3H), 3.48 (br s, 1H), 2.89-2.75 (m, 1H), 2.42-2.36 (m, 2H), 2.22-2.11 (m, 4H), 2.04 (s, 3H), 1.82 (s, 3H), 1.14 (d, 3H, J=6.6 Hz), 1.03 (s, 9H).

Synthesis of Compound 84

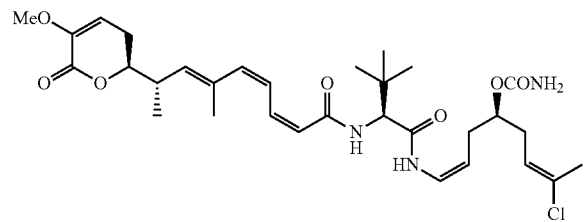

To a solution of 83 (300 mg, 0.53 mmol) in anhydrous DCM (7.5 mL) at 0° C., trichloroacetyl isocyanate (TCAI) (76 μl, 0.64 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 2:1 to 1:2) to give compound 84 (0.26 g, yield: 81%) as a white solid.

$^1$H NMR (CDCl$_3$, 300 MHz) δ: 8.78 (d, 1H, J=10.8 Hz), 7.30 (dd, 1H, J=11.6, 11.6 Hz), 6.91 (dd, 1H, J=11.6, 11.6 Hz), 6.84 (br dd, 1H, J=10.8, 9.7 Hz), 6.51 (d, 1H, J=9.5 Hz), 6.17 (d, 1H, J=11.6 Hz), 5.70 (d, 1H, J=11.6 Hz), 5.63 (dd, 1H, J=6.5, 2.6 Hz), 5.61 (br t, 1H, J=6.8 Hz), 5.29 (d, 1H, J=9.8 Hz), 4.80 (m, 1H), 4.41 (m, 1H), 4.41 (d, 1H, J=9.5 Hz), 4.24 (ddd, 1H, J=11.5, 7.1, 4.1 Hz), 3.66 (s, 3H), 2.85 (ddq, 1H, J=9.8, 7.1, 6.7 Hz), 2.46 (m, 1H), 2.45 (ddd, 1H, J=17.3, 11.5, 2.6 Hz), 2.37 (ddd, 1H, J=17.3, 6.5, 4.1 Hz), 2.33 (m, 2H), 2.09 (ddd, 1H, J=14.1, 8.4, 8.1 Hz), 2.06 (s, 3H), 1.82 (s, 3H), 1.15 (d, 3H, J=6.7 Hz), 1.04 (s, 9H).
$^{13}$C NMR (CDCl$_3$, 75 MHz) δ: 168.2, 166.3, 161.6, 157.2, 145.2, 140.2, 137.6, 134.1, 133.7, 132.0, 124.6, 124.5, 122.4, 120.7, 108.2, 105.0, 81.9, 74.9, 60.8, 55.4, 37.1, 34.7, 33.0, 30.7, 26.7, 26.1, 21.0, 17.1, 16.3.

Synthesis of Compound 85

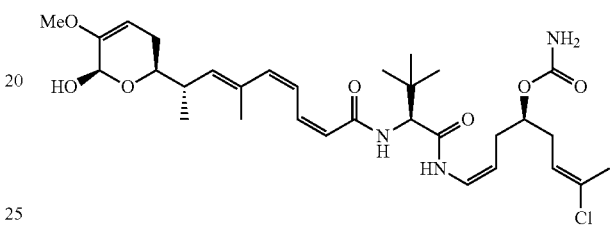

Over a −78° C. cooled solution of compound 84 (10 mg, 0.016 mmol) in anhydrous dichloromethane (0.3 mL) under argon atmosphere, Diisobutylaluminum hydride (DIBAL) 1M in toluene (0.02 mL, 0.02 mol) was added and the mixture was stirred at −78° C. After 2 hours the reaction was quenched with a saturated aqueous solution of NH$_4$Cl and diluted with dichloromethane (2 mL). This mixture was stirred for 0.5 h at room temperature and then the organic layer was decanted. The aqueous residue was extracted with additional dichloromethane (2×4 mL) and the combined organic layers were dried (anhydrous Na$_2$SO$_4$) and the solvent was evaporated. The crude was purified by column chromatography (hexane/EtOAc 2:1 to 1:2) to give compound 85 (5 mg, 50% yield) as a colourless oil.

$^1$H NMR (CDCl$_3$, 300 MHz) δ: 8.57 (d, 1H, J=10.9 Hz), 7.19 (t, 1H, J=11.3 Hz), 6.92 (t, 1H, J=11.4 Hz), 6.82 (t, 1H, J=9.3 Hz), 6.38 (d, 1H, J=9.5 Hz), 6.18 (d, 1H, J=11.5 Hz), 5.64 (d, 1H, J=11.2 Hz), 5.60 (m, 1H), 5.35 (d, 1H, J=10.0 Hz), 5.27 (d, 1H, J=3.1 Hz), 4.81 (m, 2H), 4.46 (m, 1H), 4.40 (d, 1H, J=9.5 Hz), 3.85 (m, 1H), 3.57 (s, 3H), 3.21 (d, 1H, J=3.1 Hz), 2.61 (m, 1H), 2.46-2.29 (m, 3H), 2.14-2.08 (m, 3H), 2.06 (s, 3H), 1.81 (s, 3H), 1.08 (d, 3H, J=6.7 Hz), 1.05 (s, 9H).

Example 18

Scheme 18 provides the synthesis of several compounds of this invention

Scheme 18

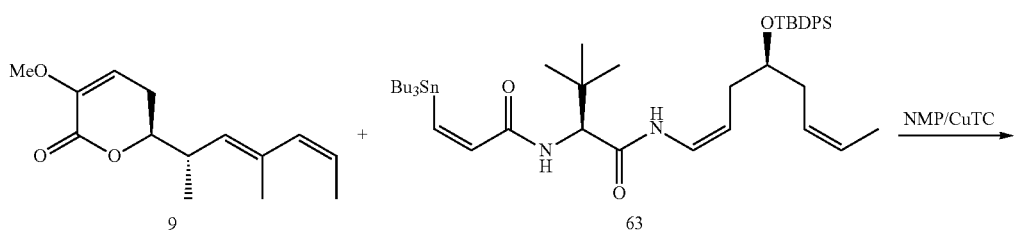

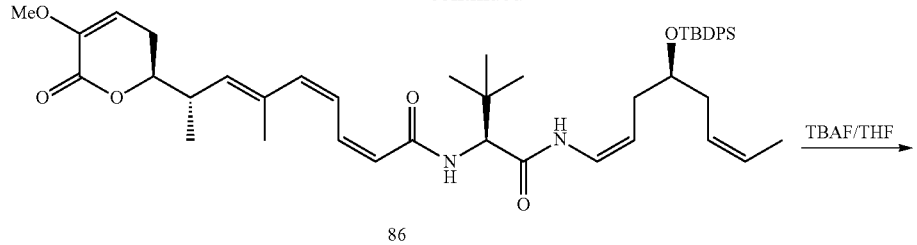

86

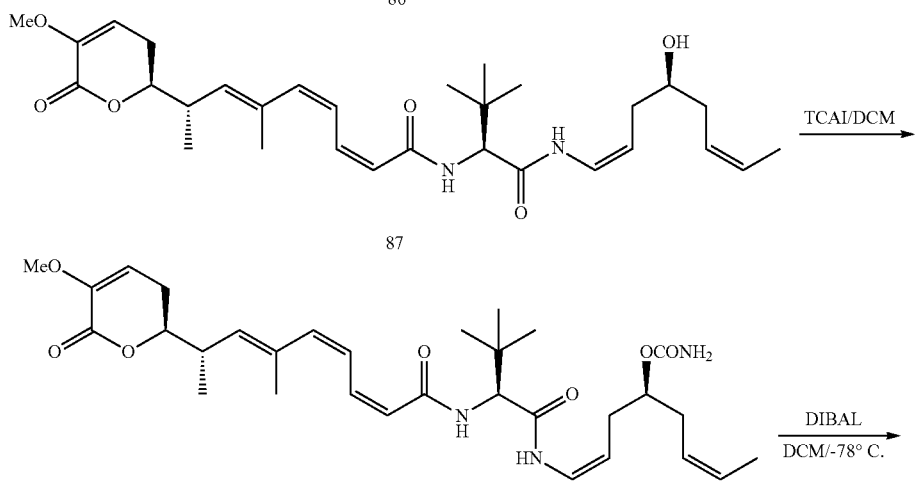

87

88

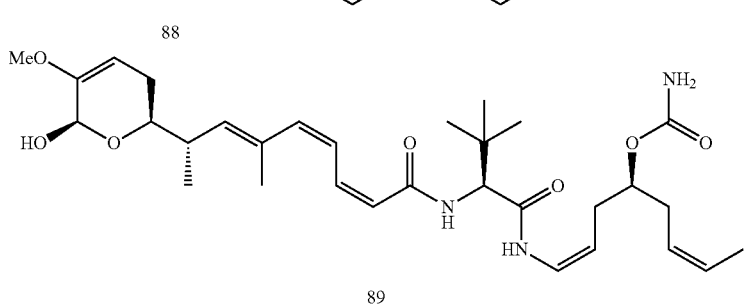

89

Synthesis of Compound 86

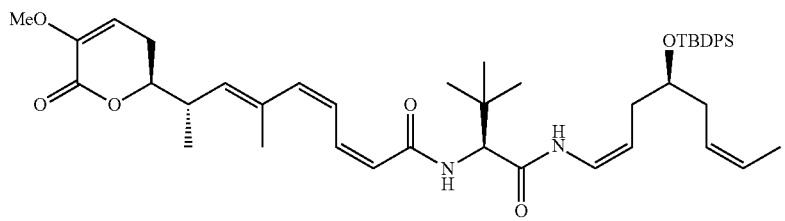

To a solution of alkenylstannane 63 (780.4 mg, 0.904 mmol) and 9 (377.4 mg, 1.085 mmol) in NMP (9 mL) at 0° C., Copper thiophenecarboxylate (258.5 mg, 1.36 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 5:1 to 1:1) to give triene 86 (459.7 mg, yield: 66%) as an oil.

$^1$H NMR (CDCl$_3$, 300 MHz) δ: 7.66-7.64 (m, 4H), 7.43-7.32 (m, 7H), 7.23 (t, 1H, J=11.7 Hz), 6.85 (t, 1H, J=11.7 Hz), 6.62 (dd, 1H, J=10.5, 9.3 Hz), 6.41 (d, 1H, J=9.3 Hz), 6.11 (d, 1H, J=11.7 Hz), 5.66 (d, 1H, J=11.4 Hz), 5.60 (dd, 1H, J=5.7, 5.1 Hz), 5.49-5.41 (m, 1H), 5.32-5.27 (m, 1H), 5.25 (d, 1H, J=9.9 Hz), 4.83-4.75 (m, 1H), 4.32 (d, 1H, J=9.3 Hz), 4.22-4.15 (m, 1H), 3.83-3.78 (m, 1H), 3.62 (s, 3H), 2.86-2.78 (m, 1H), 2.40-2.35 (m, 2H), 2.20-2.04 (m, 4H), 1.81 (s, 3H), 1.40 (d, 3H, J=6.9 Hz), 1.13 (d, 3H, J=6.9 Hz), 1.03 (s, 9H), 0.97 (s, 9H).

$^{13}$C NMR (CDCl$_3$, 75 MHz) δ: 168.3, 166.3, 161.8, 145.4, 140.2, 137.3, 136.1, 134.8, 134.4, 134.3, 129.9, 127.8, 126.4, 126.1, 124.4, 121.7, 121.2, 108.4, 109.1, 82.0, 72.6, 60.6, 55.6, 37.5, 35.2, 32.7, 31.1, 27.2, 26.8, 26.5, 19.5, 17.4, 16.9, 13.1.

Synthesis of Compound 87

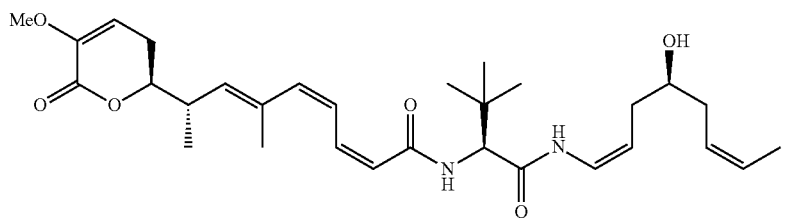 [SMILES: C/C=C\C[C@H](O)C/C=C\NC(=O)[C@@H](NC(=O)\C=C/C=C\C(C)=C\[C@H](C)[C@@H]1CC=C(OC)C(=O)O1)C(C)(C)C]

To a solution of 86 (586 mg, 0.76 mmol) in anhydrous THF (7.5 mL) under $N_2$ and at room temperature, TBAF 1M in THF (1.53 mL, 2 mmol) was added. The reaction was stirred at room temperature for 18 hours and then quenched with a saturated aqueous solution of $NH_4Cl$ and extracted with EtOAc. The combined organic phases were dried over anhydrous $Na_2SO_4$, filtered and concentrated. The residue was purified by flash chromatography (Hexane/EtOAc 3:1 to 1:2) to give alcohol 87 (320 mg, yield: 80%) as a white solid.

$^1$H NMR (CDCl$_3$, 300 MHz) δ: 8.95 (d, 1H, J=10.2 Hz), 7.25 (t, 1H, J=12.0 Hz), 6.85 (t, 1H, J=11.7 Hz), 6.73 (t, 1H, J=9.6 Hz), 6.57 (d, 1H, J=8.7 Hz), 6.12 (d, 1H, J=11.4 Hz), 5.67 (d, 1H, J=11.4 Hz), 5.61 (dd, 1H, J=5.4, 3.9 Hz), 5.63-5.58 (m, 1H), 5.44-5.35 (m, 1H), 5.26 (d, 1H, J=9.9 Hz), 4.86 (q, 1H, J=8.1 Hz), 4.38 (d, 1H, J=9.3 Hz), 4.24-4.16 (m, 1H), 3.81-3.71 (m, 1H), 3.64 (s, 3H), 2.96-2.92 (m, 1H), 2.86-2.79 (m, 1H), 2.41-2.37 (m, 2H), 2.28-2.14 (m, 4H), 1.82 (s, 3H), 1.61 (d, 3H, J=6.6 Hz), 1.14 (d, 3H, J=6.6 Hz), 1.02 (s, 9H).

$^{13}$C NMR (CDCl$_3$, 75 MHz) δ: 168.7, 166.6, 161.8, 145.4, 140.3, 137.5, 134.4, 134.3, 127.7, 126.0, 124.4, 123.7, 121.1, 108.9, 108.4, 82.0, 72.1, 60.9, 55.7, 37.6, 35.0, 34.8, 33.2, 26.9, 26.5, 17.4, 16.9, 13.3.

Synthesis of Compound 88

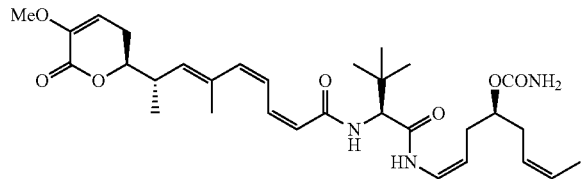

To a solution of 87 (56 mg, 0.105 mmol) in anhydrous DCM (1 mL) at 0° C., trichloroacetyl isocyanate (15 μL, 0.126 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 1:2) to give a compound 88 (57.6 mg, yield: 96%) as a white foam.

$^1$H NMR (CDCl$_3$, 300 MHz) δ: 8.69 (d, 1H, J=10.4 Hz), 7.31 (dd, 1H, J=11.6, 11.6 Hz), 6.90 (dd, 1H, J=11.6, 11.6 Hz), 6.82 (ddd, 1H, J=10.4, 9.1, 0.9 Hz), 6.53 (d, 1H, J=9.6 Hz), 6.15 (d, 1H, J=11.6 Hz), 5.72 (br d, 1H, J=11.6 Hz), 5.63 (dd, 1H, J=6.6, 2.7 Hz), 5.60 (m, 1H), 5.40 (m, 1H), 5.29 (d, 1H, J=9.9 Hz), 4.82 (m, 1H), 4.45 (m, 1H), 4.44 (d, 1H, J=9.6 Hz), 4.25 (ddd, 1H, J=11.3, 7.0, 4.0 Hz), 3.66 (s, 3H), 2.85 (ddq, 1H, J=9.9, 7.0, 6.7 Hz), 2.46 (m, 1H), 2.44 (m, 1H), 2.39 (m, 1H), 2.35 (m, 2H), 2.12 (ddd, 1H, J=14.1, 8.0, 8.0 Hz), 1.82 (s, 3H), 1.63 (dd, 3H, J=6.8, 1.0 Hz), 1.15 (d, 3H, J=6.7 Hz), 1.04 (s, 9H).

$^{13}$C NMR (CDCl$_3$, 75 MHz) δ: 168.2, 166.3, 161.6, 157.6, 145.2, 140.2, 137.5, 134.1, 133.8, 127.1, 124.9, 124.4, 124.2, 120.8, 108.2, 105.8, 81.9, 75.6, 60.7, 55.4, 37.1, 34.8, 31.4, 30.9, 26.7, 26.1, 17.1, 16.4, 13.0.

Synthesis of Compound 89

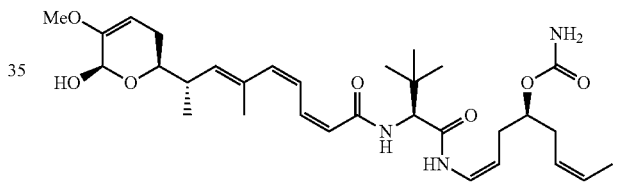

Over a −78° C. cooled solution of compound 88 (15 mg, 0.0262 mmol) in anhydrous dichloromethane (0.5 mL) under argon atmosphere, Diisobutylaluminum hydride (DIBAL) 1M in toluene (0.03 mL, 0.034 mol) was added and the mixture was stirred at −78° C. After 2 hours the reaction was quenched with a saturated aqueous solution of $NH_4Cl$ and diluted with dichloromethane (2 mL). This mixture was stirred for 0.5 h at room temperature and then the organic layer was decanted. The aqueous residue was extracted with additional dichloromethane (2×4 mL) and the combined organic layers were dried (anhydrous $Na_2SO_4$) and the solvent was evaporated to give compound 89 (12 mg, 80% yield) without further purification.

$^1$H NMR (CDCl$_3$, 500 MHz) δ: 8.67 (d, 1H, J=10.7 Hz), 7.17 (m, 1H), 6.92 (t, 1H, J=11.4 Hz), 6.81 (t, 1H, J=9.6 Hz), 6.44 (d, 1H, J=9.5 Hz), 6.18 (d, 1H, J=11.5 Hz), 5.65 (d, 1H, J=11.4 Hz), 5.59 (m, 1H), 5.40 (m, 1H), 5.35 (d, 1H, J=10.0 Hz), 5.27 (s, 1H), 4.83 (q, 1H, J=8.3 Hz), 4.80 (m, 1H), 4.46 (m, 1H), 4.40 (d, 1H, J=9.6 Hz), 3.85 (m, 1H), 3.57 (s, 3H), 3.27 (s, 1H), 2.61 (m, 1H), 2.42 (m, 2H), 2.15-1.99 (m, 4H), 1.83 (s, 3H), 1.63 (d, 3H, J=6.7 Hz), 1.08 (d, 3H, J=6.6 Hz), 1.04 (s, 9H).

Example 19
Scheme 19 provides the synthesis of several compounds of this invention
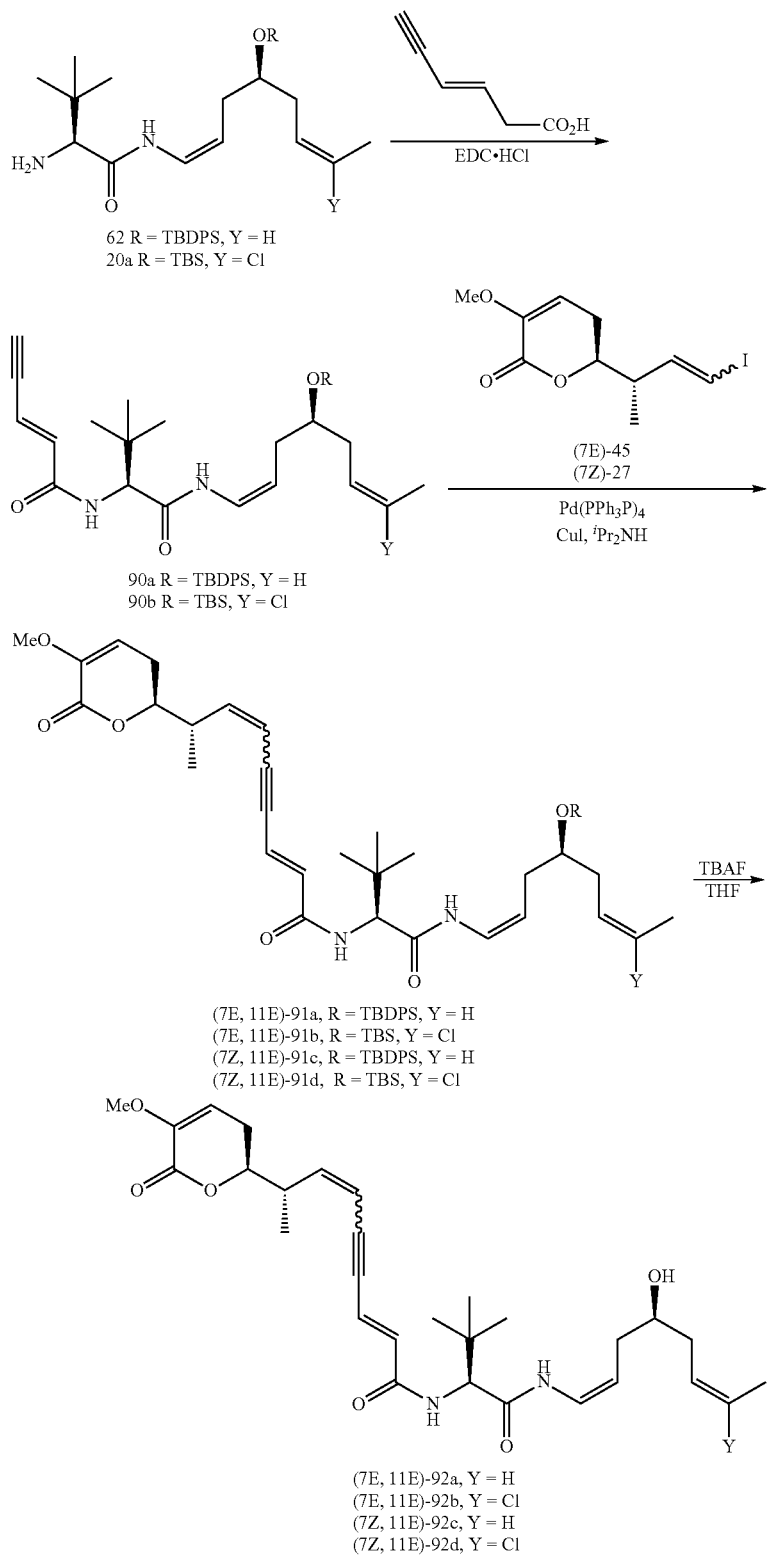

Synthesis of Intermediate 90a

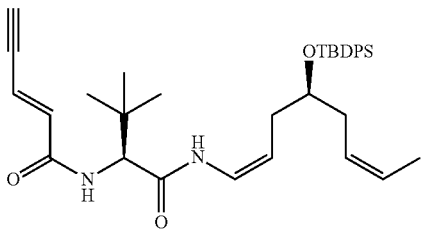

A solution of (E)-pent-2-en-4-ynoic acid (52 mg, 0.54 mmol), amine 62 (232 mg, 0.47 mmol) in anhydrous DCM (5 mL) was cooled to 0° C. under argon and N-(3-Dimethylaminopropyl)-N'-ethylcarbodiimide hydrochloride, EDC (100 mg, 0.52 mmol) was added. The reaction mixture was stirred at 0° C. for 10 min and then at 23° C. for 90 min, was quenched with a saturated aqueous solution of NH$_4$Cl and extracted with dichloromethane. The combined organic layers were dried (anhydrous Na$_2$SO$_4$), filtered and concentrated to afford 90a (223 mg, 83% yield) as a colourless foam solid, which was used without further purification.

$^1$H NMR (CDCl$_3$, 300 MHz) δ: 7.69-7.67 (m, 4H), 7.44-7.36 (m, 6H), 7.11 (d, 1H, J=10.8 Hz), 6.72-6.60 (m, 2H), 6.42 (d, 1H J=8.1 Hz), 6.41 (d, 1H J=15.6 Hz), 5.54-5.45 (m, 1H), 5.36-5.27 (m, 1H), 4.89-4.81 (m, 1H), 4.30 (d, 1H, J=9.3 Hz), 3.89-3.79 (m, 1H), 3.25 (bs, 1H), 2.25-2.02 (m, 4H), 1.45 (d, 3H, J=6.3 Hz), 1.05 (s, 9H), 0.97 (s, 9H).

MS (ES) [m/z]=593.3 [M+Na]$^+$.

$^{13}$C NMR (CDCl$_3$, 125 MHz) δ: 167.7, 164.1, 135.8, 134.4, 134.1, 129.7, 129.7, 127.6, 127.6, 126.4, 125.8, 121.4, 121.1, 109.2, 84.6, 80.5, 72.3, 60.7, 35.3, 33.8, 32.4, 29.7, 27.0, 26.5, 19.3, 12.9.

Synthesis of Intermediate 90b

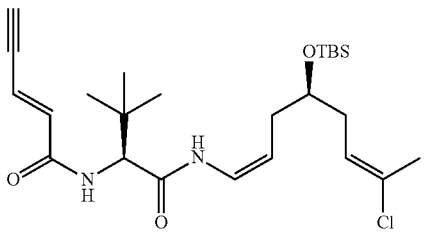 [SMILES: C#C/C=C/C(=O)N[C@H](C(=O)N/C=C\C[C@H](C/C=C(\C)Cl)O[Si](C)(C)C(C)(C)C)C(C)(C)C]

To a solution of amine 20a (96.04 mg, 0.24 mmol) and (E)-pent-2-en-4-ynoic acid (27.4 mg, 0.28 mmol) in dry dichloromethane/DMF (10:1, 3.3 mL), under argon atmosphere and at 0° C., DIPEA (0.049 mL, 0.28 mmol), HOAt (38.11 mg, 0.28 mmol), and HATU (106.4 mg, 0.28 mmol) were added to the solution and after 30 min, the cold bath was removed. The reaction mixture was stirred at room temperature for 2 h, quenched with a saturated aqueous solution of NH$_4$Cl, poured into water and extracted with dichloromethane. The combined organic phases were dried over anhydrous Na$_2$SO$_4$, filtered and concentrated. The residue was purified by flash chromatography (hexane/EtOAc 20:1 to 10:1) to give amide 90b (81.9 mg, 71% yield) as a white foam.

$^1$H NMR (CDCl$_3$, 300 MHz) δ: 7.91 (d, 1H, J=10.2 Hz), 6.74-6.63 (m, 3H), 6.48 (d, 1H, J=15.6 Hz), 5.58-5.53 (m, 1H), 4.89-4.81 (m, 1H), 4.48 (d, 1H, J=9.3 Hz), 3.77-3.73 (m, 1H), 3.25 (d, 1H, J=9.3 Hz), 2.18-2.09 (m, 4H), 2.01 (s, 3H), 1.02 (s, 9H), 0.87 (s, 9H), 0.06 (s, 3H), 0.04 (s, 3H).

$^{13}$C NMR (CDCl$_3$, 75 MHz) δ: 168.3, 164.4, 134.7, 131.7, 133.9, 122.5, 121.3, 109.1, 84.8, 80.8, 71.6, 61.0, 36.5, 35.4, 33.8, 26.8, 26.0, 21.2, 18.3, -4.3, -4.4.

Synthesis of Compound 91a

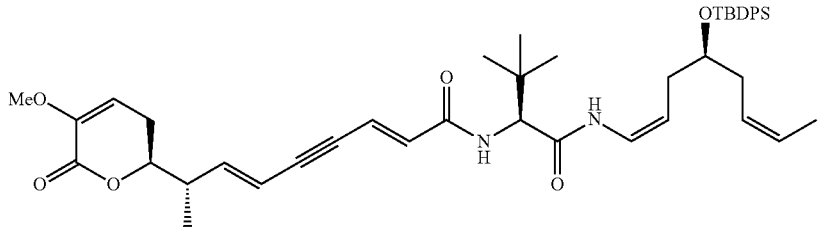

To a solution of 45 (56.2 mg, 0.182 mmol) in DIPA (1.6 ml) at 23° C., Pd(Ph$_3$P)$_4$ (15.7 mg, 0.014 mmol) and CuI (5.2 mg, 0.028 mmol) were added. Then, 90a (114.6 mg, 0.200 mmol) in 0.4 ml of DIPA was added and the reaction was stirred at 23° C. for 90 min. The crude mixture was quenched with H$_2$O and extracted with EtOAc. The organic phase was dried (anhydrous Na$_2$SO$_4$) and evaporated under reduced pressure. The residue was purified by flash chromatography (EtOAc/hexanes 1:4 to 6:1) to afford pure 91a (96 mg, 70% yield) as a colourless oil.

$^1$H NMR (CDCl$_3$, 300 MHz) δ: 7.68-7.66 (m, 4H), 7.46-7.35 (m, 6H), 7.11 (d, 1H, J=10.8 Hz), 6.81 (dd, 1H, J=15.3, 2.1 Hz), 6.30 (dd, 1H, J=10.2, 9.3 Hz), 6.32 (d, 1H, J=9.3 Hz), 6.25 (d, 1H, J=15.3 Hz), 6.15 6.32 (dd, 1H, J=15.9, 8.4 Hz), 5.74 (d, 1H, J=15.9 Hz), 5.62 (dd, 1H, J=6.3, 3.0 Hz), 5.54-5.46 (m, 1H), 5.30-5.27 (m, 1H), 4.84-4.82 (m, 1H), 4.30 (d, 1H, J=9.3 Hz), 4.28-4.21 (m, 1H), 3.86-3.82 (m, 1H), 3.65 (s, 3H), 2.68-2.62 (m, 1H), 2.43-2.36 (m, 2H), 2.22-2.04 (m, 4H), 1.43 (d, 3H, J=6.6 Hz), 1.18 (d, 3H, J=6.9 Hz), 1.04 (s, 9H), 0.96 (s, 9H).

$^{13}$C NMR (CDCl$_3$, 125 MHz) δ: 167.7, 164.3, 161.3, 145.5, 145.2, 135.2, 134.1, 131.8, 129.8, 129.7, 127.6, 127.6, 126.4, 125.8, 122.2, 121.4, 111.3, 109.1, 108.0, 95.1, 86.7, 80.8, 72.3, 60.7, 55.4, 41.5, 35.2, 33.8, 32.4, 29.7, 27.0, 26.5, 25.9, 19.3, 15.5, 12.9.

Synthesis of Compound 91b

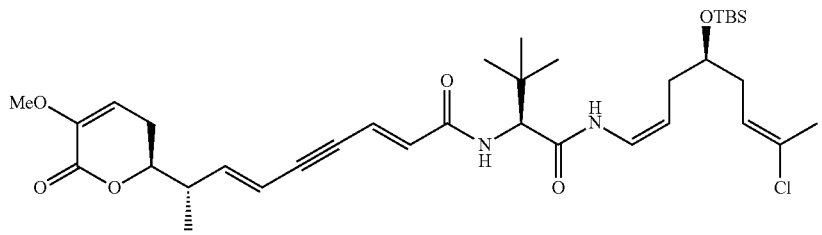 [SMILES: COC1=CC[C@@H]([C@@H](C)/C=C/C#C/C=C/C(=O)N[C@H](C(=O)N/C=C\C[C@H](C/C=C(\C)Cl)O[Si](C)(C)C(C)(C)C)C(C)(C)C)OC1=O]

To a solution of 45 (30.2 mg, 0.098 mmol) in DIPA (0.5 ml) at 23° C., Pd(Ph$_3$P)$_4$ (8 mg, 0.007 mmol) and CuI (3 mg, 0.014 mmol) were added. Then, 90b (47.6 mg, 0.098 mmol) in 0.5 ml of DIPA was added and the reaction was stirred at 23° C. for 90 min. The crude mixture was quenched with H$_2$O and extracted with EtOAc. The organic phase was dried (anhydrous Na$_2$SO$_4$) and evaporated under reduced pressure. The residue was purified by flash chromatography (EtOAc/hexanes 1:4 to 1:1) to afford pure 91b (41.2 mg, 64% yield) as a colourless oil.

$^1$H NMR (CDCl$_3$, 300 MHz) δ: 7.70 (d, 1H, J=10.2 Hz), 6.82 (dd, 1H, J=15.3, 2.4 Hz), 6.72 (t, 1H, J=9.5 Hz), 6.28 (d, 1H, J=9.0 Hz), 6.25 (d, 1H, J=15.3 Hz), 6.15 (dd, 1H, J=15.9, 8.1 Hz), 5.74 (d, 1H, J=15.9 Hz), 5.63 (dd, 1H, J=6.3, 3.0 Hz), 5.62-5.55 (m, 1H), 4.89-4.81 (m, 1H), 4.38 (d, 1H, J=9.6 Hz), 4.30-4.23 (m, 1H), 3.79-3.75 (m, 1H), 3.65 (s, 3H), 2.69-2.61 (m, 1H), 2.44-2.32 (m, 2H), 2.20-2.14 (m, 4H), 2.02 (s, 3H), 1.18 (d, 3H, J=6.6 Hz), 1.02 (s, 9H), 0.87 (s, 9H), 0.07 (s, 3H), 0.05 (s, 3H).

$^{13}$C NMR (CDCl$_3$, 75 MHz) δ: 168.1, 164.6, 161.5, 145.7, 145.4, 132.1, 131.2, 123.9, 122.4, 111.5, 108.9, 108.2, 95.4, 86.9, 81.0, 71.7, 61.0, 55.7, 41.7, 36.5, 35.4, 33.8, 29.9, 26.8, 26.2, 26.1, 21.3, 18.3, 15.7, −4.3, −4.4.

Synthesis of Compound 91c

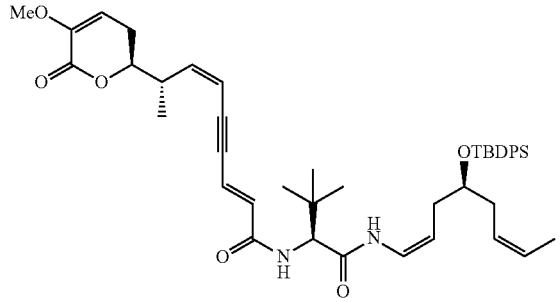

To a solution of 27 (58 mg, 0.188 mmol) in DIPA (1.6 mL) at 23° C., Pd(Ph$_3$P)$_4$ (16.3 mg, 0.014 mmol) and CuI (5.3 mg, 0.028 mmol) were added. Then, 90a (118.2 mg, 0.207 mmol) in 0.4 ml of DIPA was added and the reaction was stirred at 23° C. for 90 min. The crude mixture was quenched with H$_2$O and extracted with EtOAc. The organic phase was dried (anhydrous Na$_2$SO$_4$) and evaporated under reduced pressure. The residue was purified by flash chromatography (EtOAc/hexanes 1:4 to 6:1) to afford pure 91c (92 mg, 65% yield) as a colourless oil.

$^1$H NMR (CDCl$_3$, 300 MHz) δ: 7.68-7.66 (m, 4H), 7.46-7.35 (m, 6H), 7.15 (d, 1H, J=10.5 Hz), 6.85 (dd, 1H, J=15.3, 2.1 Hz), 6.64 (dd, 1H, J=10.5, 9.3 Hz), 6.39 (d, 1H, J=9.0 Hz), 6.30 (d, 1H, J=15.3 Hz), 5.88 (t, 1H, J=10.5 Hz), 5.71 (dd, 1H, J=10.5, 2.1 Hz), 5.69-5.61 (m, 1H), 5.53-5.47 (m, 1H), 5.35-5.30 (m, 1H), 4.88-4.80 (m, 1H), 4.31 (d, 1H, J=9.6 Hz), 4.28-4.19 (m, 1H), 3.87-3.82 (m, 1H), 3.65 (s, 3H), 3.14-3.06 (m, 1H), 2.58-2.47 (m, 1H), 2.41-2.32 (m, 1H), 2.23-2.04 (m, 4H), 1.43 (d, 3H, J=6.6 Hz), 1.18 (d, 3H, J=6.9 Hz), 1.05 (s, 9H), 0.98 (s, 9H).

$^{13}$C NMR (CDCl$_3$, 300 MHz) δ: 167.9, 164.5, 161.7, 145.5, 145.4, 136.1, 134.3, 132.4, 130.0, 129.9, 127.9, 127.8, 126.7, 126.1, 122.2, 121.6, 110.7, 109.4, 108.4, 93.2, 91.8, 81.0, 72.6, 61.0, 55.6, 39.6, 35.4, 34.0, 32.7, 29.8, 27.2, 26.8, 23.5, 19.5, 15.8, 13.2.

Synthesis of Compound 91d

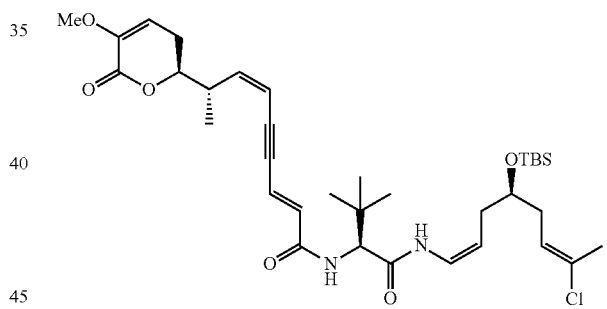

To a solution of 27 (26.2 mg, 0.085 mmol) in DIPEA (4 ml) at −20° C., Pd(Ph$_3$P)$_2$Cl$_2$ (6 mg, 0.0085 mmol) and CuI (5 mg, 0.025 mmol) were added. Then, 90b (45 mg, 0.094 mmol) was added and the reaction was stirred at 23° C. for 90 min. The crude mixture was quenched with H$_2$O and extracted with EtOAc. The organic phase was dried (anhydrous Na$_2$SO$_4$) and evaporated under reduced pressure. Purification by column chromatography (EtOAc/hexanes 1:10 to 2:1) to afforded 91d (44.5 mg, 79% yield) as a colourless oil.

$^1$H NMR (CDCl$_3$, 300 MHz) δ: 7.75 (d, 1H, J=11.1 Hz), 6.81 (dd, 1H, J=15.6, 2.4 Hz), 6.68 (t, 1H, J=9.3 Hz), 6.37 (d, 1H, J=9.3 Hz), 6.34 (d, 1H, J=11.7 Hz), 5.87 (t, 1H, J=10.8 Hz), 5.70 (dd, 1H, J=10.8, 2.4 Hz), 5.62-5.57 (m, 2H), 4.85 (q, 1H, J=8.1 Hz), 4.41 (d, 1H, J=9.3 Hz), 4.28-4.18 (m, 1H), 3.81-3.72 (m, 1H), 3.64 (s, 3H), 3.16-3.06 (m, 1H), 2.56-2.46 (m, 1H), 2.40-2.32 (m, 1H), 2.26-2.13 (m, 4H), 2.04 (s, 3H), 1.17 (d, 3H, J=6.6 Hz), 1.03 (s, 9H), 0.87 (s, 9H), 0.07 (s, 3H), 0.05 (s, 3H).

Synthesis of Compound 92a

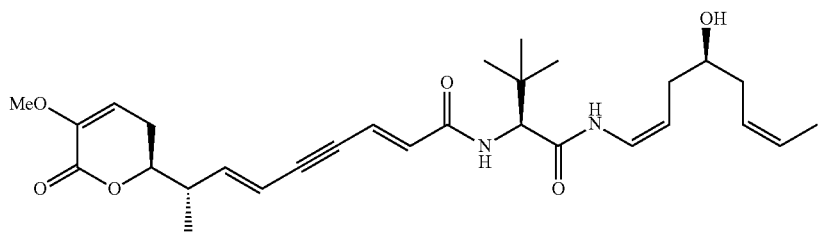 [SMILES: C/C=C\C[C@H](O)C/C=C\NC(=O)[C@@H](NC(=O)/C=C/C#C/C=C/[C@H](C)[C@@H]1CC=C(OC)C(=O)O1)C(C)(C)C]

To a solution of 91a (78.2 mg, 0.104 mmol) in anhydrous THF (2 mL) under $N_2$ and at 0° C., TBAF 1M in THF (0.2 mL, 0.208 mmol) was added. The reaction was stirred at room temperature for 3 hours and then quenched with a saturated aqueous solution of $NH_4Cl$ and extracted with EtOAc. The combined organic phases were dried over anhydrous $Na_2SO_4$, filtered and concentrated. The residue was purified by flash chromatography (hexane/EtOAc 4:1 to 1:2) to give alcohol 92a (17.9 mg, 34% yield) as a pale yellow oil.

$^1$H NMR (CDCl$_3$, 500 MHz) δ: 8.89 (d, 1H, J=10.0 Hz), 6.80 (dd, 1H, J=15.0, 2.0 Hz), 6.75 (dd, 1H, J=10.0, 9.0 Hz), 6.50 (d, 1H, J=9.5 Hz), 6.28 (d, 1H, J=15.5 Hz), 6.14 (dd, 1H, J=15.5, 8.0 Hz), 5.74 (dd, 1H, J=16.0, 2.5 Hz), 5.68-65 (m, 1H), 5.63 (dd, 1H, J=6.5, 2.5 Hz), 5.42-5.39 (m, 1H), 4.92-4.90 (m, 1H), 4.37 (d, 1H, J=9.0 Hz), 4.28-4.23 (m, 1H), 3.79-3.73 (m, 1H), 3.65 (s, 3H), 2.67-2.62 (m, 1H), 2.47-2.37 (m, 2H), 2.34-2.15 (m, 4H), 1.64 (d, 3H, J=7.0 Hz), 1.18 (d, 3H, J=6.5 Hz), 1.01 (s, 9H).

Synthesis of Compound 92b

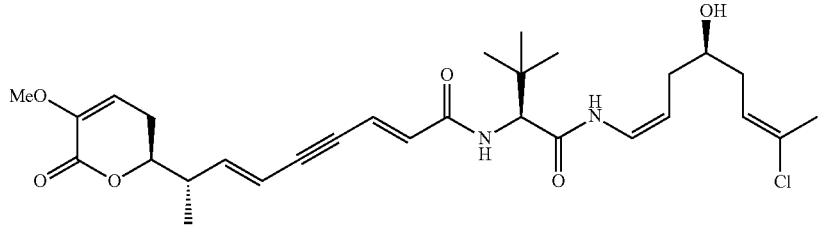 [SMILES: COC1=CC[C@@H]([C@@H](C)/C=C/C#C/C=C/C(=O)N[C@H](C(=O)N/C=C\C[C@@H](O)C/C=C(\C)Cl)C(C)(C)C)OC1=O]

To a solution of 91b (41.2 mg, 0.061 mmol) in anhydrous THF (1 mL) under $N_2$ and at 0° C., TBAF 1M in THF (0.12 mL, 0.122 mmol) was added. The reaction was stirred at room temperature for 18 hours and then quenched with a saturated aqueous solution of $NH_4Cl$ and extracted with EtOAc. The combined organic phases were dried over anhydrous $Na_2SO_4$, filtered and concentrated. The residue was purified by flash chromatography (hexane/EtOAc 4:1 to 1:2) to give alcohol 92b (14.7 mg, 65% yield) as a pale yellow oil.

$^1$H NMR (CDCl$_3$, 500 MHz) δ: 8.85 (d, 1H, J=10.2 Hz), 6.84-6.73 (m, 2H), 6.61 (d, 1H, J=9.3 Hz), 6.27 (d, 1H, J=15.6 Hz), 6.15 (dd, 1H, J=15.9, 8.4 Hz), 5.75 (d, 1H, J=15.9 Hz), 5.63-5.60 (m, 2H), 4.92-4.84 (m, 1H), 4.41 (d, 1H, J=9.3 Hz), 4.29-4.23 (m, 1H), 3.79-3.76 (m, 1H), 3.65 (s, 3H), 3.10 (bs, 1H), 2.69-2.61 (m, 1H), 2.46-2.37 (m, 2H), 2.20-2.14 (m, 4H), 2.04 (s, 3H), 1.18 (d, 3H, J=6.9 Hz), 1.02 (s, 9H).

Synthesis of Compound 92c

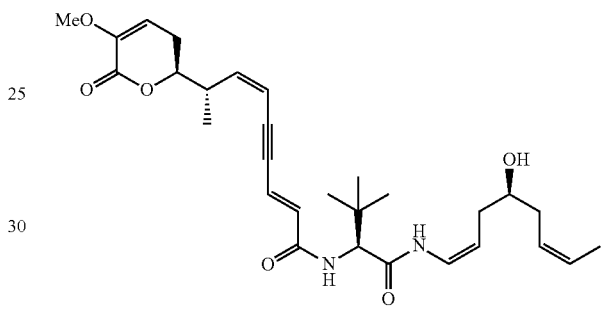

To a solution of 91c (71.5 mg, 0.095 mmol) in anhydrous THF (2 mL) under $N_2$ and at 0° C., TBAF 1M in THF (0.19 mL, 0.19 mmol) was added. The reaction was stirred at room temperature for 4 hours and then quenched with a saturated aqueous solution of $NH_4Cl$ and extracted with EtOAc. The combined organic phases were dried over anhydrous $Na_2SO_4$, filtered and concentrated. The residue was purified by flash chromatography (hexane/EtOAc 4:1 to 1:2) to give alcohol 92c (18.1 mg, 37% yield) as a pale yellow oil.

$^1$H NMR (CDCl$_3$, 300 MHz) δ: 8.94 (d, 1H, J=9.6 Hz), 6.83 (dd, 1H, J=15.3, 2.1 Hz), 6.75 (t, 1H J=9.6 Hz), 6.57 (d, 1H, J=9.6 Hz), 6.32 (d, 1H, J=15.3 Hz), 5.88 (d, 1H, J=10.2 Hz), 5.74-5.70 (m, 1H), 5.67-5.62 m, 2H), 5.44-5.36 (m, 1H), 4.95-4.86 (m, 1H), 4.38 (d, 1H, J=9.3 Hz), 4.28-4.23 (m, 1H), 3.77-3.73 (m, 1H), 3.65 (s, 3H), 3.14-3.06 (m, 1H), 2.59-2.11 (m, 6H), 1.63 (d, 3H, J=6.9 Hz), 1.19 (d, 3H, J=6.6 Hz), 1.02 (s, 9H).

Synthesis of Compound 92d

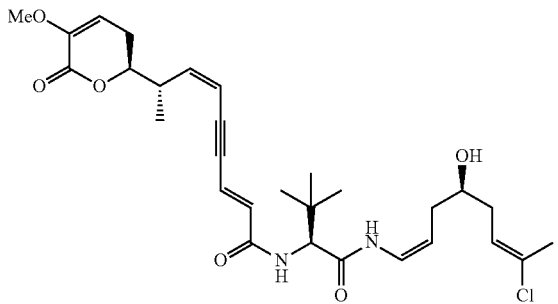 [SMILES: COC1=CC[C@@H]([C@@H](C)/C=C\C#C/C=C/C(=O)N[C@H](C(=O)N/C=C\C[C@@H](O)C/C=C(\C)Cl)C(C)(C)C)OC1=O]

To a solution of 91d (40 mg, 0.06 mmol) in anhydrous THF (0.6 mL) under N₂ and at room temperature, TBAF 1M in THF (0.12 mL, 0.12 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (hexane/EtOAc 4:1 to 1:2) to give alcohol 92d (20 mg, 61% yield) as a colourless oil.

$^1$H NMR (CDCl$_3$, 300 MHz) δ: 8.90 (d, 1H, J=9.9 Hz), 6.82 (dd, 1H, J=15.6, 2.4 Hz), 6.74 (t, 1H, J=9.6 Hz), 6.66 (d, 1H, J=9.3 Hz), 6.33 (d, 1H, J=9.3 Hz), 5.88 (t, 1H, J=10.5 Hz), 5.71 (dd, 1H, J=10.8, 2.4 Hz), 5.64-5.59 (m, 2H), 4.84 (q, 1H, J=7.8 Hz), 4.40 (d, 1H, J=9.3 Hz), 4.28-4.20 (m, 1H), 3.72 (m, 1H), 3.64 (s, 3H), 3.13-3.06 (m, 2H), 2.58-2.47 (m, 1H), 2.41-2.33 (m, 1H), 2.31-2.15 (m, 4H), 2.05 (s, 3H), 1.18 (d, 3H, J=6.9 Hz), 1.02 (s, 9H).

Example 20

Scheme 20 provides the synthesis of the following compound of the invention.

Scheme 20

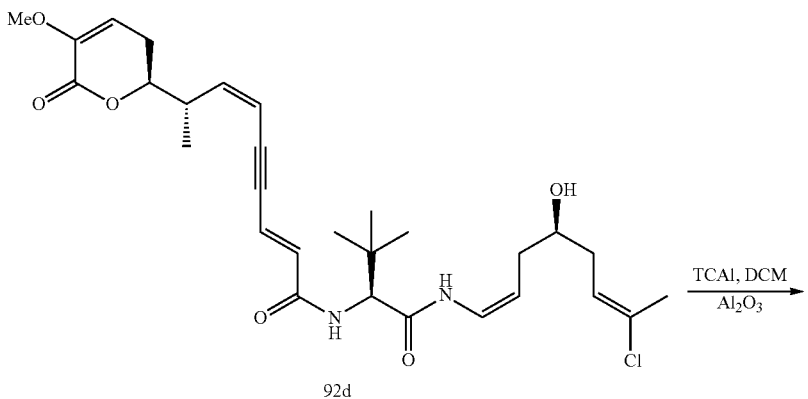

92d

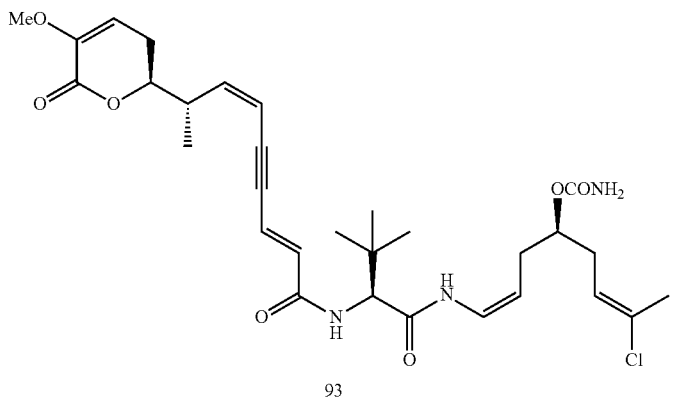

93

Synthesis of Compound 93

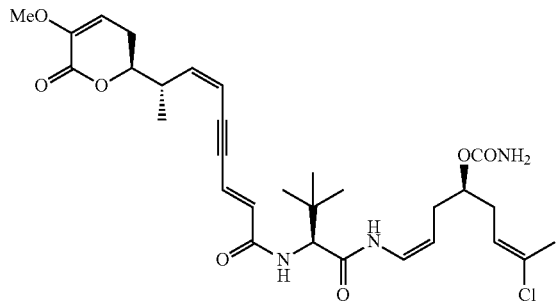

To a solution of 92d (6.5 mg, 0.012 mmol) in anhydrous DCM (0.2 mL) at 23° C., trichloroacetyl isocyanate (TCAI) (1.7 μl, 0.014 mmol) was added. The reaction was stirred at room temperature for 30 min and then neutral aluminium oxide was added (120 mg). The mixture was stirred for 30 min and then was soaked into a pad of aluminium oxide. The product was washed out using a mixture of dichloromethane/MeOH 50:1. The filtrate was evaporated under reduced pressure to give the crude product which was purified by column chromatography (dichloromethane/MeOH 100:1 to 40:1) affording compound 93 (3 mg, 42% yield) as a white solid.

$^1$H NMR (CDCl$_3$, 300 MHz) δ: 8.83 (d, 1H, J=10.5 Hz), 6.89-6.81 (m, 2H), 6.62 (d, 1H, J=9.9 Hz), 6.32 (d, 1H, J=15.3 Hz), 5.87 (t, 1H, J=9.0 Hz), 5.73 (dd, 1H, J=10.5, 2.4 Hz), 5.65-5.57 (m, 2H), 5.38 (bs, 2H), 4.84-4.76 (m, 1H), 4.48 (d, 1H, J=9.3 Hz), 4.40-4.33 (m, 1H), 4.28-4.21 (m, 1H), 3.66 (s, 3H), 3.19-3.10 (m, 1H), 2.58-2.42 (m, 3H), 2.35-2.30 (m, 2H), 2.14-2.06 (m, 1H), 2.08 (s, 3H), 1.20 (d, 3H, J=6.6 Hz), 1.03 (s, 9H).

$^{13}$C NMR (CDCl$_3$, 125 MHz) δ: 167.9, 164.3, 161.4, 157.6, 145:1, 145.0 132.3, 132.0, 124.5, 122.3, 121.9, 110.6, 108.3, 104.9, 92.9, 91.7, 80.8, 75.1, 61.2, 55.5, 39.3, 35.0, 32.9, 30.9, 26.7, 26.4, 21.0, 15.9.

MS (ES) [m/z]=590.2 [M+H]$^+$.

Example 21

Scheme 21 provides the synthesis of several compounds of the invention.

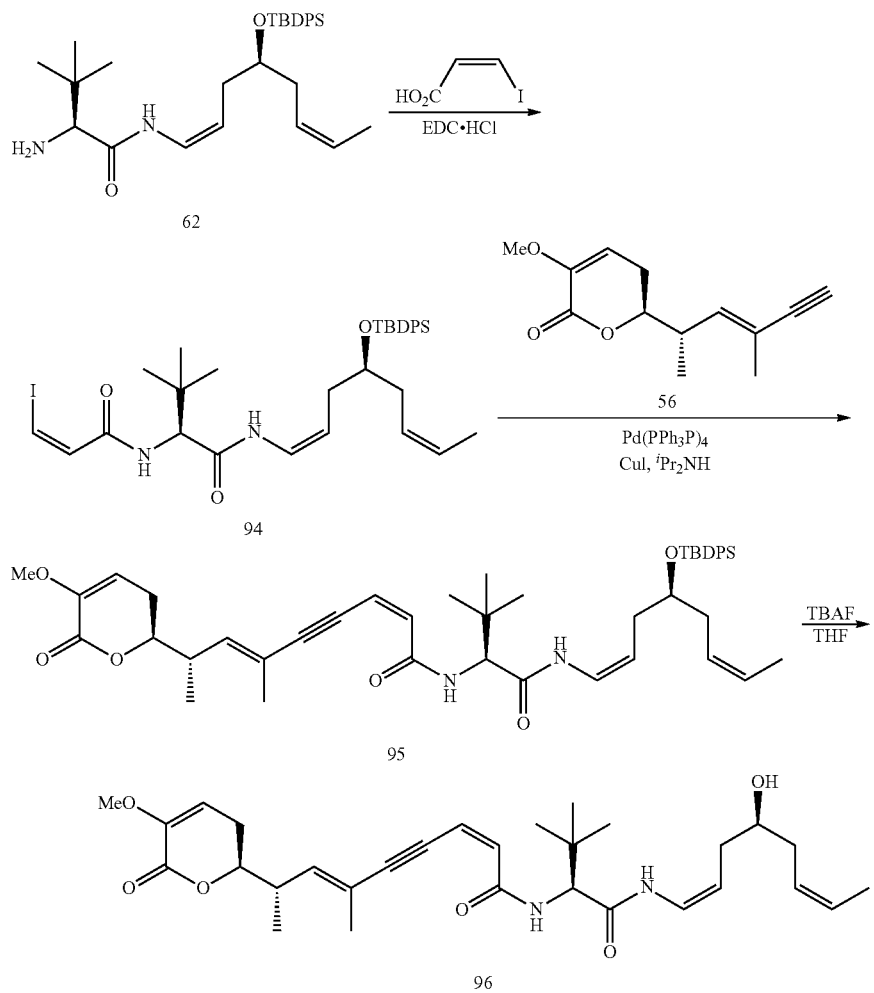

Synthesis of Intermediate 94

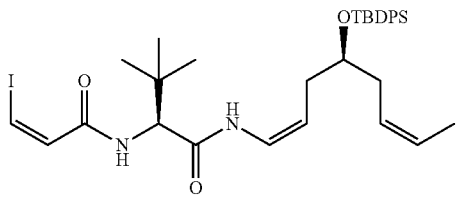

A solution of (Z)-Iodoacrylic acid (365 mg, 1.84 mmol) (prepared as described in Takeuchi, R. Tanabe, K., Tanaka, S. *J. Org. Chem.* 2000, 65, 1558-1561), amine 62 (700 mg, 1.42 mmol) in anhydrous DCM (12 mL) was cooled to 0° C. under argon and N-(3-Dimethylaminopropyl)-N'-ethylcarbodiimide hydrochloride, EDC (340.8 mg, 1.78 mmol) was added. The reaction mixture was stirred at 0° C. for 10 min and then at 23° C. for 3 hours, was quenched with a saturated aqueous solution of NaCl and extracted with dichloromethane. The combined organic layers were dried (anhydrous $Na_2SO_4$), filtered and concentrated. The residue was purified by flash chromatography (EtOAc/hexane 1:10 to 1:1) to afford 94 (675 mg, 71% yield) as a colourless foam solid.

$^1$H NMR (CDCl$_3$, 300 MHz) δ: 7.69-7.66 (m, 4H), 7.44-7.36 (m, 6H), 7.24 (d, 1H, J=9.6 Hz), 7.06 (d, 1H, J=9.3 Hz), 6.90 (d, 1H J=9.0 Hz), 6.68-6.61 (m, 2H), 5.55-5.43 (m, 1H), 5.35-5.26 (m, 1H), 4.89-4.81 (m, 1H), 4.38 (d, 1H, J=9.3 Hz), 3.88-3.80 (m, 1H), 2.23-2.06 (m, 4H), 1.43 (d, 3H, J=6.9 Hz), 1.05 (s, 9H), 1.01 (s, 9H).

$^{13}$C NMR (CDCl$_3$, 125 MHz) δ: 167.4, 164.3, 135.8, 134.1, 133.0, 129.7, 129.6, 127.6, 127.5, 126.4, 125.8, 121.4, 109.1, 88.3, 72.3, 60.4, 35.1, 33.8, 32.5, 27.0, 26.7, 19.3, 12.9.

MS (ES) [m/z]=695.2 [M+Na]$^+$.

Synthesis of Compound 95

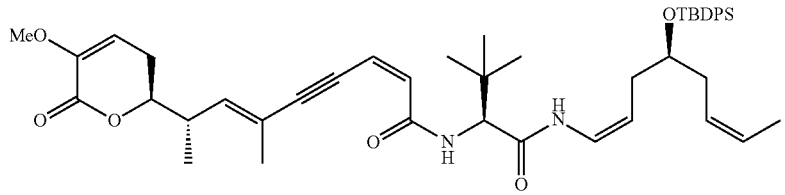

To a solution of 94 (304.4 mg, 0.45 mmol) in DIPA (5.5 ml) at 23° C., Pd(Ph$_3$P)$_4$ (39.3 mg, 0.034 mmol) and CuI (12.9 mg, 0.068 mmol) were added. Then, 56 (100 mg, 0.45 mmol) was added and the reaction was stirred at 23° C. for 45 min. The crude mixture was quenched with $H_2O$ and extracted with EtOAc. The organic phase was dried (anhydrous $Na_2SO_4$) and evaporated under reduced pressure. The residue was purified by flash chromatography (EtOAc/hexane 1:4 to 3:1) to afford pure 95 (300 mg, 87° A) yield) as a colourless foam solid.

$^1$H NMR (CDCl$_3$, 300 MHz) δ: 7.82 (d, 1H, J=9.3 Hz), 7.68-7.65 (m, 4H), 7.46-7.29 (m, 7H), 6.62 (dd, 1H, J=10.2, 9.3 Hz), 6.14 (d, 1H, J=12.3 Hz), 6.08 (dd, 1H, J=10.5, 9.3 Hz), 6.05 (d, 1H, J=12.3 Hz), 5.60 (dd, 1H, J=6.3, 3.0 Hz), 5.52-5.43 (m, 1H), 5.33-5.25 (m, 1H), 4.85-4.77 (m, 1H), 4.44 (d, 1H, J=9.3 Hz), 4.24-4.23 (m, 1H), 3.88-3.80 (m, 1H), 3.64 (s, 3H), 2.91-2.79 (m, 1H), 2.54-2.34 (m, 2H), 2.23-2.04 (m, 4H), 1.92 (s, 3H), 1.42 (d, 3H, J=6.9 Hz), 1.13 (d, 3H, J=6.6 Hz), 1.04 (s, 9H), 0.99 (s, 9H).

$^{13}$C NMR (CDCl$_3$, 125 MHz) δ: 167.9, 164.6, 161.7, 145.5, 136.1, 134.3, 132.5, 129.9, 127.8, 126.7, 126.1, 121.7, 118.9, 116.4, 108.9, 108.4, 104.5, 98.8, 82.8, 81.6, 72.6, 60.9, 55.7, 38.0, 35.5, 34.0, 32.7, 27.2, 26.9, 26.5, 19.5, 17.3, 16.5, 13.1.

Synthesis of Compound 96

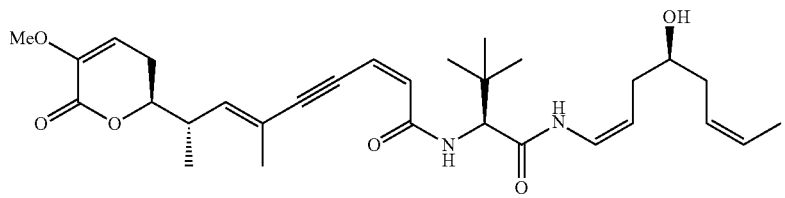 [SMILES: C/C=C\C[C@H](O)C/C=C\NC(=O)[C@@H](NC(=O)/C=C\C#C/C(C)=C/[C@H](C)[C@@H]1CC=C(OC)C(=O)O1)C(C)(C)C]

To a solution of 95 (250 mg, 0.326 mmol) in THF (3.3 mL) under N$_2$ and at 0° C., TBAF 1M in THF (0.65 mL, 0.65 mmol) was added. The reaction was stirred at room temperature for 3 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (hexane/EtOAc 4:1 to 1:3) to give alcohol 96 (150 mg, 87% yield) as a colourless oil.

$^1$H NMR (CDCl$_3$, 300 MHz) δ: 8.76 (d, 1H, J=9.9 Hz), 7.83 (d, 1H, J=9.0 Hz), 6.74 (t, 1H, J=9.3 Hz), 6.17 (d, 1H, J=12.0 Hz), 6.15-6.09 (m, 1H), 6.07 (d, 1H, J=12.0 Hz), 5.74-5.60 (m, 1H), 5.61 (dd, 1H, J=6.3, 3.0 Hz), 5.44-5.37 (m, 1H), 4.94-4.85 (m, 1H), 4.41 (d, 1H, J=9.3 Hz), 4.25-4.17 (m, 1H), 3.76 (m, 1H), 3.65 (s, 3H), 2.92-2.80 (m, 1H), 2.55-2.11 (m, 6H), 1.93 (s, 3H), 1.62 (d, 3H, J=6.6 Hz), 1.14 (d, 3H, J=6.6 Hz), 1.01 (s, 9H).

Example 22
Scheme 22 provides the synthesis of several compounds of the invention.
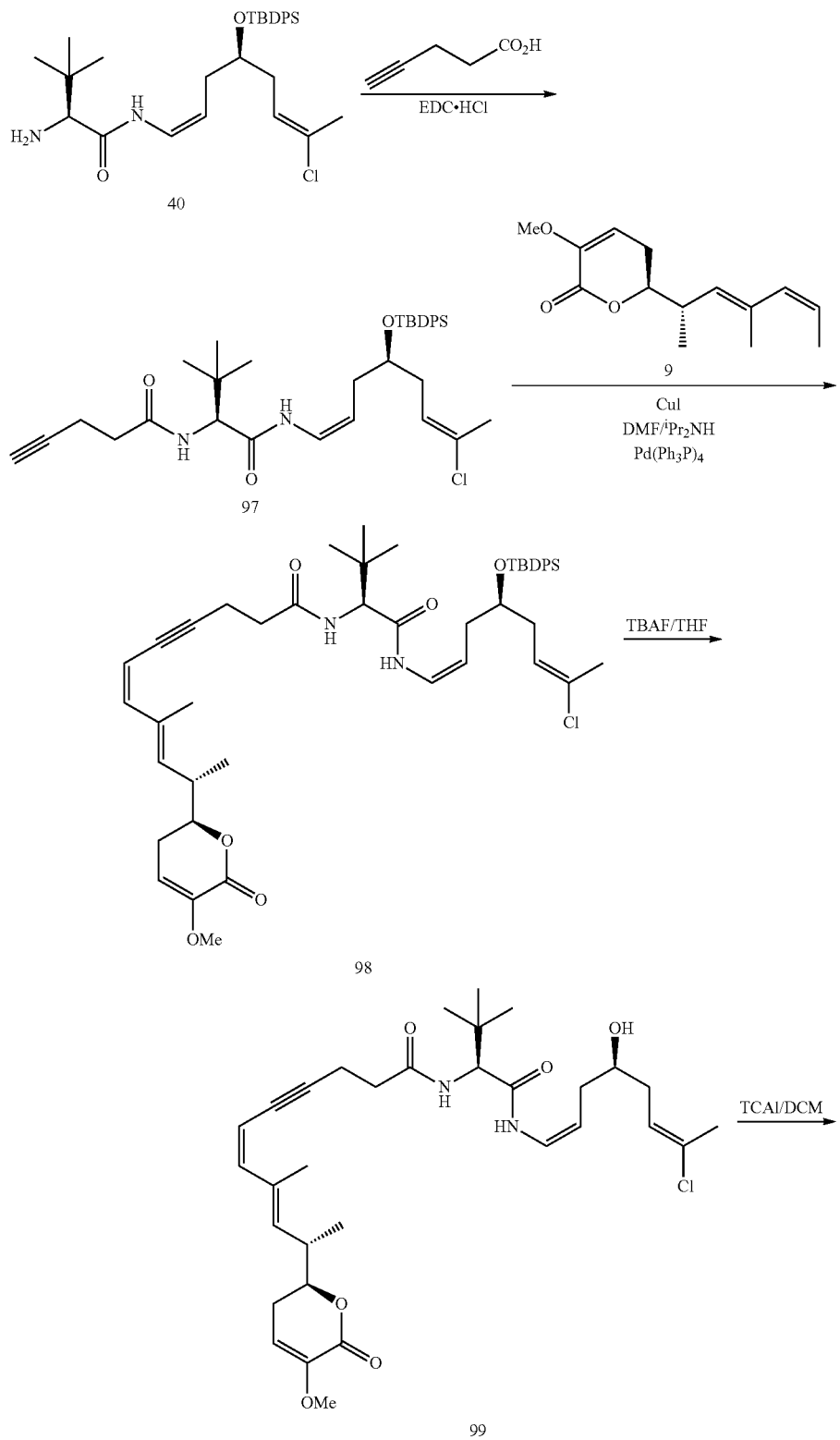

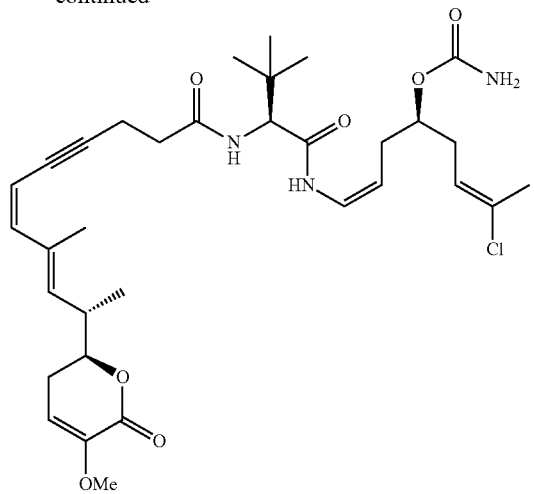

100

Synthesis of Intermediate 97

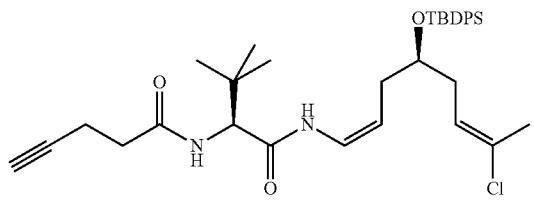

To a solution of 40 (200 mg, 0.38 mmol) and 4-pentynoic acid (48 mg, 0.49 mmol) in anhydrous DCM (3.8 ml) at 0° C., EDC (91 mg, 0.47 mmol) was added. The reaction was stirred at 0° C. for 30 min and 2 hours at room temperature. Then, the crude mixture was hydrolized with water and extracted with dichloromethane (3×5 mL). After drying and evaporating the solvent under reduced pressure the crude was purified by column chromatography (hexane/EtOAc, 6:1) to afford pure compound 97 (105 mg, 47% yield) as a colourless oil.

$^1$H NMR (CDCl$_3$, 300 MHz) δ: 7.66 (m, 4H), 7.43 (m, 6H), 7.14 (d, 1H, J=10.6 Hz), 6.65 (t, 1H, J=9.3 Hz), 6.40 (d, 1H, J=9.1 Hz), 5.52 (t, 1H, J=7.2 Hz), 4.75 (q, 1H, J=7.6 Hz), 4.29 (d, 1H, J=9.2 Hz), 3.81 (m, 1H), 2.63-2.40 (m, 4H), 2.19-2.03 (m, 5H), 1.86 (s, 3H), 1.05 (s, 9H), 0.98 (s, 9H).

Synthesis of Compound 98

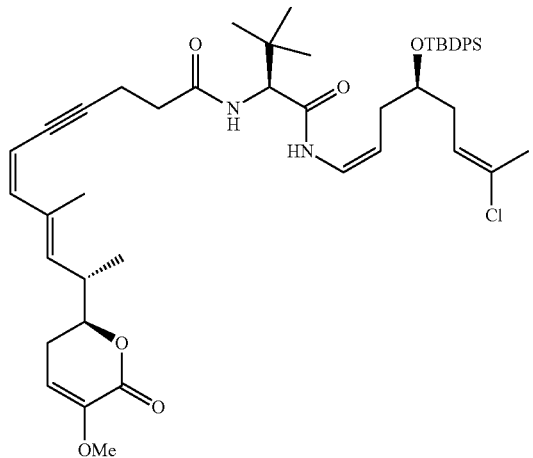

To a solution of iodo compound 9 (52 mg, 0.148 mmol) in diisopropylamine (0.75 mL) under N$_2$ at room temperature, Pd(Ph$_3$P)$_4$ (2.3 mg, 0.002 mmol) and CuI (1.0 mg, 0.005 mmol) were added. Then, compound 97 (90 mg, 0.148 mmol) was added portionwise and the reaction mixture was stirred at room temperature for 2 hours. The crude was quenched with H$_2$O and extracted with EtOAc. The organic phase was dried (anhydrous Na$_2$SO$_4$) and evaporated under reduced pressure. Purification by column chromatography (hexane/EtOAc 3:1 to 1:2) afford pure compound 98 (105 mg, 86% yield) as a white solid.

$^1$H NMR (CDCl$_3$, 300 MHz) δ: 7.66 (m, 4H), 7.41 (m, 6H), 7.26 (d, 1H, J=10.6 Hz), 6.64 (t, 1H, J=10.1 Hz), 6.42 (d, 1H J=9.3 Hz), 6.06 (d, 1H, J=12.0 Hz), 5.61 (m, 1H), 5.48 (m, 2H), 5.35 (d, 1H, J=11.8 Hz), 4.74 (q, 1H, J=8.3 Hz), 4.28 (d, 1H, J=9.2 Hz), 4.16 (m, 1H), 3.81 (m, 1H), 3.64 (s, 3H), 2.81 (m, 1H), 2.66 (m, 2H), 2.47-2.36 (m, 4H), 2.18-2.06 (m, 4H), 2.04 (s, 3H), 1.85 (s, 3H), 1.12 (d, 3H, J=6.6 Hz), 1.04 (s, 9H), 0.98 (s, 9H).

Synthesis of Compound 99

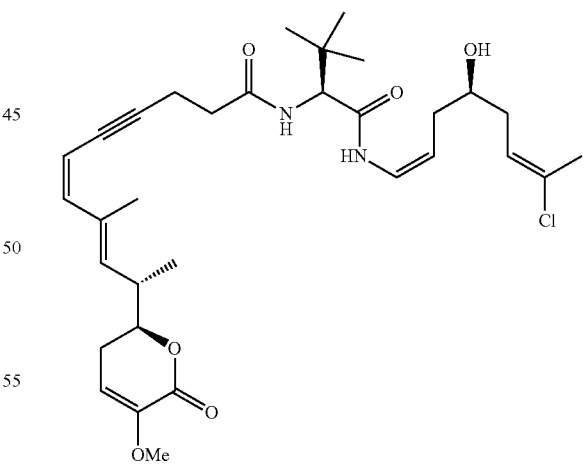

To a solution of 98 (75 mg, 0.09 mmol) in anhydrous THF (1.5 mL) under N$_2$ and at room temperature, TBAF 1M in THF (0.18 mL, 0.18 mmol) was added. The reaction was stirred at room temperature for 4 hours and then quenched with a saturated aqueous solution of NH$_4$Cl and extracted with EtOAc. The combined organic phases were dried over anhydrous Na$_2$SO$_4$, filtered and concentrated. The residue was purified by flash chromatography (hexane/EtOAc 3:1 to 1:3) to give alcohol 99 (35 mg, 67% yield) as a white solid.

$^1$H NMR (CDCl$_3$, 300 MHz) δ: 8.92 (d, 1H, J=10.1 Hz), 6.74 (t, 1H, J=9.5 Hz), 6.67 (d, 1H, J=9.1 Hz), 6.06 (d, 1H, J=12.0 Hz), 5.62 (m, 2H), 5.47 (d, 1H, J=9.8 Hz), 5.34 (d, 1H, J=11.9 Hz), 4.84 (q, 1H, J=8.5 Hz), 4.32 (d, 1H, J=9.1 Hz), 4.18 (m, 1H), 3.73 (m, 1H), 3.64 (s, 3H), 3.20 (d, 1H, J=4.0 Hz), 2.82 (m, 1H), 2.66 (m, 2H), 2.49-2.36 (m, 4H), 2.24-2.14 (m, 4H), 2.05 (s, 3H), 2.02 (s, 3H), 1.12 (d, 3H, J=6.6 Hz), 1.00 (s, 9H).

$^{13}$C NMR (CDCl$_3$, 75 MHz) δ: 171.3, 168.4, 161.7, 145.1, 142.1, 135.5, 134.4, 131.7, 123.6, 123.4, 108.4, 108.2, 106.1, 94.3, 81.8, 80.2, 71.4, 60.9, 36.7, 36.1, 35.3, 34.5, 33.0, 29.6, 26.5, 26.3, 21.0, 16.4, 16.1, 15.5.

Synthesis of Compound 100

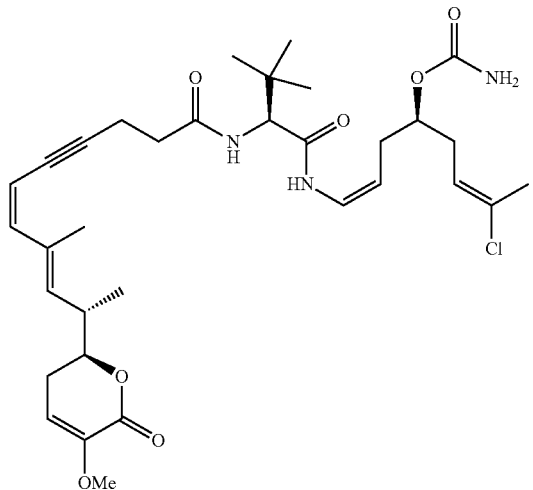 [SMILES: COC1=CC[C@@H]([C@@H](C)/C=C(C)/C=C\C#CCCC(=O)N[C@H](C(=O)N/C=C\C[C@H](C/C=C(\C)Cl)OC(N)=O)C(C)(C)C)OC1=O]

To a solution of 99 (30 mg, 0.05 mmol) in anhydrous DCM (3.15 mL) at room temperature, trichloroacetyl isocyanate (TCAI) (6 µl, 0.06 mmol) was added. The reaction was stirred at room temperature for 30 min and then neutral aluminium oxide was added (375 mg). The mixture was stirred for 1 h and then was soaked into a pad of aluminium oxide. The product was washed out using a mixture of dichloromethane/MeOH 50:1. The filtrate was evaporated under reduced pressure to give the crude product which was purified by column chromatography (hexane/EtOAc) affording compound 100 (26 mg, 82% yield) as a white solid.

$^1$H NMR (CDCl$_3$, 300 MHz) δ: 8.87 (d, 1H, J=10.7 Hz), 6.81 (t, 1H, J=9.8 Hz), 6.62 (d, 1H, J=9.5 Hz), 6.06 (d, 1H, J=12.0 Hz), 5.75 (bs, 2H), 5.61 (m, 2H), 5.45 (d, 1H, J=10.1 Hz), 5.35 (d, 1H, J=11.9 Hz), 4.80 (q, 1H, J=8.4 Hz), 4.37 (m, 1H), 4.33 (d, 1H, J=9.3 Hz), 4.18 (m, 1H), 3.64 (s, 3H), 2.83 (m, 1H), 2.66 (m, 2H), 2.50-2.27 (m, 8H), 2.05 (s, 3H), 2.03 (s, 3H), 1.12 (d, 3H, J=6.6 Hz), 0.99 (s, 9H).

Example 23

Scheme 23 provides the synthesis of several compounds of the invention.

Scheme 23

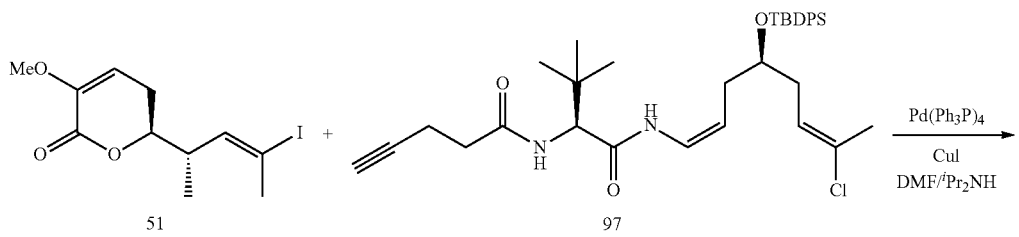

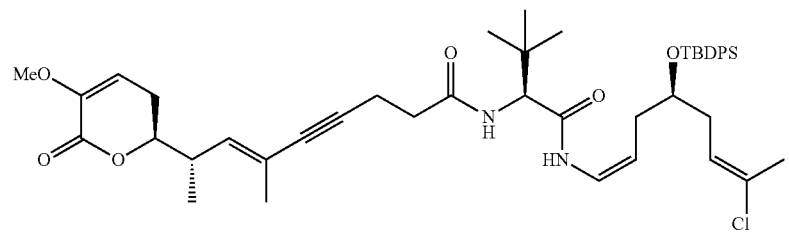

Synthesis of Compound 101

To a solution, of iodo compound 51 (70 mg, 0.217 mmol) in diisopropylamine (1.1 mL) under $N_2$ at room temperature, $Pd(Ph_3P)_4$ (5 mg, 0.004 mmol) and CuI (1.7 mg, 0.008 mmol) were added. Then, compound 97 (132 mg, 0.217 mmol) was added portionwise and the reaction mixture was stirred at room temperature for 2 hours. The crude was quenched with $H_2O$ and extracted with EtOAc. The organic phase was dried (anhydrous $Na_2SO_4$) and evaporated under reduced pressure. Purification by column chromatography (hexane/EtOAc 3:1 to 1:2) afforded pure compound 101 (80 mg, 50% yield) as a white solid.

$^1$H NMR (CDCl$_3$, 300 MHz) δ: 7.66 (m, 4H), 7.41 (m, 6H), 7.25 (d, 1H, J=10.6 Hz), 6.65 (t, 1H, J=10.1 Hz), 6.44 (d, 1H J=9.3 Hz), 5.63-5.48 (m, 3H), 4.78 (q, 1H, J=8.3 Hz), 4.32 (d, 1H, J=9.2 Hz), 4.14 (m, 1H), 3.81 (m, 1H), 3.64 (s, 3H), 2.81 (m, 1H), 2.62 (m, 2H), 2.46-2.33 (m, 4H), 2.18-2.05 (m, 4H), 2.02 (s, 3H), 1.85 (s, 3H), 1.12 (d, 3H, J=6.6 Hz), 1.04 (s, 9H), 0.98 (s, 9H).

Example 24

Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |

Evaluation of Cytotoxic Activity Using the SBR Colorimetric Assay

A colorimetric type of assay, using sulforhodamine B (SRB) reaction has been adapted for a quantitative measurement of cell growth and viability (following the technique described by Skehan P et al. J. Natl. Cancer Inst. 1990, 82, 1107-1112).

This form of assay employs SBS-standard 96-well cell culture microplates (Faircloth et al. Methods in cell science, 1988, 11(4), 201-205; Mosmann et al, Journal of Immunological. Methods, 1983, 65(1-2), 55-63). All the cell lines used in this study, derived from different types of human cancer, were obtained from the American Type Culture Collection (ATCC).

Cells were maintained in Dulbecco's Modified Eagle Medium (DMEM) supplemented with 10% Fetal Bovine Serum (FBS), 2 mM L-glutamine, 100 U/mL penicillin and 100 U/mL streptomycin at 37° C., 5% $CO_2$ and 98% humidity. For the experiments, cells were harvested from subconfluent cultures using trypsinization and resuspended in fresh medium before counting and plating.

Cells were seeded in 96 well microtiter plates at $5 \times 10^3$ cells per well in aliquots of 150 µL, and allowed to attach to the plate surface for 18 hours in drug free medium. One control (untreated) plate of each cell line was fixed (as described below) and used for time zero reference value. Afterwards, test samples were added to the cultures in ten serial dilutions, in aliquots of 50 µL, ranging from 10 to 0.00262 µg/mL. After 48 hours exposure, the antitumor effect was estimated by the SRB method: Briefly, cells were washed twice with PBS, fixed for 15 min in 1% glutaraldehyde solution, rinsed twice in PBS, and stained in 0.4% SRB solution for 30 min at room temperature. Cells were then rinsed several times with 1% acetic acid solution and air-dried. SRB was then extracted in 10 mM trizma base solution and the absorbance measured in an automated spectrophotometric plate reader at 490 nm. Cell survival was expressed as percentage of control cell growth. The final effect of the sample being tested was estimated by applying the NCI algorithm (Boyd M R and Paull K D. Drug Dev. Res. 1995, 34, 91-104).

Using the mean±SD of triplicate cultures, a dose-response curve was automatically generated using nonlinear regression analysis. Three reference parameters were calculated (NCI algorithm) by automatic interpolation: $GI_{50}$=concentration that produces 50% growth inhibition; TGI=total growth inhibition (cytostatic effect) and $LC_{50}$=concentration that produces 50% net cell killing (cytotoxic effect).

Table 1 illustrates data on the biological activity of compounds of the present invention.

TABLE 1

| | | Cytotoxicity assay - Activity Data (Molar) | | | |
|---|---|---|---|---|---|
| | | Compound 64a | Compound 65a | Compound 66a | Compound 64b |
| MDA-MB-231 | $GI_{50}$ | 4.89E-06 | 3.56E-06 | 4.47E-08 | 1.33E-06 |
| | TGI | >1.48E-05 | 9.98E-06 | 7.78E-06 | >1.51E-05 |
| | $LC_{50}$ | >1.48E-05 | >1.78E-05 | >1.66E-05 | >1.51E-05 |
| A549 | $GI_{50}$ | 4.44E-06 | 3.39E-06 | 3.31E-08 | 6.80E-07 |
| | TGI | >1.48E-05 | 6.24E-06 | 3.97E-07 | 3.33E-06 |
| | $LC_{50}$ | >1.48E-05 | 1.18E-05 | >1.66E-05 | >1.51E-05 |
| HT29 | $GI_{50}$ | 2.22E-06 | 1.78E-06 | 1.21E-08 | 4.23E-07 |
| | TGI | 4.29E-06 | 3.03E-06 | 5.13E-08 | 6.50E-07 |
| | $LC_{50}$ | >1.48E-05 | 7.31E-06 | 2.81E-06 | 2.42E-06 |
| | | Compound 65b | Compound 66b | Compound 67 | Compound 68 |
| MDA-MB-231 | $GI_{50}$ | 5.48E-07 | 2.71E-08 | 9.10E-07 | 7.84E-07 |
| | TGI | >1.83E-05 | 3.73E-07 | 1.04E-06 | 1.49E-06 |
| | $LC_{50}$ | >1.83E-05 | 4.58E-06 | 1.21E-06 | 6.50E-06 |
| A549 | $GI_{50}$ | 3.11E-07 | 2.54E-08 | 1.57E-06 | 1.47E-06 |
| | TGI | 1.81E-06 | 8.13E-08 | 2.82E-06 | 4.21E-06 |
| | $LC_{50}$ | >1.83E-05 | >1.69E-05 | 4.86E-06 | >1.91E-05 |

TABLE 1-continued

| | | Cytotoxicity assay - Activity Data (Molar) | | | |
|---|---|---|---|---|---|
| HT29 | $GI_{50}$ | 1.83E−07 | 2.20E−08 | 1.88E−06 | 4.59E−07 |
| | TGI | 4.94E−07 | 2.88E−08 | 2.35E−06 | 7.07E−07 |
| | $LC_{50}$ | >1.83E−05 | 4.24E−08 | 3.14E−06 | >1.91E−05 |

| | | Compound 69 | Compound 70 | Compound 71 | Compound 72 |
|---|---|---|---|---|---|
| MDA-MB-231 | GI50 | 3.36E−07 | 1.70E−06 | 2.09E−07 | 2.46E−10 |
| | TGI | 1.63E−06 | 2.48E−06 | 2.85E−06 | 1.93E−09 |
| | LC50 | 8.13E−06 | 3.53E−06 | >1.90E−05 | >1.76E−07 |
| A549 | GI50 | 2.30E−07 | 2.09E−06 | 2.66E−07 | 1.76E−10 |
| | TGI | >1.77E−05 | 2.61E−06 | 1.84E−06 | 2.81E−09 |
| | LC50 | >1.77E−05 | 3.27E−06 | 8.54E−06 | >1.76E−07 |
| HT29 | GI50 | 1.73E−07 | 1.96E−06 | 5.89E−08 | 5.79E−11 |
| | TGI | 4.24E−07 | 2.74E−06 | 1.75E−06 | 1.25E−10 |
| | LC50 | >1.77E−05 | 4.05E−06 | >1.90E−05 | >1.76E−07 |

| | | Compound 78 | Compound 79 | Compound 80 | Compound 81 | Compound 85 |
|---|---|---|---|---|---|---|
| MDA-MB-231 | $GI_{50}$ | >1.25E−5 | >1.31E−5 | 1.52E−7 | 2.98E−6 | 1.02E−9 |
| | TGI | >1.25E−5 | >1.31E−5 | >1.90E−5 | >1.76E−5 | 1.81E−9 |
| | $LC_{50}$ | >1.25E−5 | >1.31E−5 | >1.90E−5 | >1.76E−5 | >1.64E−8 |
| A549 | $GI_{50}$ | >1.25E−5 | >1.31E−5 | 9.30E−8 | 2.28E−6 | 7.23E−10 |
| | TGI | >1.25E−5 | >1.31E−5 | 3.04E−7 | 8.43E−6 | 1.64E−9 |
| | $LC_{50}$ | >1.25E−5 | >1.31E−5 | >1.90E−5 | >1.76E−5 | >1.64E−8 |
| HT29 | $GI_{50}$ | >1.25E−5 | 5.10E−6 | 4.94E−6 | 1.26E−6 | 3.45E−10 |
| | TGI | >1.25E−5 | >1.31E−5 | 9.49E−8 | 2.98E−6 | 6.25E−10 |
| | $LC_{50}$ | >1.25E−5 | >1.31E−5 | >1.90E−5 | >1.76E−5 | 1.97E−9 |

| | | Compound 89 | Compound 96 | Compound 98 | Compound 99 |
|---|---|---|---|---|---|
| MDA-MB-231 | GI50 | 2.96E−10 | 1.31E−5 | 1.04E−7 | 2.72E−6 |
| | TGI | >1.74E−9 | >1.90E−5 | 1.81E−7 | 6.11E−6 |
| | LC50 | >1.74E−9 | >1.90E−5 | >1.21E−5 | 1.32E−5 |
| A549 | GI50 | 1.38E−10 | 7.78E−6 | 1.11E−7 | 3.06E−6 |
| | TGI | 2.79E−10 | >1.90E−5 | 4.95E−7 | 6.62E−6 |
| | LC50 | 8.19E−10 | >1.90E−5 | >1.21E−5 | 1.22E−5 |
| HT29 | GI50 | 8.02E−11 | 5.89E−6 | 5.32E−8 | 9.00E−7 |
| | TGI | 1.27E−10 | 8.92E−6 | 7.01E−8 | 2.21E−6 |
| | LC50 | 2.27E−10 | >1.90E−5 | 1.69E−7 | 5.77E−6 |

| | | Compound 100 |
|---|---|---|
| MDA-MB-231 | $GI_{50}$ | 3.48E−7 |
| | TGI | >1.58E−5 |
| | $LC_{50}$ | >1.58E−5 |
| A549 | $GI_{50}$ | 3.95E−7 |
| | TGI | 2.21E−6 |
| | $LC_{50}$ | >1.58E−5 |
| HT29 | $GI_{50}$ | 5.38E−8 |
| | TGI | 3.01E−7 |
| | $LC_{50}$ | 7.59E−6 |

The invention claimed is:

1. A compound of general formula I

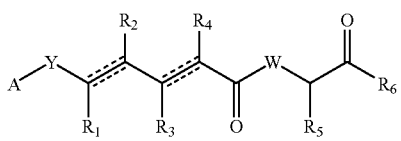

(I)

wherein Y is selected from $-CR_{ay}=CR_{by}-$, $-C\equiv C-$, $-CHR_{ay}-CHR_{by}-CHR_{cy}-$, $-CHR_{ay}-CR_{by}=CR_{cy}-$, and $-CHR_{ay}-C\equiv C-$;
each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
each $R_1$, $R_2$, $R_3$, $R_4$, and $R_5$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R_6$ is selected from $NR_8R_9$, and $OR_{10}$;
A is

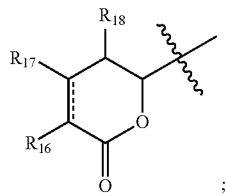

;

W is $NR_7$;
$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

R$_8$ is selected from hydrogen, COR$_a$, COOR$_a$, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl;

R$_{10}$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;

each dotted line represents an optional additional bond, but when a triple bond exists between the C atoms to which R$_1$ and R$_2$ are attached, R$_1$ and R$_2$ are absent, and when a triple bond exists between the C atoms to which R$_3$ and R$_4$ are attached, R$_3$ and R$_4$ are absent;

R$_9$ is selected from hydrogen, COR$_a$, COOR$_a$, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl, with the proviso that when Y is —CHR$_{ay}$—CHR$_{by}$—CHR$_{cy}$— or —CHR$_{ay}$—CR$_{by}$=CR$_{cy}$— and a single or a double bond exists between the C atoms to which R$_3$ and R$_4$ are attached then R$_9$ is substituted or unsubstituted C$_4$-C$_{12}$ alkenynyl;

R$_{16}$, R$_{17}$ and R$_{18}$ are independently selected from hydrogen, OR$_a$, OCOR$_a$, OCOOR$_a$, NR$_a$R$_b$, NR$_a$COR$_b$, and NR$_a$C(=NR$_a$)NR$_a$R$_b$, substituted or unsubstituted C$_1$-C$_{12}$ alkyl, substituted or unsubstituted C$_2$-C$_{12}$ alkenyl and substituted or unsubstituted C$_2$-C$_{12}$ alkynyl;

each R$_a$ and R$_b$ are independently selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl and substituted or unsubstituted heterocyclic group; or a pharmaceutically acceptable salt, tautomer or stereoisomer thereof.

2. A compound according to claim 1, wherein R$_{16}$ is selected from hydrogen, OR$_a$ and OCOR$_a$, wherein R$_a$ is selected from hydrogen and substituted or unsubstituted C$_1$-C$_6$ alkyl.

3. A compound according to claim 2, wherein R$_{16}$ is selected from hydrogen, OH and methoxy.

4. A compound according to claim 1, wherein one additional bond is present between the C atoms to which R$_{16}$ and R$_{17}$ are attached.

5. A compound according to claim 1, wherein R$_{17}$ and R$_{18}$ are hydrogen.

6. A compound according to claim 1, wherein R$_1$, R$_2$, R$_3$ and R$_4$ are independently selected from hydrogen and a substituted or unsubstituted C$_1$-C$_6$ alkyl.

7. A compound according to claim 6, wherein R$_1$, R$_2$, R$_3$ and R$_4$ are hydrogen.

8. A compound according to claim 1, wherein Y is selected from —CR$_{ay}$=CR$_{by}$— and —CHR$_{ay}$—CR$_{by}$=CR$_{cy}$—, and wherein R$_{ay}$, R$_{by}$ and R$_{cy}$ are independently selected from hydrogen and substituted or unsubstituted C$_1$-C$_6$ alkyl.

9. A compound according to claim 8, wherein R$_{ay}$, R$_{by}$ and R$_{cy}$ are independently selected from hydrogen and methyl.

10. A compound according to claim 1, wherein R$_5$ is selected from hydrogen and a substituted or unsubstituted C$_1$-C$_6$ alkyl.

11. A compound according to claim 10, wherein R$_5$ is selected from methyl, isopropyl and tert-butyl.

12. A compound according to claim 1, wherein R$_7$ is hydrogen.

13. A compound according to claim 1, wherein R$_6$ is NR$_8$R$_9$ and wherein R$_8$ is hydrogen and R$_9$ is selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl.

14. A compound according to claim 13, wherein R$_9$ is selected from a substituted C$_2$-C$_{12}$ alkenyl and a substituted C$_4$-C$_{12}$ alkenynyl that are substituted in one or more positions with halogen, OR', =O, OCOR', OCONHR', OCONR'R', CONHR', CONR'R' and protected OH, wherein each of the R' groups is independently selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl and substituted or unsubstituted aryl.

15. A compound according to claim 1, wherein one additional bond is present between the C atoms to which R$_1$ and R$_2$ are attached and one or two additional bonds are present between the C atoms to which R$_3$ and R$_4$ are attached.

16. A compound according to claim 1, having the following formula:

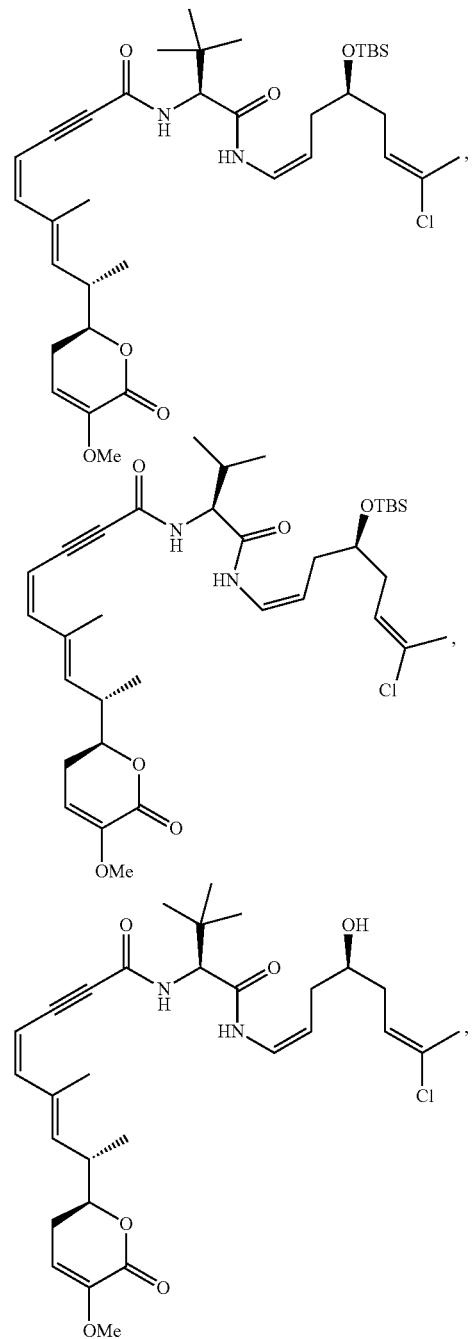

119
-continued
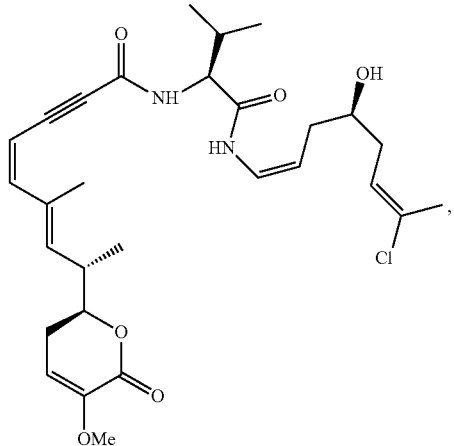
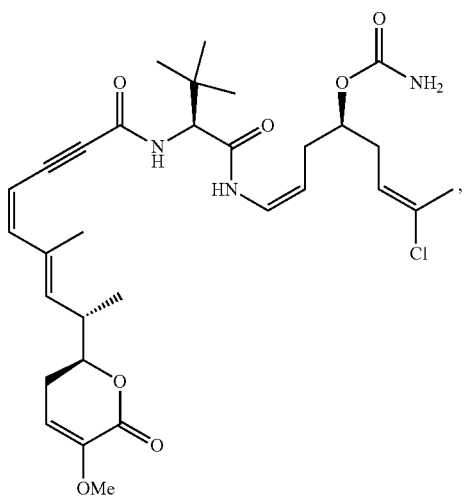
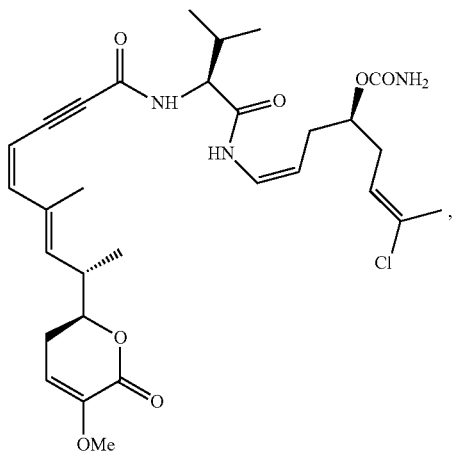
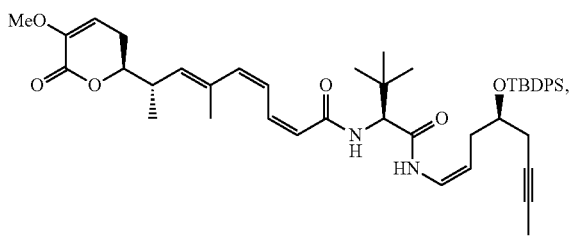
120
-continued
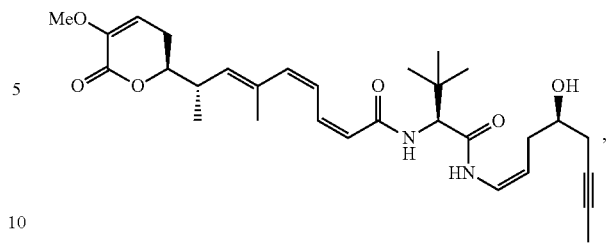
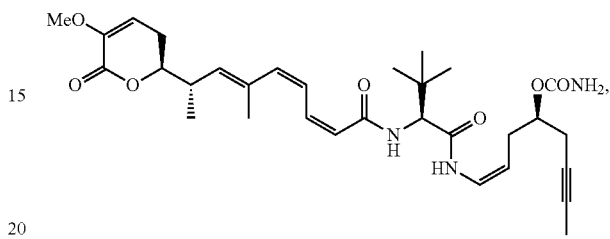
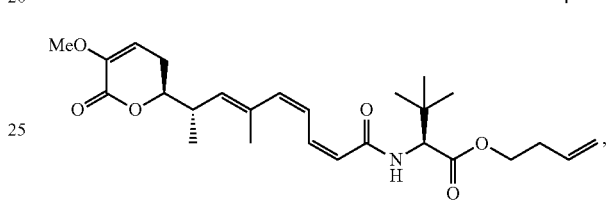
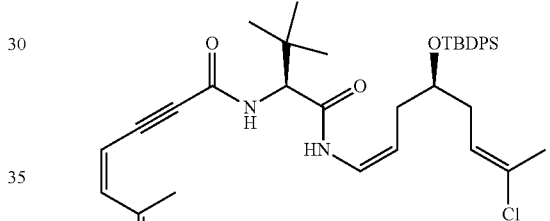
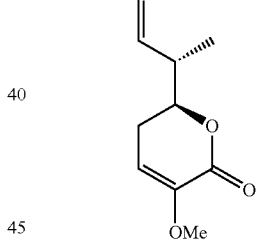
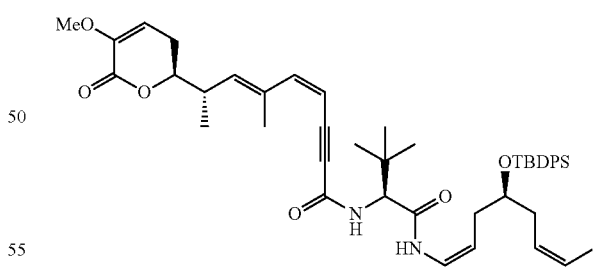
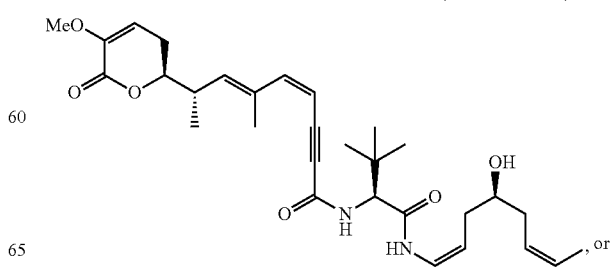

-continued

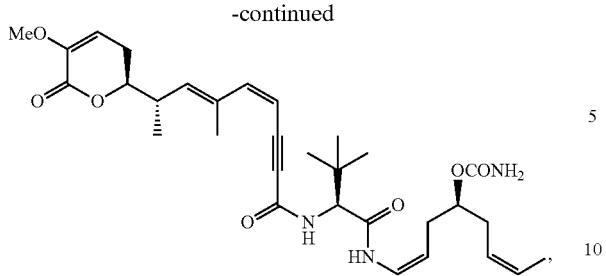

or a pharmaceutically acceptable salt, tautomer, prodrug or stereoisomer thereof.

17. A pharmaceutical composition comprising a compound according to claim 1, or a pharmaceutically acceptable salt, tautomer or stereoisomer thereof, and a pharmaceutically acceptable diluent or carrier.

18. A process for the preparation of compounds according to formula I

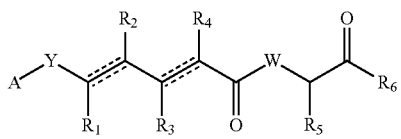

as defined in claim 1 wherein A, Y, W, $R_1$, $R_2$, $R_3$, $R_4$, $R_5$ and $R_6$ are also as defined in claim 1, comprising the coupling of Fragments C and D

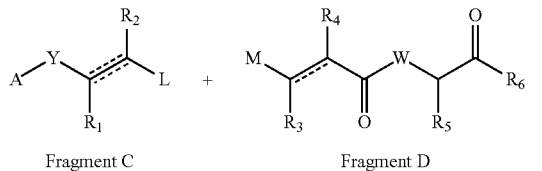

Fragment C          Fragment D wherein $R_1$, $R_2$, $R_3$, $R_4$, $R_5$, $R_6$, A, Y and W are the desired groups as defined in the compound of formula I or a protected hydroxyl group or a protected amino group as needed, and L and M are the appropriate reacting or leaving groups.

19. A process according to claim 18, wherein the compound of formula I is any compound defined in claim 16.

20. A process according to claim 18 wherein leaving group "L" is a halide.

21. A process according to claim 18 wherein leaving group "L" is iodide.

22. A process according to claim 18 wherein reacting group "M" is tributyl tin.

23. A process according to claim 18 wherein Fragment D is:

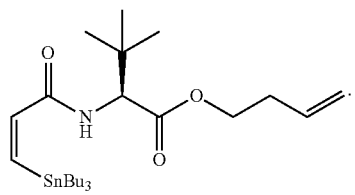

24. A process according to claim 18, wherein Fragment D is:

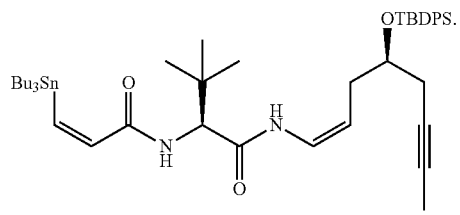

25. A compound of the formula:

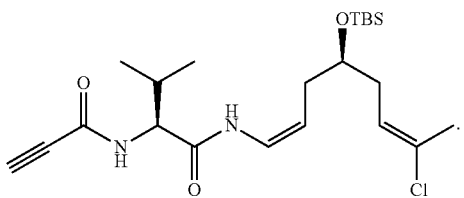 [SMILES: C#CC(=O)N[C@H](C(=O)N/C=C\C[C@H](C/C=C(\C)Cl)O[Si](C)(C)C(C)(C)C)C(C)C]

26. A compound of the formula:

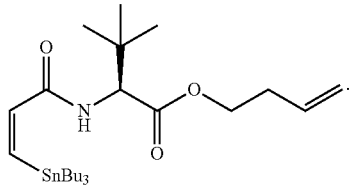

27. A compound of the formula

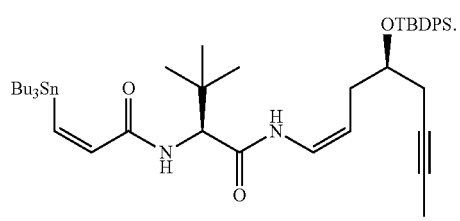

28. A process for the preparation of compounds according to formula I

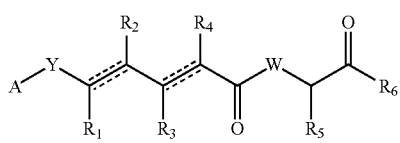

as defined in claim 1 wherein A, Y, W, $R_1$, $R_2$, $R_3$, $R_4$, $R_5$ and $R_6$ are also as defined in claim 1 comprising the coupling of Fragments A and B

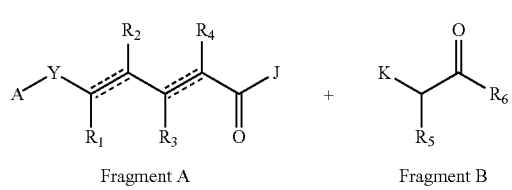

Fragment A          Fragment B wherein $R_1$, $R_2$, $R_3$, $R_4$, $R_5$, $R_6$, A and Y are the desired groups or a protected hydroxyl group or a protected amino group as needed, and J and K are the appropriate reacting or leaving groups.

29. A process according to claim 28, wherein the compound of formula I is any compound defined in claim 16.

30. The process of claim 18, wherein $R_1$, $R_2$, $R_3$, $R_4$, $R_5$, $R_6$, A, Y and W are as defined in the compound of formula I or a protected hydroxyl group.

31. The process of claim 28, wherein $R_1$, $R_2$, $R_3$, $R_4$, $R_5$, $R_6$, A, and Y are as defined in the compound of formula I or a protected hydroxyl group.

\* \* \* \* \*